US009284541B2

(12) United States Patent
Ting et al.

(10) Patent No.: US 9,284,541 B2
(45) Date of Patent: *Mar. 15, 2016

(54) METHODS AND COMPOSITIONS FOR PROTEIN LABELING USING LIPOIC ACID LIGASES

(75) Inventors: Alice Y. Ting, Allston, MA (US); David Baker, Seattle, WA (US); Florian Richter, Seattle, WA (US); Lucas Nivon, Seattle, WA (US); Daniel Shao-Chen Liu, Cambridge, MA (US)

(73) Assignees: Massachusetts Institute of Technology, Cambridge, MA (US); University of Washington through its Center for Commercialization, Seattle, WA (US)

( * ) Notice: Subject to any disclaimer, the term of this patent is extended or adjusted under 35 U.S.C. 154(b) by 1108 days.

This patent is subject to a terminal disclaimer.

(21) Appl. No.: 13/267,761

(22) Filed: Oct. 6, 2011

(65) Prior Publication Data

US 2012/0129159 A1 May 24, 2012

Related U.S. Application Data

(63) Continuation-in-part of application No. 11/983,605, filed on Nov. 9, 2007, now Pat. No. 8,137,925.

(51) Int. Cl.
| | |
|---|---|
| *C12N 9/12* | (2006.01) |
| *C12N 15/00* | (2006.01) |
| *C07H 21/04* | (2006.01) |
| *C12N 15/10* | (2006.01) |
| *C12N 9/00* | (2006.01) |
| *G01N 33/532* | (2006.01) |
| *G01N 33/533* | (2006.01) |

(52) U.S. Cl.
CPC ............... *C12N 9/1241* (2013.01); *C12N 9/93* (2013.01); *C12N 15/102* (2013.01); *C12Y 207/07063* (2013.01); *G01N 33/532* (2013.01); *G01N 33/533* (2013.01); *G01N 2333/9015* (2013.01)

(58) Field of Classification Search
CPC .............................. C12N 9/1241; C12N 15/102
See application file for complete search history.

(56) References Cited

U.S. PATENT DOCUMENTS

| | | | |
|---|---|---|---|
| 5,252,466 | A | 10/1993 | Cronan |
| 6,090,842 | A | 7/2000 | Packer et al. |
| 7,056,683 | B2 | 6/2006 | Ting |
| 7,172,877 | B2 | 2/2007 | Ting |
| 8,137,925 | B2 | 3/2012 | Ting et al. |
| 2004/0115777 | A1 | 6/2004 | Budworth et al. |
| 2005/0233389 | A1 | 10/2005 | Ting et al. |
| 2007/0099248 | A1 | 5/2007 | Ting et al. |
| 2007/0105162 | A1 | 5/2007 | Ting et al. |
| 2011/0130348 | A1 | 6/2011 | Ting et al. |
| 2012/0214201 | A1 | 8/2012 | Ting et al. |

FOREIGN PATENT DOCUMENTS

WO    WO 2005/014570 A1    2/2005

OTHER PUBLICATIONS

Adams, S.R. et al., New biarsenical ligands and tetracysteine motifs for protein labeling in vitro and in vivo: synthesis and biological applications. J Am Chem Soc. May 29, 2002;124(21):6063-76.
Agard, N.J. et al., A comparative study of bioorthogonal reactions with azides. ACS Chem Biol. Nov. 21, 2006;1(10):644-8.
Ali, S.T. and Guest, J.R. Isolation and characterization of lipoylated and unlipoylated domains of the E2p subunit of the pyruvate dehydrogenase complex of *Escherichia coli*. Biochem J. Oct. 1, 1990;271(1):139-45.
Alper, P.B. et al., Metal catalyzed diazo transfer for the synthesis of azides from amines. Tetrahedron Letters. 1996;37:6029-6032.
Amano et al., Chemical xenobiotics and mitochondrial autoantigens in primary biliary cirrhosis: identification of antibodies against a common environmental, cosmetic, and food additive, 2-octynoic acid. J Immunol. May 1, 2005;174(9):5874-83.
Anderson, R.G. et al., Surface distribution and recycling of the low density lipoprotein receptor as visualized with antireceptor antibodies. J Cell Biol. Jun. 1982;93(3):523-31.
Barak, L.S and Webb, W.W. Fluorescent low density lipoprotein for observation of dynamics of individual receptor complexes on cultured human fibroblasts. J Cell Biol. Sep. 1981;90(3):595-604.
Baruah et al., An engineered aryl azide ligase for site-specific mapping of protein-protein interactions through photo-cross-linking. Angew Chem Int Ed Engl. 2008;47(37):7018-21.
Branden et al., Introduction to Protein Structure, Garland Publishing Inc., New York. 1991;247.
Brock, R. et al., Comparison of fixation protocols for adherent cultured cells applied to a GFP fusion protein of the epidermal growth factor receptor. Cytometry. Apr. 1, 1999;35(4):353-62.
Chen, I. et al., Site-specific labeling of cell surface proteins with biophysical probes using biotin ligase. Nat Methods. Feb. 2005;2(2):99-104. Epub Jan. 21, 2005.
Cohen et al., Structure-guided engineering of a Pacific Blue fluorophore ligase for specific protein imaging in living cells. Biochemistry. Sep. 27, 2011;50(38):8221-5. Epub Aug. 31, 2011.

(Continued)

*Primary Examiner* — Yong Pak
(74) *Attorney, Agent, or Firm* — Wolf, Greenfield & Sacks, P.C.

(57) ABSTRACT

The present disclosure provides compositions and methods of use thereof for labeling peptide and proteins in vitro or in vivo. The methods described herein employ lipoic acid ligase or mutants thereof, and lipoic acid analogs (e.g., lipoic acid analogs comprising a resorufin moiety) recognized by lipoic acid ligase and lipoic acid ligase mutants. Also provided herein is a method of imaging protein-protein interaction via a reaction mediated by lipoic acid ligase.

5 Claims, 18 Drawing Sheets

(56) References Cited

OTHER PUBLICATIONS

Dardel, F. et al., Expression in Escherichia coli of a sub-gene encoding the lipoyl domain of the pyruvate dehydrogenase complex of *Bacillus stearothermophilus*. FEBS Lett. May 21, 1990;264(2):206-10. Erratum in: FEBS Lett Jul. 30, 1990;268(1):306.

Debant, A. et al., Receptor cross-linking restores an insulin metabolic effect altered by mutation on tyrosine 1162 and tyrosine 1163. Biochemistry. Jan. 10, 1989;28(1):14-7.

Deisseroth et al., Next-generation optical technologies for illuminating genetically targeted brain circuits. J Neurosci. Oct. 11, 2006;26(41):10380-6.

Devadas et al., Substrate specificity of *Saccharomyces cerevisiae* myristoyl-CoA: protein Nmyristoyltransferase. Analysis of fatty acid analogs containing carbonyl groups, nitrogen heteroatoms, and nitrogen heterocycles in an in vitro enzyme assay and subsequent identification of inhibitors of human immunodeficiency virus I replication. J Biol Chem. Apr. 15, 1992;267(11):7224-39.

Dubois et al., Digital holographic microscopy for the three-dimensional dynamic analysis of in vitro cancer cell migration. J Biomed Opt. Sep.-Oct. 2006;11(5):054032.

Fernández-Suárez et al., Redirecting lipoic acid ligase for cell surface protein labeling with small-molecule probes. Nat Biotechnol. Dec. 2007;25(12):1483-7. Epub Dec. 2, 2007.

Flanagan, J.G. and Vanderhaeghen, P. The ephrins and Eph receptors in neural development. Annu Rev Neurosci. 1998;21:309-45. Review.

Fujiwara, K. et al., Crystal structure of lipoate-protein ligase A from *Escherichia coli*. Determination of the lipoic acid-binding site. J Biol Chem. Sep. 30, 2005;280(39):33645-51. Epub Jul. 25, 2005.

Gama, L. and Breitwieser, G.E. Generation of epitope-tagged proteins by inverse polymerase chain reaction mutagenesis. Methods Mol Biol. 2002;182:77-83.

George, N. et al., Specific labeling of cell surface proteins with chemically diverse compounds. J Am Chem Soc. Jul. 28, 2004;126(29):8896-7.

Green, D.E. et al., Purification and properties of the lipoate protein ligase of *Escherichia coli*. Biochem J. Aug. 1, 1995;309 (Pt 3):853-62.

Green, J.D. et al., Three-dimensional structure of a lipoyl domain from the dihydrolipoyl acetyltransferase component of the pyruvate dehydrogenase multienzyme complex of *Escherichia coli*. J Mol Biol. Apr. 28, 1995;248(2):328-43.

Griffin, B.A. et al., Specific covalent labeling of recombinant protein molecules inside live cells. Science. Jul. 10, 1998;281(5374):269-72.

Griffin, R.J. The medicinal chemistry of the azido group. Prog Med Chem. 1994;31:121-232. Review.

Howarth, M. et al., A monovalent streptavidin with a single femtomolar biotin binding site. Nat Methods. Apr. 2006;3(4):267-73.

Howarth, M. et al., Targeting quantum dots to surface proteins in living cells with biotin ligase. Proc Natl Acad Sci U S A. May 24, 2005;102(21):7583-8. Epub May 16, 2005.

Tin et al., Synthesis of 7-aminocoumarin by Buchwald-Hartwig cross coupling for specific protein labeling in living cells. Chembiochem. Jan. 3, 2011;12(1):65-70.

Kiick, K.L. et al., Incorporation of azides into recombinant proteins for chemoselective modification by the Staudinger ligation. Proc Natl Acad Sci U S A. Jan. 8, 2002;99(1):19-24. Epub Dec. 18, 2001.

Lin, C.W. and Ting, A.Y. Transglutaminase-catalyzed site-specific conjugation of small-molecule probes to proteins in vitro and on the surface of living cells. J Am Chem Soc. Apr. 12, 2006;128(14):4542-3.

Liu et al., Diels-Alder cycloaddition for fluorophore targeting to specific proteins inside living cells. J Am Chem Soc. Jan. 18, 2012;134(2):792-5. Epub Jan. 5, 2012.

Marks, K.M. and Nolan, G.P. Chemical labeling strategies for cell biology. Nat Methods. Aug. 2006;3(8):591-6. Review.

McLean, A.J. and Milligan, G. Ligand regulation of green fluorescent protein-tagged forms of the human beta(1)- and beta(2)-adrenoceptors; comparisons with the unmodified receptors. Br J Pharmacol. Aug. 2000;130(8):1825-32.

Morris, T.W. et al., Lipoic acid metabolism in *Escherichia coli*: the lplA and lipB genes define redundant pathways for ligation of lipoyl groups to apoprotein. J Bacteriol. Jan. 1995;177(1):1-10.

Nauman, D.A. and Bertozzi, C.R. Kinetic parameters for small-molecule drug delivery by covalent cell surface targeting. Biochim Biophys Acta. Dec. 5, 2001;1568(2):147-54.

Novis-Smith, W. and Beumel, J. Preparation of alkynes and dialkynes by reaction of mono-halo and dihaloalkanes with lithium acetylenide-ethylenediamine complex. Synthetic Communications. 1974; 441-442.

Pasquale, E.B. Eph receptor signalling casts a wide net on cell behaviour. Nat Rev Mol Cell Biol. Jun. 2005;6(6):462-75. Review. Erratum in: Nat Rev Mol Cell Biol. Jul. 2005;6(7):589.

Prescher, J.A. and Bertozzi, C.R. Chemistry in living systems. Nat Chem Biol. Jun. 2005;1(1):13-21. Review.

Reche, P. and Perham, R.N. Structure and selectivity in post-translational modification: attaching the biotinyl-lysine and lipoyl-lysine swinging arms in multifunctional enzymes. EMBO J. May 17, 1999;18(10):2673-82.

Saunders, W.S. et al., Molecular cloning of a human homologue of *Drosophila heterochromatin* protein HP1 using anti-centromere autoantibodies with anti-chromo specificity. J Cell Sci. Feb. 1993;104 (Pt 2):573-82.

Scriven, E.F.V. and Turnbull, K. Azides: their preparation and synthetic uses. Chemical Reviews. 1998;88:297-368.

Singh, A.B. and Harris, R.C. Autocrine, paracrine and juxtacrine signaling by EGFR ligands. Cell Signal. Oct. 2005;17(10):1183-93. Review.

Slavoff et al., Imaging protein-protein interactions inside living cells via interaction-dependent fluorophore ligation. J Am Chem Soc. Dec. 14, 2011;133(49):19769-76. Epub Nov.18, 2011.

Tuli, S.S. et al., Immunohistochemical localization of EGF, TGF-alpha, TGF-beta, and their receptors in rat corneas during healing of excimer laser ablation. Curr Eye Res. Sep. 2006;31(9):709-19.

Uttamapinant et al., A fluorophore ligase for site-specific protein labeling inside living cells. Proc Natl Acad Sci U S A. Jun. 15, 2010;107(24):10914-9. Epub Jun. 7, 2010.

Weiss, A. and Littman, D.R. Signal transduction by lymphocyte antigen receptors. Cell. Jan. 28, 1994;76(2):263-74. Review.

Willnow, T.E. The low-density lipoprotein receptor gene family: multiple roles in lipid metabolism. J Mol Med. Mar. 1999;77(3):306-15. Review.

Wimmer-Kleikamp, S.H. and Lackmann, M. Eph-modulated cell morphology, adhesion and motility in carcinogenesis. IUBMB Life. Jun. 2005;57(6):421-31. Review.

Yan et al., N-hydroxysuccinimide ester functionalized perfluorophenyl azides as novel photoactive heterobifunctional cross-linking reagents. The covalent immobilization of biomolecules to polymer surfaces. Bioconjug Chem. Mar.-Apr. 1994;5(2):151-7.

Zhou, Z. et al., Genetically encoded short peptide tags for orthogonal protein labeling by Sfp and AcpS phosphopantetheinyl transferases. ACS Chem Biol. May 22, 2007;2(5):337-46. Epub Apr. 27, 2007.

Fig. 1
n = 5, 7–10 azides
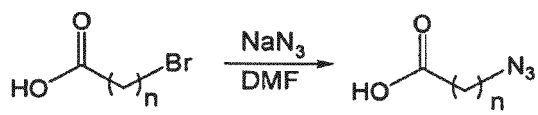
n = 6 azide
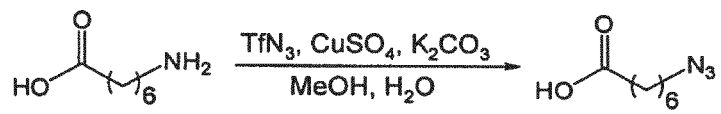
n = 5, 7 alkynes

Fig. 3

| Peptide | Sequence | Derived from | Fused to | % Conversion |
|---|---|---|---|---|
| 1 | GLNDIFEADKAEWHE | BirA AP | N term. | < 5 |
| 2 | GDTLCIVEADKAMNQIE | E. coli BCCP | N term. | < 5 |
| 3 | GDTLCIVEADKASMEIP | E. coli BCCP | N term. | 53.9 ± 1.9 |
| 4 | EQSLITVEGDKASMEVP | E. coli E2p | N term. | < 5 |
| 5 | DDVLCEVQNDKAVVEIP | B. stearoth. E2p | N term. | 11.9 ± 3.1 |
| 6 | DEVLVEIETDKVVLEVP | E. coli E2o | N term. | 99.0 ± 7.5 |
| 7 | GDDCAVAESVKAASDIY | E. coli H-protein | N term. | < 5 |
| 8 | DEVLVEIETDKAVLEVP | E. coli E2o | N term. | 100 ± 8 |
| 9 | DEVLVEIETDKAVLEVP | E. coli E2o | C term. | 18.9 ± 2.4 |
| 10 | DEVLVEIETDKAVLEVPGGEEE | E. coli E2o | C term. | 51.7 ± 3.5 |

Fig. 5A
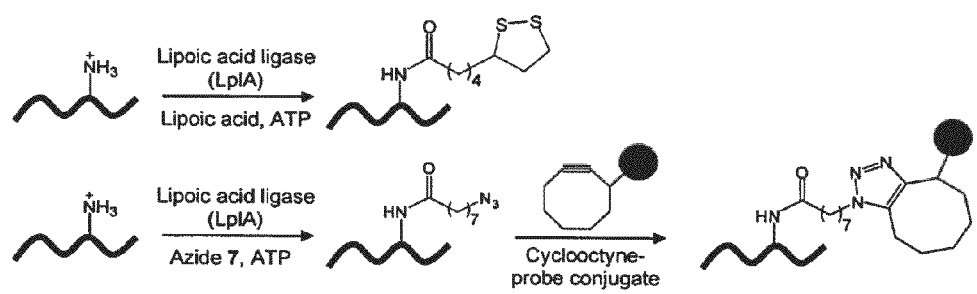
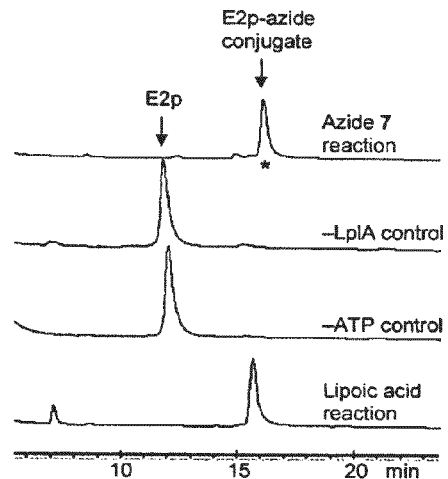
| Substrate | | % Conversion |
|---|---|---|
| Lipoic acid | | 100 ± 3 |
| Azide | n = 5 | 14.9 ± 0.6 |
| | n = 6 | 11.3 ± 0.4 |
| | n = 7 | 55.4 ± 5.7 |
| | n = 8 | 10.2 ± 0.4 |
| | n = 9 | 4.57 ± 0.11 |
| | n = 10 | 3.28 ± 0.17 |
| Alkyne | n = 4 | 3.59 ± 0.23 |
| | n = 5 | 3.15 ± 0.19 |
| | n = 7 | 6.37 ± 0.15 |
| | n = 8 | 5.15 ± 0.23 |
Fig. 5B                                Fig. 5C

Fig. 10

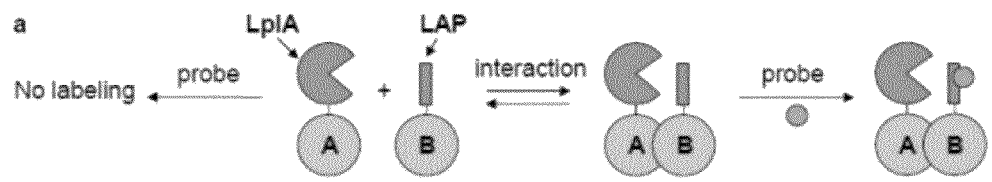

b

| Enzyme | Peptide | Probe | $K_m$ for peptide | $k_{cat}$ | Reference |
|---|---|---|---|---|---|
| BirA | AP | biotin | 25 µM | 12 min$^{-1}$ | Beckett et al., 1999 |
| BirA | AP(-3) | biotin | 345 µM | 0.53 min$^{-1}$ | Fernández-Suárez et al., 2008 |
| LplA | LAP2 | lipoic acid | 13 µM | 13.2 min$^{-1}$ | Puthenveetil et al., 2009 |
| LplA$^{W37V}$ | LAP2 | coumarin | Not determined† | 1.14 min$^{-1}$ | Uttamapinant et al., 2010 |
| LplA | LAP1 | 8-azido-octanoic acid | > 300 µM | 2.48 min$^{-1}$ | Fernández-Suárez et al., 2007 |
| LplA$^{W37V}$ | LAP1 | coumarin | 681 µM | 0.60 min$^{-1}$ | This work |

US 9,284,541 B2

METHODS AND COMPOSITIONS FOR PROTEIN LABELING USING LIPOIC ACID LIGASES

RELATED APPLICATIONS

This application is a continuation-in-part application of U.S. application Ser. No. 11/983,605, filed on Nov. 9, 2007, the entire content of which is herein incorporated by reference.

GOVERNMENT SUPPORT

This invention was made with government support awarded by the National Institutes of Health under Grant Number R01 GM072670-01. The Government has certain rights in the invention.

BACKGROUND OF THE INVENTION

Biophysical probes such as fluorophores, spin labels, and photoaffinity tags have greatly improved the understanding of protein structure and function in vitro, and there is great interest in using them inside cells to study proteins within their native context. The major bottleneck to using such probes inside cells, however, is the difficulty of targeting the probes with very high specificity to particular proteins of interest, given the chemical heterogeneity of the cell interior. The most prominent method for labeling cellular proteins is to genetically encode green fluorescent protein (GFP) or one of its variants as a fusion to the protein of interest. Because GFPs are genetically encoded, their labeling is absolutely specific and GFP variants have proven extremely useful for in vivo studies of protein localization, however, they still have severe limitations such as their large size (~235 amino acids), which can perturb the function of the protein of interest, and the fact that they are not very bright and only amenable to optical microscopy. For example, the best of the previously described methods, the FlAsH labeling method uses an extremely small tetracysteine motif to direct a biarsenical-containing probe. This method has yielded exciting new biological information, but suffers from poor specificity, and cell toxicity. Most other methods such as the SNAP/AGT, Halotag, DHFR, FKBP(12), and single-chain antibody methods use protein rather than peptide-based targeting sequences, raising concerns about steric interference with receptor function. Peptide-based targeting methods include FlAsH, $His_6$-tag labeling, phosphopantetheinyl transferase labeling, transglutaminase labeling, and keto/biotin ligase labeling. $His_6$ labeling and FlAsH suffer from probe dissociation, whereas ketone/biotin lipase and transglutaminase are restricted to labeling at the cell surface.

SUMMARY OF THE INVENTION

The invention relates in part to labeling of proteins (or fragments thereof) using lipoic acid ligase and/or lipoic acid ligase mutants. Methods and compositions of the invention provide labeling specificity while also expanding the scope of compatible probe structures for labeling of proteins. Labeling of polypeptides or proteins can be performed in vitro or in vivo. The invention also provides, inter alia, lipoic acid ligase mutants, lipoic acid analogs, and acceptor polypeptides and methods of use thereof for labeling proteins. It also provides screening methods for identifying further lipoic acid ligase mutants, lipoic acid analogs, and acceptor polypeptides.

According to one aspect of the invention, methods for labeling a target protein are provided. the methods include contacting a fusion protein with a lipoic acid analog, and allowing sufficient time for the lipoic acid analog to be conjugated to the fusion protein via an acceptor polypeptide, in the presence of a lipoic acid ligase or mutant thereof, wherein the fusion protein is a fusion of the target protein and the acceptor polypeptide. In some embodiments, the lipoic acid analog comprises an alkyl azide, or an alkyne carboxylic acid, an aryl azide photoaffinity probe, or a fluorophore substrate. In certain embodiments, the lipoic acid analog is detectably labeled. In some embodiments, the lipoic acid analog is directly detectable. In some embodiments, the directly detectable label is coumarin, fluorescein, an aryl azide, a diazirine, a benzophenone, a resorufin, a xanthene-type fluorophore, a chloroalkane, a metal-binding ligand, or a derivative thereof. In some embodiments, the detectable label is coumarin. In certain embodiments, the lipoic acid analog is labeled with an indirectly detectable label. In some embodiments, the indirectly detectable label is an enzyme. In some embodiments, the lipoic acid analog is labeled with a membrane impermeant label. In certain embodiments, the lipoic acid analog is labeled after conjugation to the fusion protein. In some embodiments, the lipoic acid analog is labeled with a cyclooctyne conjugate. In some embodiments, the cyclooctyne conjugate is detectably labeled. In certain embodiments, the detectable label is coumarin, fluorescein, a aryl azide, a diazirine, a benzophenone, a resorufin, a xanthene-type fluorophore, a chloroalkane, a metal-binding ligand, or a derivative thereof. In some embodiments, the target protein is a cell surface protein. In some embodiments, the fusion protein is in a cell. In some embodiments, the cell expresses the lipoic acid ligase or mutant thereof. In certain embodiments, the cell is a eukaryotic cell. In some embodiments, the cell is a bacterial cell. In certain embodiments, the acceptor polypeptide comprises an amino acid sequence of any one of SEQ ID NO:1, 2, 3, 4, 5, 6, 7, 8, 9, or 10, or a functional variant thereof. In some embodiments, the functional variant of any one of SEQ ID NO:1, 2, 3, 4, 5, 6, 7, 8, 9, or 10 comprises an amino acid sequence that has up to 85%, 90%, 95%, or 99% identity to SEQ ID NO:1, 2, 3, 4, 5, 6, 7, 8, 9, or 10 and is a substrate for a lipoic acid ligase or mutant thereof. In some embodiments, the acceptor polypeptide comprises an amino acid sequence of SEQ ID NO: 10. In some embodiments, the acceptor polypeptide is N- or C-terminally fused to the target protein. In certain embodiments, the lipoic acid ligase is an *E. coli* lipoic acid ligase or mutant thereof. In some embodiments, the lipoic acid ligase is LplA. In some embodiments, the lipoic acid ligase mutant includes an amino acid sequence of wild-type LplA that includes a substitution at one or more of residues corresponding to residue 16, 17, 19, 20, 21, 37, 37+71, 37+20, 37+35, 35, 41, 70, 71, 72, 79, 85, 87, 140, 147, and 149 of SEQ ID NO:11. In certain embodiments, the lipoic acid ligase mutant comprises an amino acid sequence of LplA having one or more of the amino acid substitution corresponding to substitution of N16A, L17A, V19A, E20A, E21A, W37A, W37G, W37S, W37V, W37A+S71A, W37A+E20A, W37L, W37I, W37T, W37N, W37V+E20G, W37V+F35A, W37V+E20A, F35A, N41A, R70A, S71A, S72A, H79A, C85A, T87A, R140A, F147A, H149A, or H149V of SEQ ID NO:11. In some embodiments, the lipoic acid ligase comprises the amino acid sequence set forth as SEQ ID NO:11. In some embodiments, the lipoic acid ligase mutant comprises an amino acid sequence that has up to 85%, 90%, 95%, or 99% identity to the amino acid sequence of SEQ ID NO:11 and ligates lipoic acid and/or a lipoic acid analog to an acceptor polypeptide. In certain embodiments, the lipoic acid ligase is a homolog of an *E. coli* lipoic acid ligase or a mutant of a homolog of an *E. coli* lipoic acid ligase. In some embodiments, the lipoic acid ligase is *Thermoplasma acidophilum* LplA; *Plasmodium falciparum* LipL1, or LipL2; *Oryza Sativa* LplA; *Streptococcus pneumoniae* LplA; or a homolog from *Pyrococcus horikoshii; Saccharomyces cerevisiae; Trypanosoma cruzi; Bacillus subtilis*; or *Leuconostoc mesenteroides*. In some embodiments, the method is performed in a cell-free environment. In some embodiments, the method is performed in a cell. In certain embodiments, the acceptor polypeptide is fused to the target protein via a cleavable bond or linker.

According to another aspect of the invention, composition that include a lipoic acid ligase mutant that binds to a lipoic acid analog are provided. In some embodiments, the lipoic acid ligase mutant comprises an amino acid substitution in a lipoic acid interaction and activation domain. In some embodiments, the lipoic acid ligase mutant comprises an amino acid sequence of wild-type LplA comprising a substitution at one or more of residues 16, 17, 19, 20, 21, 37, 37+71, 37+20, 37+35, 35, 41, 70, 71, 72, 79, 85, 87, 140, 147, and 149. In certain embodiments, the lipoic acid ligase mutant comprises the amino acid sequence of LplA having one or more of the amino acid substitutions corresponding to a substitution N16A, L17A, V19A, E20A, E21A, W37A, W37G, W37S, W37V, W37A+S71A, W37A+E20A, W37L, W37I, W37T, W37N, W37V+E20G, W37V+F35A, W37V+E20A, F35A, N41A, R70A, S71A, S72A, H79A, C85A, T87A, R140A, F147A, H149A, or H149V of SEQ ID NO:11. In some embodiments, the lipoic acid ligase mutant comprises an amino acid sequence that has up to 85%, 90%, 95%, or 99% identity to a wild-type lipoic acid ligase sequence and ligates lipoic acid and/or a lipoic acid analog to an acceptor polypeptide. In some embodiments, the wild-type lipoic acid ligase sequence is the sequence set forth as SEQ ID NO:11. In some embodiments, the lipoic acid ligase homolog or a mutant of a homolog of an *E. coli* lipoic acid ligase. In certain embodiments, the lipoic acid ligase is *Thermoplasma acidophilum* LplA; *Plasmodium falciparum* LipL1, or LipL2; *Oryza Sativa* LplA; *Streptococcus pneumoniae* LplA; or a homolog from *Pyrococcus horikoshii; Saccharomyces cerevisiae; Trypanosoma cruzi; Bacillus subtilis*; or *Leuconostoc mesenteroides*. In some embodiments, the lipoic acid ligase mutant isolated. In some embodiments, the lipoic acid ligase mutant has altered binding affinity to lipoic acid compared to wild-type lipoic acid ligase. In certain embodiments, the lipoic acid ligase mutant has wild type binding affinity to lipoic acid. In some embodiments, the lipoic acid analog is an alkyl azide, an alkyne carboxylic acid, an aryl azide photoaffinity probe, or a fluorophore substrate. In some embodiments, the alkyl azide is a modified alkyl azide and the alkyne carboxylic acid is a modified alkyne carboxylic acid. In some embodiments, the lipoic acid analog comprises coumarin.

According to yet another aspect of the invention, composition that include a nucleic acid encoding a lipoic acid ligase mutant that binds to a lipoic acid analog are provided. In certain embodiments, the nucleic acid sequence comprises the nucleotide sequence set forth as SEQ ID NO:12. In some embodiments, the lipoic acid ligase mutant has a nucleic acid sequence that has up to 85%, 90%, 95%, or 99% identity to the nucleic acid sequence of a wild-type lipoic acid ligase and ligates lipoic acid and/or a lipoic acid analog to an acceptor polypeptide. In some embodiments, the nucleic acid of the wild-type lipoic acid ligase has the nucleotide sequence set forth as SEQ ID NO:12. In certain embodiments, the lipoic acid ligase mutant comprises an amino acid sequence of wild-type LplA comprising a substitution at one or more of residues corresponding to residue 16, 17, 19, 20, 21, 37, 37+71, 37+20, 37+35, 35, 41, 70, 71, 72, 79, 85, 87, 140, 147, and 149 of set SEQ ID NO:11. In some embodiments, the lipoic acid ligase mutant comprises the amino acid sequence of LplA with one or more of the amino acid substitutions corresponding to a substitution of N16A, L17A, V19A, E20A, E21A, W37A, W37G, W37S, W37V, W37A+S71A, W37A+E20A, W37L, W37I, W37T, W37N, W37V+E20G, W37V+F35A, W37V+E20A, F35A, N41A, R70A, S71A, S72A, H79A, C85A, T87A, R140A, F147A, H149A, or H149V of SEQ ID NO:11. In some embodiments, the nucleic acid is isolated. In certain embodiments, According to another aspect of the invention, a vector that includes any of the aforementioned nucleic acids of any forgoing aspect of the invention are provided.

According to another aspect of the invention, a host cell that includes any of the aforementioned vectors of any forgoing aspect of the invention are provided. In some embodiments, the nucleic acid is inducibly expressed.

According to yet another aspect of the invention, a process for preparing a lipoic acid ligase mutant is provided. The process includes culturing any aforementioned host cell of any foregoing aspect of the invention and recovering the lipoic acid ligase mutant from the culture.

According to another aspect of the invention, compositions are provided. The compositions include a lipoic acid analog that binds to lipoic acid ligase and/or a mutant thereof, wherein the lipoic acid analog is a modified alkyl azide or a modified alkyne carboxylic acid. In some embodiments, the lipoic acid analog is an alkyl azide, a linear alkyne, or an alkyl halide. In some embodiments, the lipoic acid analog is isolated.

According to another aspect of the invention, a composition is provided. The composition includes a lipoic acid analog that binds to lipoic acid ligase or mutant thereof, wherein the lipoic acid analog is an aryl azide, diazirine, or benzophenone photoaffinity probe or a fluorophore substrate. In certain embodiments, the lipoic acid analog is a 4-azido-2,3,5,6-tetrafluorobenzoic derivative, a 7,7'-azo-octanoic acid, a benzophenone, or a 6,8-difluoro-7-hydroxycoumarin fluorophore derivative. In some embodiments, the lipoic acid analog is isolated.

According to yet another aspect of the invention, compositions are provided. The compositions include an acceptor polypeptide that functions as a substrate for a lipoic acid ligase or mutant thereof and comprises an amino acid sequence of SEQ ID NO:1, 2, 3, 4, 5, 6, 7, 8, 9, or 10, or a functional variant thereof. In some embodiments, the acceptor polypeptide functional variant comprises an amino acid sequence that has up to 85%, 90%, 95%, or 99% identity to at least one of SEQ ID NOs: 1, 2, 3, 4, 5, 6, 7, 8, 9, or 10 and is a substrate for a lipoic acid ligase or mutant thereof. In some embodiments, the acceptor polypeptide comprises an amino acid sequence of SEQ ID NO: 10. In certain embodiments, the acceptor polypeptide is N- or C-terminally fused to a target protein.

According to yet another aspect of the invention, methods for identifying a lipoic acid ligase having specificity for a lipoic acid analog are provided. The methods include contacting a lipoic acid or lipoic acid analog with an acceptor polypeptide in the presence of a candidate lipoic acid ligase molecule, and detecting a lipoic acid or lipoic acid analog that is bound to the acceptor polypeptide, wherein the presence of a lipoic acid or lipoic acid analog bound to an acceptor polypeptide indicates that the candidate lipoic acid ligase molecule is a lipoic acid ligase that has specificity for the lipoic acid or lipoic acid analog. In some embodiments, the lipoic acid ligase is a homolog or mutant lipoic acid ligase. In some embodiments, the lipoic acid or lipoic acid analog is directly detectable. In some embodiments, the lipoic acid analog is coumarin. In certain embodiments, the lipoic acid or lipoic acid analog is conjugated to a detectable label. In some embodiments, the detectable label is a directly detectable label. In some embodiments, the directly detectable label is a fluorophore. In certain embodiments, the detectable label is an indirectly detectable label. In some embodiments, the indirectly detectable label is an enzyme. In some embodiments, detecting a lipoic acid or lipoic acid analog comprises detecting the detectable label conjugated to the lipoic acid or lipoic acid analog. In certain embodiments, the acceptor polypeptide comprises an amino acid sequence of one of SEQ ID NO:1, 2, 3, 4, 5, 6, 7, 8, 9, or 10 or a functional variant thereof. In some embodiments, the functional variant comprises an amino acid sequence that has up to 85%, 90%, 95%, or 99% identity to SEQ ID NO:10 and is a substrate for a lipoic acid ligase or mutant thereof. In some embodiments, the acceptor polypeptide has an amino acid sequence comprising SEQ ID NO:10. In some embodiments, the lipoic acid analog is an alkyl azide, an alkyne carboxylic acid, an aryl azide affinity probe, or a fluorophore substrate. In certain embodiments, the lipoic acid analog is detected using a fluorescent detection system, a luminescent detection system, an enzyme detection system, or an optical detection system. In some embodiments, the method also includes removing unbound lipoic acid or lipoic acid analog prior to detecting bound lipoic acid analog. In some embodiments, the method also includes isolating the candidate molecule that is a lipoic acid ligase mutant having specificity for the lipoic acid or lipoic acid analog.

According to yet another aspect of the invention, methods for identifying a lipoic acid analog having specificity for a lipoic acid ligase or a mutant thereof, are provided. The methods include combining an acceptor polypeptide with a candidate lipoic acid analog molecule in the presence of a lipoic acid ligase or mutant thereof and determining the presence of lipoic acid analog incorporation, wherein lipoic acid analog incorporation is indicative of a candidate lipoic acid analog having specificity for a lipoic acid ligase or mutant thereof. In some embodiments, the lipoic acid analog comprises an alkyl azide, an alkyne carboxylic acid, a modified alkyl azide, a modified alkyne carboxylic acid, an aryl azide affinity probe, a diazirine affinity probe, a benzophenone affinity probe, or a fluorophore substrate. In certain embodiments, the acceptor polypeptide comprises an amino acid sequence of SEQ ID NO:1, 2, 3, 4, 5, 6, 7, 8, 9, or 10, or a variant thereof. In some embodiments, the variant of the acceptor polypeptide comprises an amino acid sequence that has up to 85%, 90%, 95%, or 99% identity to any one of the amino acid sequences set forth as SEQ ID NO:1, 2, 3, 4, 5, 6, 7, 8, 9, or 10 and is a substrate for a lipoic acid ligase or mutant thereof. In some embodiments, the acceptor polypeptide has an amino acid sequence comprising SEQ ID NO:10. In some embodiments, the lipoic acid analog is directly detectable. In certain embodiments, the lipoic acid analog is coumarin. In some embodiments, the lipoic acid analog is conjugated to a detectable label. In some embodiments, the detectable label is a directly detectable label. In some embodiments, the directly detectable label is a fluorophore. In certain embodiments, the detectable label is an indirectly detectable label. In some embodiments, the indirectly detectable label is an enzyme. In some embodiments, detecting a lipoic acid analog comprises detecting the detectable label conjugated to the lipoic acid analog. In certain embodiments, the lipoic acid analog is detected using a fluorescent detection system, a luminescent detection system, an enzyme detection system, or an optical detection system. In some embodiments, the method also includes removing unbound lipoic acid analog prior to detecting bound lipoic acid analog. In some embodiments, the method also includes isolating the candidate molecule that is a lipoic acid ligase mutant having specificity for a lipoic acid analog.

According to another aspect of the invention, methods for identifying an acceptor polypeptide having specificity for a lipoic acid ligase or mutant thereof are provided. The methods include combining an candidate acceptor polypeptide with a labeled lipoic acid or analog thereof in the presence of a lipoic acid ligase or mutant thereof and determining a level of lipoic acid or lipoic acid analog incorporation, wherein lipoic acid or lipoic acid analog incorporation is indicative of a candidate acceptor polypeptide having specificity for a lipoic acid ligase or mutant thereof. In some embodiments, the lipoic acid analog comprises an alkyl azide, an alkyne carboxylic acid, a modified alkyl azide, a modified alkyne carboxylic acid, an aryl azide affinity probe, a diazirine affinity probe, a benzophenone, or a fluorophore substrate. In certain embodiments, the acceptor polypeptide comprises a variant of an amino acid sequence of SEQ ID NO:1, 2, 3, 4, 5, 6, 7, 8, 9, or 10. In some embodiments, the variant of the acceptor polypeptide comprises an amino acid sequence that has up to 85%, 90%, 95%, or 99% identity to any one of the amino acid sequences set forth as SEQ ID NO:1, 2, 3, 4, 5, 6, 7, 8, 9, or 10 and is a substrate for a lipoic acid ligase or mutant thereof. In some embodiments, the lipoic acid analog is directly detectable. In some embodiments, the lipoic acid analog is coumarin. In certain embodiments, the lipoic acid analog is conjugated to a detectable label. In some embodiments, the detectable label is a directly detectable label. In some embodiments, the directly detectable label is a fluorophore. In some embodiments, the detectable label is an indirectly detectable label. In certain embodiments, the indirectly detectable label is an enzyme. In some embodiments, detecting a lipoic acid analog comprises detecting the detectable label conjugated to the lipoic acid analog. In some embodiments, the lipoic acid analog is detected using a fluorescent detection system, a luminescent detection system, an enzyme detection system, or an optical detection system. In some embodiments, the method also includes removing unbound lipoic acid analog prior to detecting bound lipoic acid analog. In certain embodiments, the method also includes isolating the candidate molecule that is a lipoic acid ligase mutant having specificity for a lipoic acid analog.

In another aspect, this disclosure provides lipoic acid ligase mutants that are specific to resorufin (i.e., capable of conjugating a lipoic acid analog that contains a resorufin moiety to an acceptor polypeptide), the encoding nucleic acid molecules, vectors (e.g., expression vectors) comprising such nucleic acids, host cells comprising the vectors, methods of using such lipoic acid ligase mutants to label a target protein with resorufin, and kits for performing the just-noted methods.

A resorufin-specific lipoic acid mutant as disclosed herein can comprise an amino acid sequence at least 85% (e.g., 90%, 95%, 98%, or 99%) to SEQ ID NO:11 and includes mutations at residues corresponding to E20 (e.g., E20A), F147 (e.g., F147A), and optionally H149 (e.g., H149G) in SEQ ID NO:11. In some embodiments, the mutant is otherwise identical to a wild-type lipoic acid ligase except for the amino acid residue substitutions corresponding to E20A, F147A, and optionally H149G in SEQ ID NO:11.

Also within the scope of the disclosure are nucleic acids comprising nucleotide sequences each encoding a resorufin-specific lipoic acid mutant described above, vectors, such as expression vectors, comprising a nucleotide sequence encoding the mutant, and host cells comprising the vectors. Host cells comprising such expression vectors can be used to produce the resorufin-specific lipoic acid mutants via conventional recombinant technology.

The resorufin-specific lipoic acid mutants can be used in a method for labeling a target protein with resorufin. The method comprises (a) obtaining any of the resorufin-specific lipoic acid mutants disclosed herein, a fusion protein comprising a target protein and an acceptor polypeptide as disclosed herein, and a lipoic acid analog comprising an aliphatic carboxylic acid substituted with a resorufin moiety (which can be substituted or unsubstituted), and (b) contacting the fusion protein with the lipoic acid analog in the presence of the resorufin-specific lipoic acid ligase mutant under conditions allowing conjugation of the lipoic acid analog to the acceptor polypeptide. The fusion protein can be expressed in cells such as eukaryotic cells or bacterial cells.

In some embodiments, the acceptor polypeptide in the fusion protein comprises an amino acid sequence at least 85% (e.g., 90%, 95%, 99%, or 100%) identical to one of SEQ ID NOs: 1-10.

In other embodiments, the acceptor polypeptide comprises an amino acid sequence of 8-13 amino acids, which includes a central lysine residue at position 0, a hydrophobic residue at position +1 (e.g., valine, isoleukine, leucine, or phenylalanine), an aromatic residue at position +2 (e.g., tryptophan or phenylalanine), an aromatic or aliphatic hydrophobic residue at position +3 (e.g., tyrosine, histidine, phenylalanine, isoleucine, valine, leucine, or threonine), a glutamic acid or aspartic acid residue at position +4 (e.g., glutamic acid or aspartic acid), an aliphatic hydrophobic residue at position +5 (e.g., leucine, isoleucine, or phenylalanine), an aspartic acid, asparagine, glutamic acid, tyrosine, or alanine residue at position -1, a glutamic acid or aspartic acid residue at position -3, a hydrophobic or aromatic residue at position -4 (e.g., phenylalanine, valine, leucine, or an isoleucine). Optionally, position +7 is a serine residue, an alanine residue, or is absent, position -5 is a glycine residue or is absent, position +6 is an aspartic acid, glutamic acid, serine, threonine, cysteine, or tyrosine residue, or position -2 is an isoleucine, histidine, leucine, or arginine residue.

In yet other embodiments, the acceptor polypeptide comprises an amino acid sequence of 8-13 amino acids, which includes a central lysine residue at position 0, a valine residue at position +1, a tryptophan residue at position +2, a glutamic acid or aspartic acid residue at position +4, a hydrophobic residue at position +5, a glutamic acid residue at position -3, and a phenylalanine residue at position -4. In one example, the acceptor polypeptide comprises the amino acid sequence GFEIDKVWYDLDA (SEQ ID NO:32).

The lipoic acid analog used in the just-described method can be resorufin A or resorufin B shown in FIG. 8, which can be substituted or unsubstituted. In one example, the lipoic acid analog is resorufin-$AM_2$, including isomer a and isomer b (see FIG. 9).

Also disclosed herein are kits for performing the labeling methods described above. These kits can comprise (a) any of the resorufin-specific lipoic acid ligase mutants disclosed herein, (b) a lipoic acid analog comprising an aliphatic carboxylic acid substituted with a resorufin moiety, and (c) an expression vector designed for producing a fusion protein comprising a target protein and an acceptor polypeptide disclosed herein. The expression vector can comprise a first nucleotide acid sequence coding for the acceptor polypeptide and a cloning site for insertion of nucleotide sequence coding for a target protein.

The present disclosure also features a method for imaging protein-protein interaction, comprising the following steps:

providing (i) a first fusion protein containing an acceptor polypeptide and a first target protein, and (ii) a second fusion protein containing a lipoic acid ligase and a second target protein, and (iii) a lipoic acid analog;

contacting the first fusion protein with the lipoic acid analog in the presence of the second fusion protein;

determining whether the first fusion protein is labeled with the lipoic acid analog. Labeling of the first fusion protein with the lipoic acid analog is indicative of interaction between the first target protein and the second target protein.

In some embodiments, the acceptor polypeptide comprises an amino acid sequence at least 85% identical to SEQ ID NO:1, 2, 3, 4, 5, 6, 7, 8, 9, or 10; the lipoic acid ligase comprises an amino acid sequence at least 85% identical to SEQ ID NO:11; and the lipoic acid anolog comprises comprising an aliphatic carboxylic acid substituted with an alkyl azide, an alkyne, an alkyl halide, an aryl azide photoaffinity probe, a diazirine photoprobe, a benxophenone photoaffinity probe, or a fluorophore moiety. In one example, the lipoic acid ligase comprises a mutation at the position corresponding to W37 (e.g., amino acid substitution W37V, W37A, W37L, W37S, or W37I) in SEQ ID NO:11, and the lipoic acid analog comprises an aliphatic carboxylic acid substituted with a courmarin moiety or an aryl azide moiety. In another example, the lipoic acid ligase comprises a mutation at positions corresponding to E20 (e.g., E20A) and F147 (e.g., F147A) in SEQ ID NO:11, which can further include a mutation at the position corresponding to H149 (e.g., H149G) in SEQ ID NO:11, and the lipoic acid analog comprises an aliphatic carboxylic acid substituted with a resorufin moiety.

These and other objects of the invention will be described in further detail in connection with the detailed description of the invention.

BRIEF DESCRIPTION OF THE DRAWINGS

FIG. 2 shows a mass spectrometric trace and a Michaelis-Menten plot showing characterization of LplA-catalyzed azide 7 ligation.

FIG. 3 shows peptides prepared for the engineering of a peptide substrate for LplA.

```
GLNDIFEADKAEWHE is SEQ ID NO: 1;

GDTLCIVEADKAMNQIE is SEQ ID NO: 2;

GDTLCIVEADKASMEIP is SEQ ID NO: 3;

EQSLITVEGDKASMEVP is SEQ ID NO: 4;

DDVLCEVQNDKAVVEIP is SEQ ID NO: 5;

DEVLVEIETDKVVLEVP is SEQ ID NO: 6;
```

-continued

GDDCAVAESVKAASDIY is SEQ ID NO: 7;

DEVLVEIETDKAVLEVP is SEQ ID NO: 8;

DEVLVEIETDKAVLEVP is SEQ ID NO: 9;
and

DEVLVEIETDKAVLEVPGGEEE is SEQ ID NO: 10.

Figure 4:
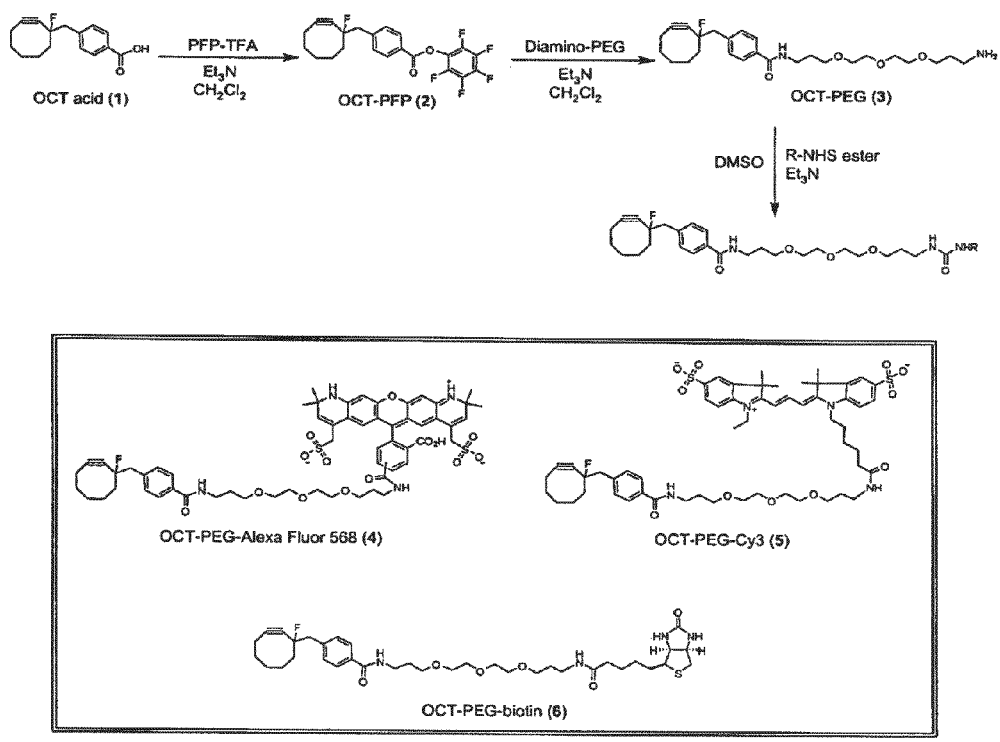
Figure 5D:
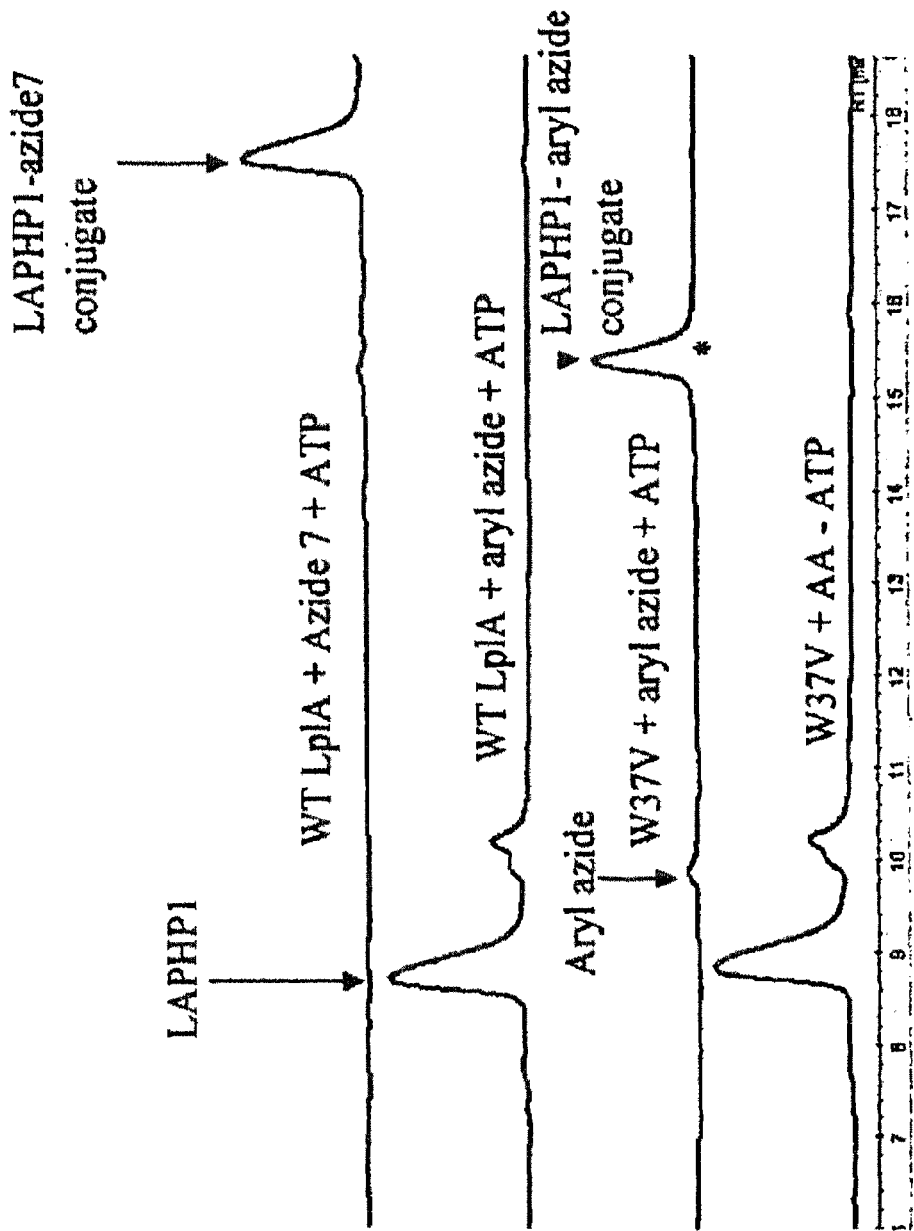
Figure 5E:
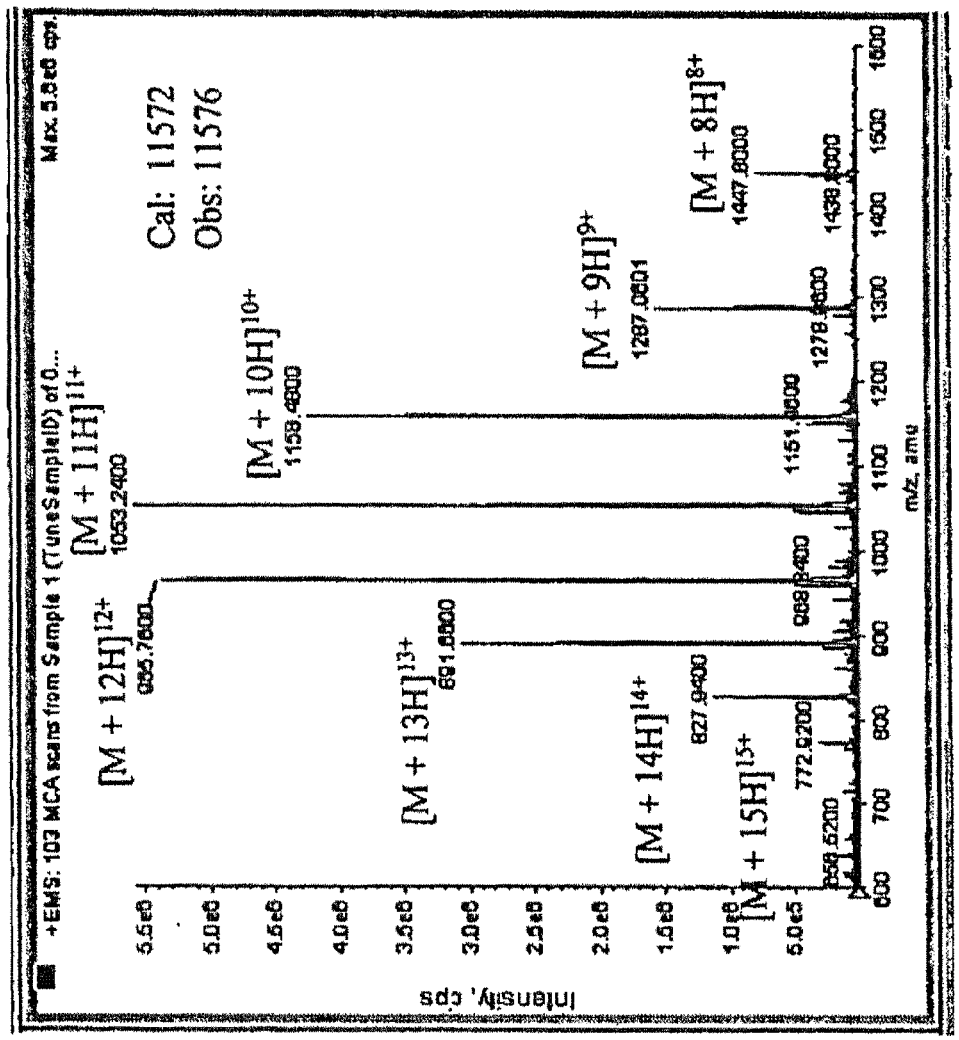
Figure 5F:
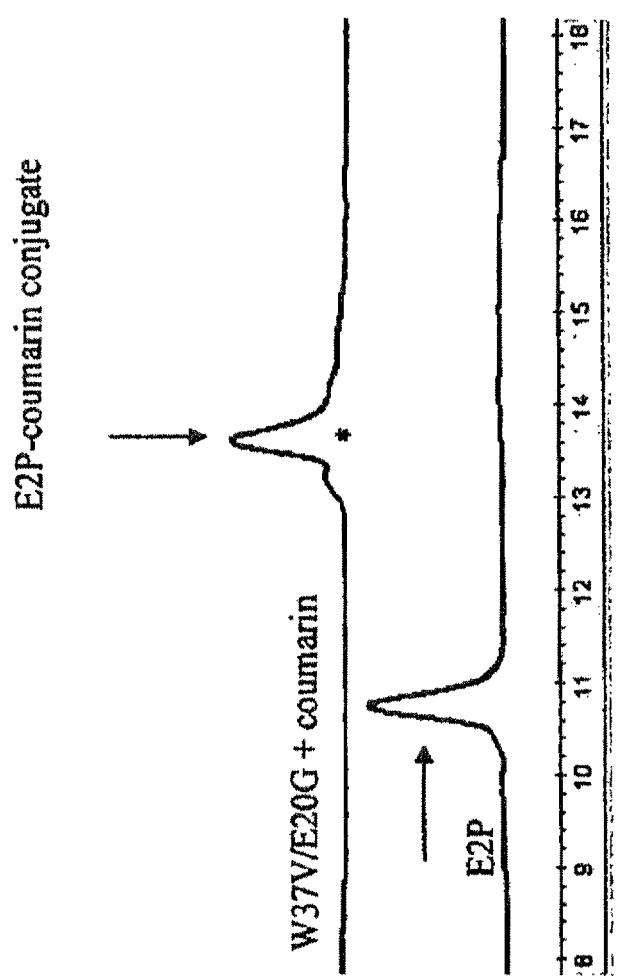
Figure 5G:
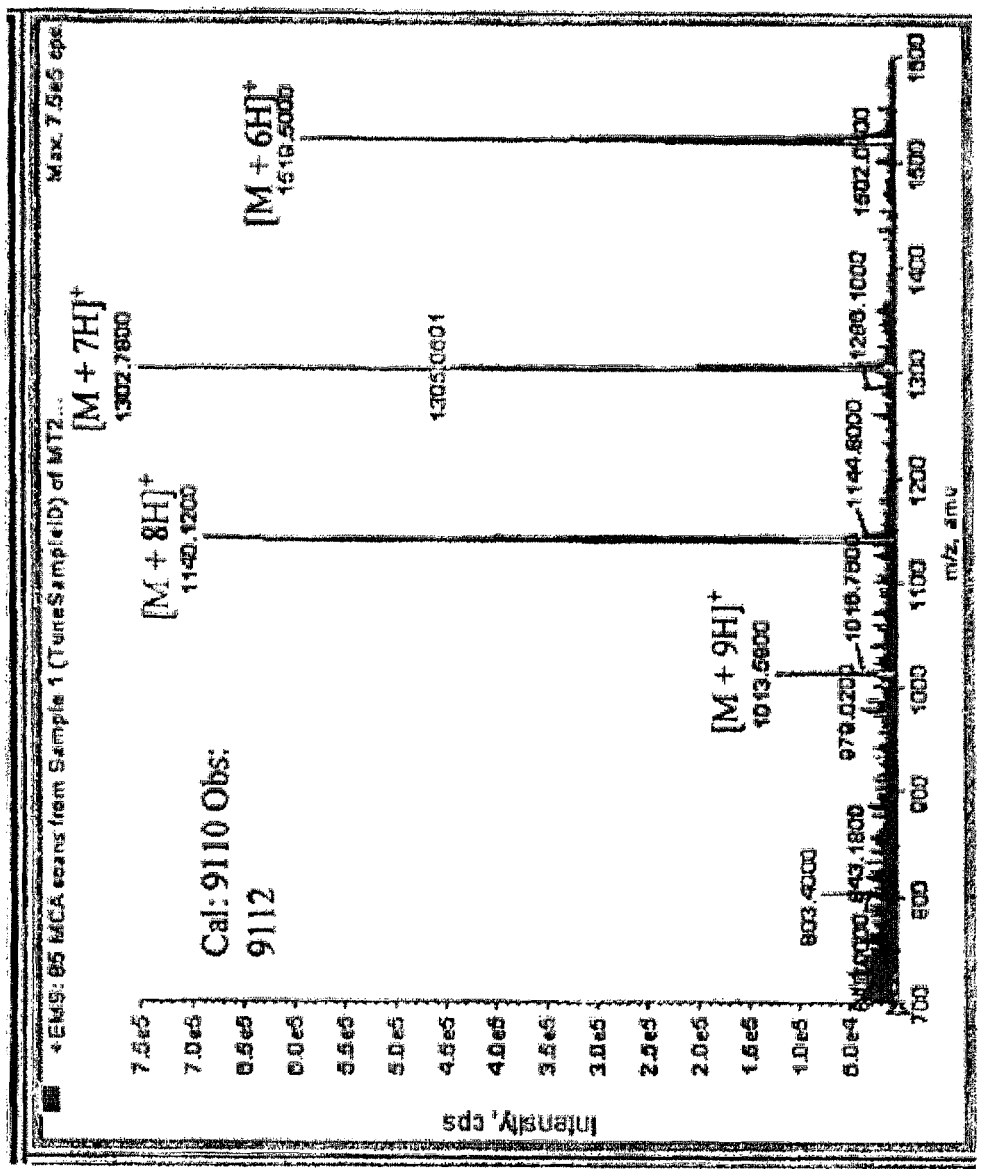

FIG. 4 provides diagrams of synthetic routes to cyclooctyne-probe conjugates. FIG. 4A shows OCT acid 1(5) was activated as the pentafluorophenyl (PFP) ester 2, then conjugated to a diamino polyethylene glycol (PEG) linker to give OCT-PEG 3. Reaction of 3 with the activated N-hydroxy succinimidyl (NHS) esters of Cy3 or Alexa Fluor 568 gave the final fluorophore conjugates 4 and 5 (FIG. 4B). The synthesis of OCT-PEG-biotin 6 (FIG. 4B) has been described (5).

FIG. 5 shows reaction diagrams, a substrate conversion table and HPLC assay traces demonstrating re-directing LplA for site-specific protein labeling with fluorescent probes. FIG. 5A shows the natural reaction catalyzed by LplA (top), and scheme for LplA-catalyzed fluorescent tagging with unnatural probes (bottom). Instead of lipoic acid, LplA ligates an alkyl azide to a lysine sidechain within a peptide recognition sequence. The azide is then selectively functionalized with a cyclooctyne-probe conjugate (dark circle), to give a triazole adduct. FIG. 5B shows a comparison of alkyl azide and alkyne substrates of LplA. Conversions are given relative to lipoic acid, which is normalized to 100%. FIG. 5C shows results from an HPLC assay showing the ligation of the azide 7 substrate to E2p protein. The starred peak was analyzed by mass-spectrometry (see FIG. 2). FIGS. 5 D and 5E show characterization of W37V LplA mutant-catalyzed aryl azide ligation. FIG. 5D shows an HPLC assay showing the ligation of the aryl azide substrate to LAPHP1. FIG. 5E shows mass spectrometric analysis of LAPHP1-aryl azide conjugate (starred product in HPLC trace). Peaks for the +8, +9, +10, +11, +12, +13, +14, and +15 charge states were observed. FIGS. 5F and 5G show characterization of W37V/E20G Lpl mutant-catalyzed coumarin (a pacific blue derivative) ligation. FIG. 5F shows an HPLC assay showing the ligation of the coumarin to LAPHP1. FIG. 5G shows mass spectrometric analysis of E2p-coumarin conjugate (starred product in HPLC trace). Peaks for the +6, +7, +8, and +9 charge states were observed.

Figure 6:
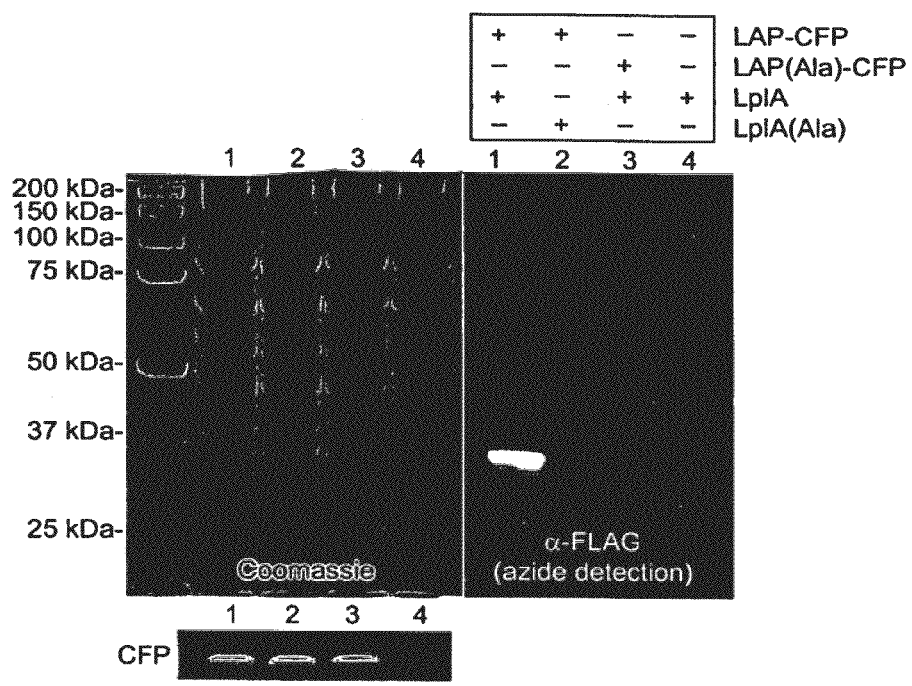

FIG. 6 shows western blots demonstrating that LplA labels the LAP peptide without modifying endogenous mammalian proteins. Lysates from HEK cells expressing a LAP fusion to CFP were labeled in vitro with LplA and azide 7. The azide was derivatized with phosphine-FLAG via the Staudinger ligation (14), and the FLAG epitope was detected by blotting with an anti-FLAG antibody. Controls are shown with LAP-CFP replaced by its alanine point mutant (lane 3), or with LplA replaced by its catalytically inactive Lys133Ala mutant (lane 2). Coomassie staining demonstrates equal loading in all lanes. Fluorescence visualization of CFP demonstrates equal expression levels of the LAP fusion in lanes 1-3.

Figure 7:
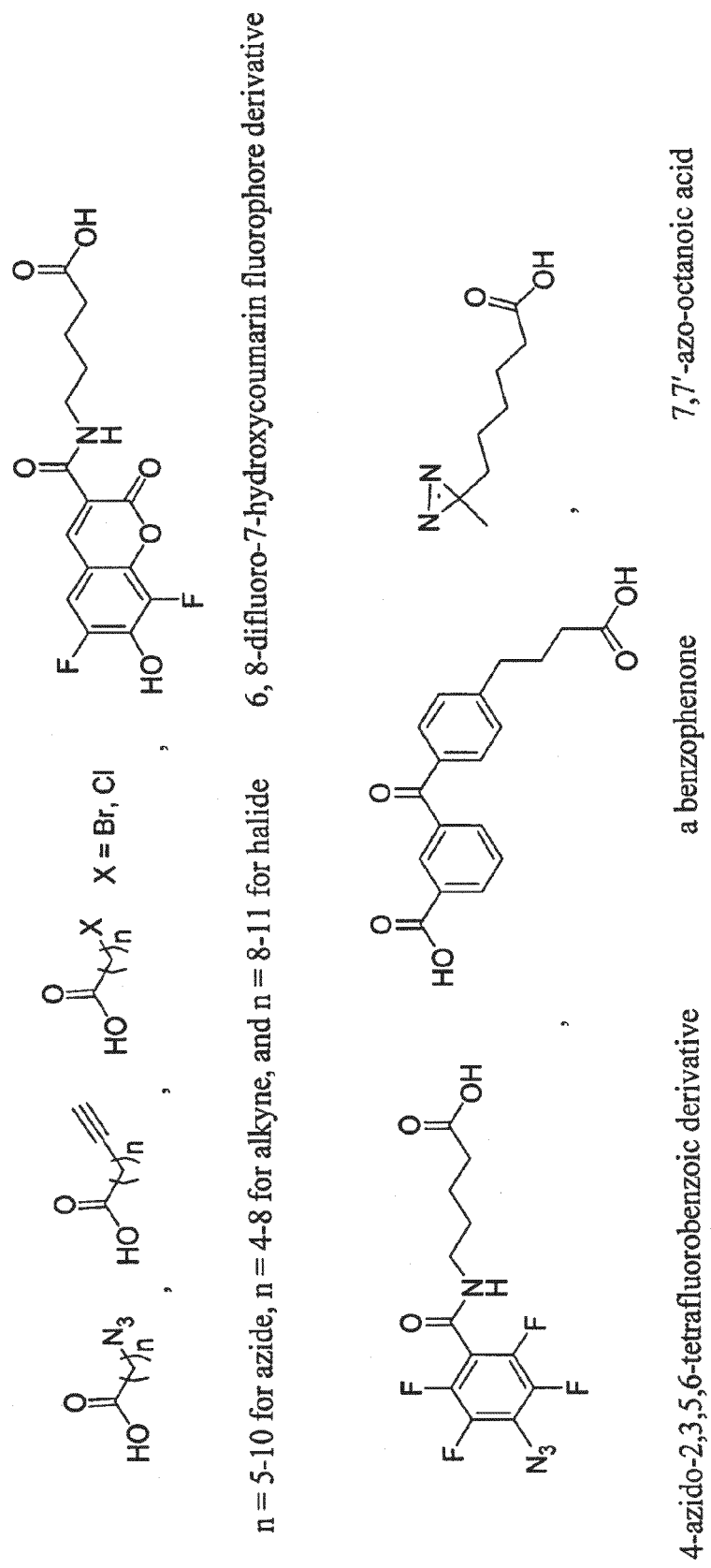

FIG. 7 shows examples of synthetic structures of substrate analogs that may be used by Lpl1 including: an alkyl azide; an alkyne; a halide; a 4-azido-2,3,5,6-tetrafluorobenzoic derivative; a 7,7'-azo-octanoic acid; a benzophenone; and a 6,8-difluoro-7-hydroxycoumarin fluorophore derivative.

Figure 8:
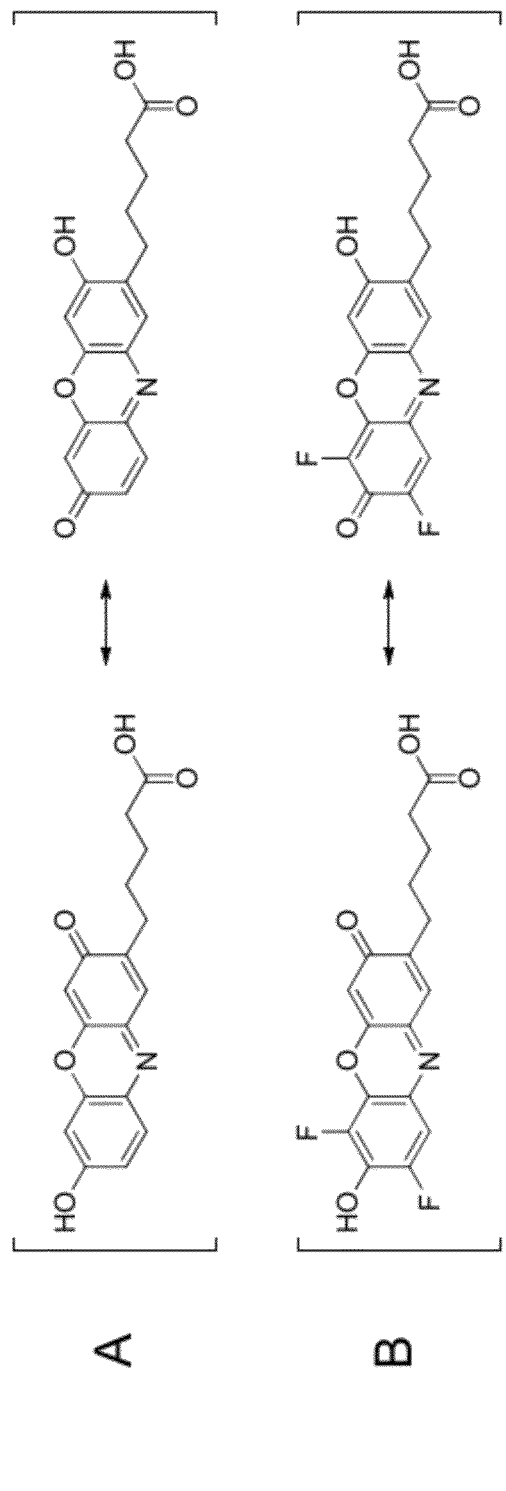
Figure 8:
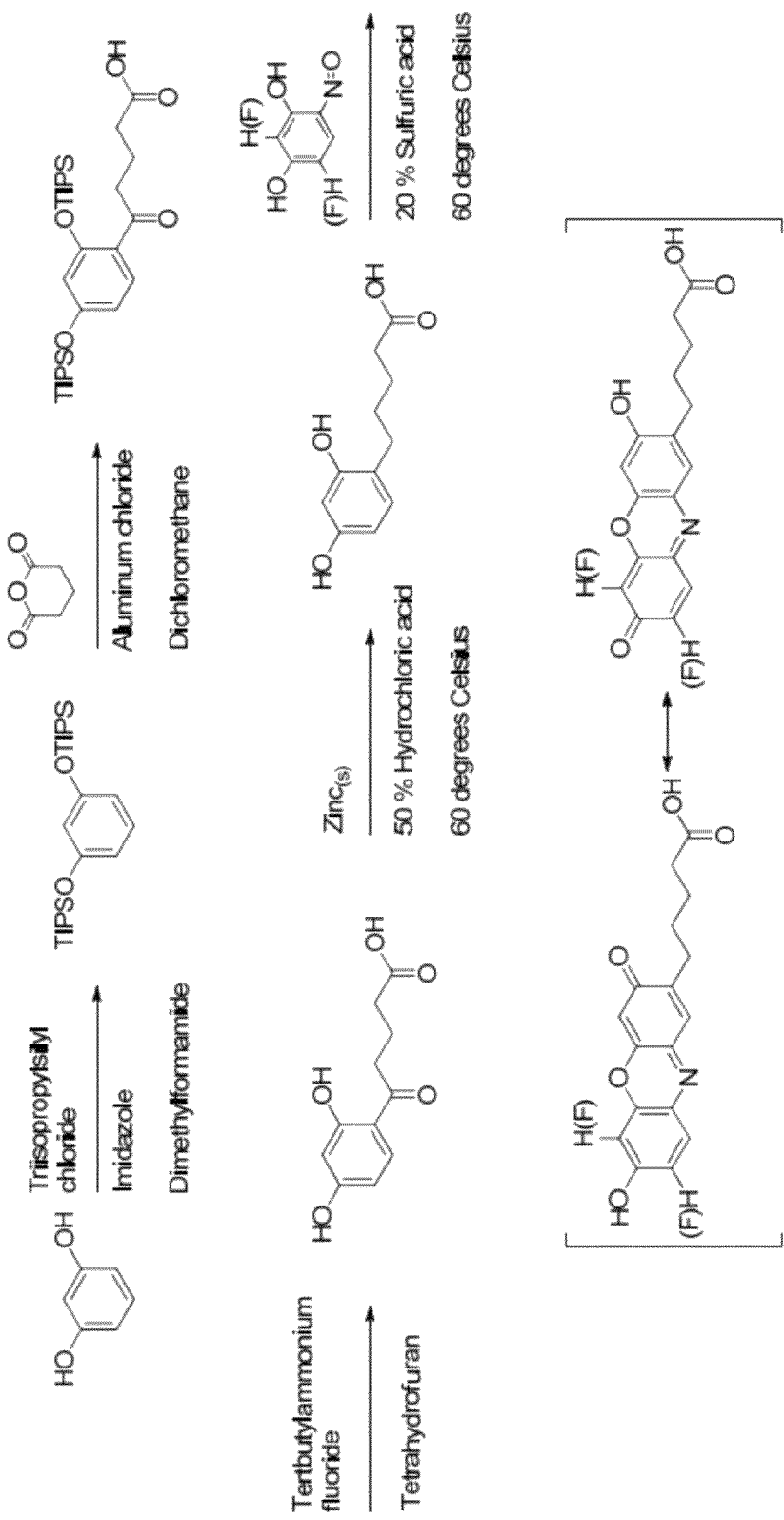

FIG. 8 is a schematic illustration showing a synthetic scheme for preparing a resorufin-containing lipoic acid analog. A: structures of resorufins A and B. B: Synthetic scheme for preparing resorufins A and B.

Figure 9:
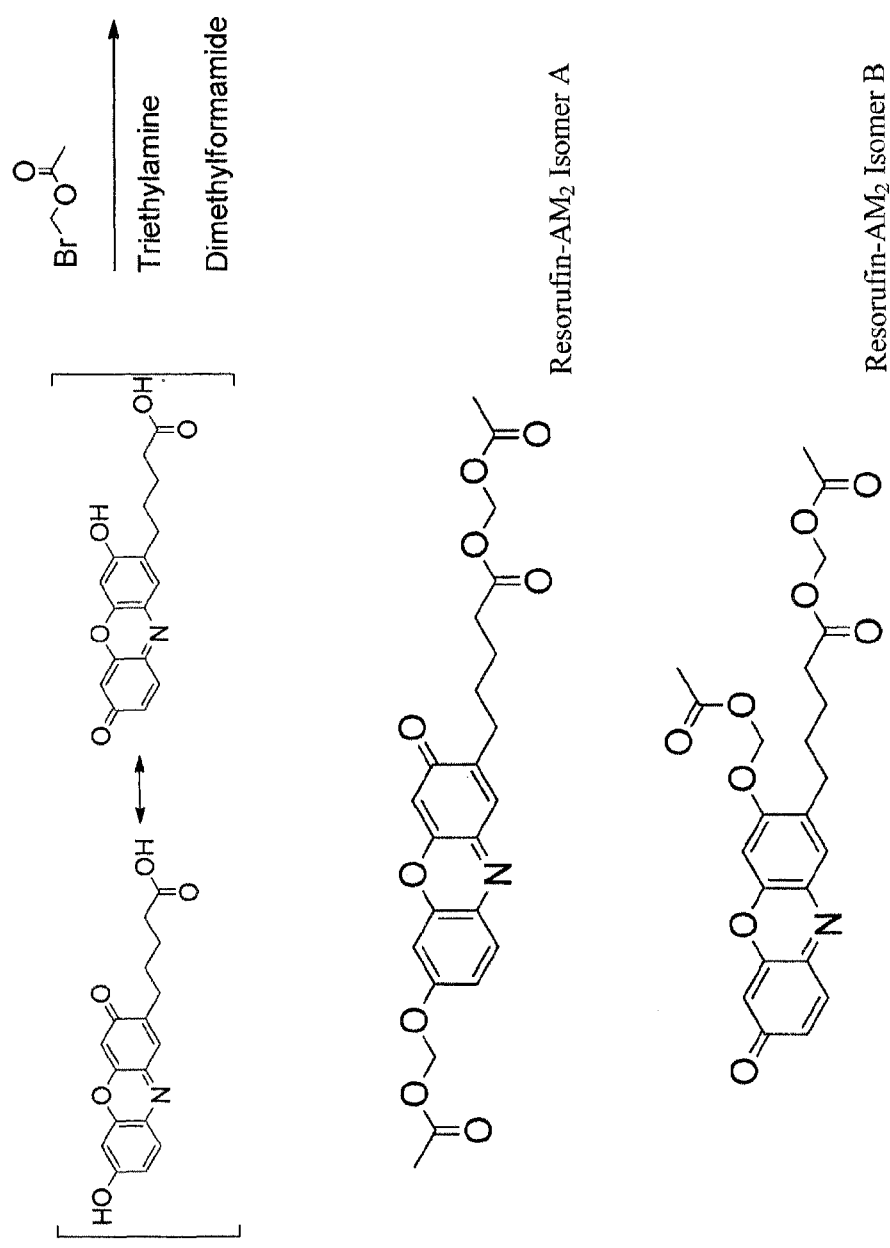

FIG. 9 is a schematic illustration showing a synthetic scheme for preparing isomers a and b of resorufin-$AM_2$.

FIG. 10 is a schematic illustration for interaction-dependent PRIME (ID-PRIME) and kinetic parameters. (a) Interaction between proteins A and B promotes probe ligation to the fused peptide (LAP), catalyzed by the fused ligase enzyme (LplA). In the absence of an interaction, no ligation occurs. (b) Summary of kinetic parameters from previous studies and this work. Rate constants relevant to proximity biotinylation are shaded red4. Rate constants relevant to LplA ligation are shaded blue5, 7-8. BirA is E. coli biotin ligase, and AP is its 15-amino acid acceptor peptide. AP(−3) is a truncated AP with 3 amino acids removed from the C-terminus4. The low affinity LAP sequence (LAP1) used for ID-PRIME is DEVLVEIETDKAVLEVP (SEQ ID NO:8). Fernandez-Suarez et al., Nat Biotechnol 2007, 25 (12), 1483-7. The high affinity LAP sequence (LAP2) used for conventional PRIME is GFEIDKVWYDLDA (SEQ ID NO:32). Puthenveetil et al. J Am Chem Soc 2009, 131 (45), 16430-8.8. The lysine site labeled by the enzyme is underlined.

Figure 11:
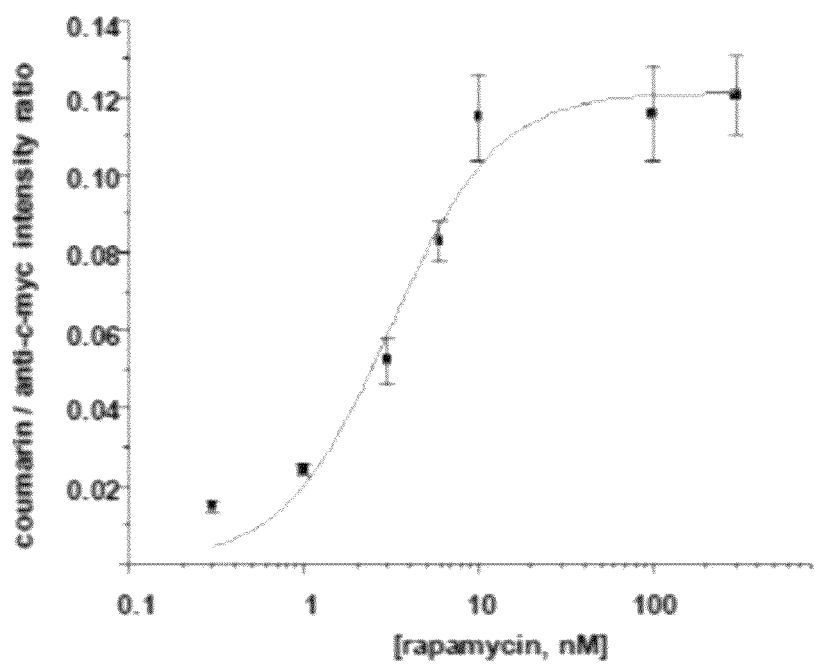

FIG. 11 is a chart showing rapamycin dose-dependent curve. HEK cells co-expressing FKBP-LAP1 and FRB-LplAW37V were incubated with varying concentrations of rapamycin for 1 hr, then labeled with coumarin-$AM_2$ for 10 min. After fixation, total FKBP-LAP1 was detected with anti-c-myc antibody. The graph shows the mean coumarin/anti-c-myc intensity ratio for 8-25 cells from at least 3 fields of view for each condition. Error bars, ±s.e.m. Scale bars, 10 μm.

DETAILED DESCRIPTION OF THE INVENTION

The invention relates to protein labeling in vivo and in vitro. Prior attempts to label specific proteins have been frustrated by a lack of reagents with sufficient specificity. The invention aims to overcome this lack of specificity through the use of lipoic acid ligase and mutants thereof with lipoic acid analogs and acceptor polypeptides that are recognized by lipoic acid ligase and mutants thereof. The invention includes, in part, use of a lipoic acid ligase to site-specifically and covalently attach small molecules to proteins modified by a short peptide tag.

The invention therefore provides, inter alia, methods for labeling proteins in vitro or in vivo. The method generally involves contacting a lipoic acid analog with a fusion protein comprising an acceptor polypeptide in the presence of a lipoic ligase mutant, and allowing sufficient time for conjugation of the lipoic acid analog to the fusion protein. Times and reaction conditions suitable for mutant lipoic acid ligase activity will generally be comparable to those for wild-type lipoic acid ligase which are known in the art. (See for example, Examples 1 and 2 herein).

The various components of this reaction will be described in greater detail herein. Briefly, the fusion protein is a fusion of the target protein (i.e., the protein which is to be labeled) and an acceptor polypeptide (i.e., the peptide sequence that acts as a substrate for the lipoic acid ligase mutant). If the method is performed in vivo, the nucleic acid sequence encoding the fusion protein may be introduced into the cell and transcription and translation allowed to occur. In some embodiments, the fusion protein may be present in a cell in a subject. In some embodiments, the fusion protein may be present in a transgenic subject. If the method is performed in vitro, the fusion protein may simply be added to the reaction mixture.

As used herein, protein labeling in vitro means labeling of a protein in a cell free environment. As an example, such a protein can be combined with a lipoic acid ligase mutant and a lipoic acid analog under appropriate conditions and thereby labeled, in for example a test tube or a well of a multiwell plate.

As used herein, protein labeling in vivo means labeling of a protein in the context of a cell. The method can be used to label proteins that are intracellular proteins or cell surface proteins. The cell may be present in a subject (e.g., an insect such as *Drosophila*, a rodent such as a mouse, a human, and the like) or it may be present in culture. In some embodiments, a subject may be a transgenic subject.

A lipoic acid ligase or mutant thereof may also be expressed by the cell in some instances. In other instances, however, the lipoic acid ligase or mutant thereof may simply be added to the reaction mixture (if in vitro) or to the cell (if the target protein is a cell surface protein and the acceptor peptide is located on the extracellular domain of the target protein).

According to the method, the lipoic acid ligase or mutant thereof conjugates the lipoic acid analog to the acceptor polypeptide that is fused (either at the nucleic acid level or post-translationally) to the target protein. The method is independent of the protein type and thus any protein can be labeled in this manner. The product of this labeling reaction may or may not be directly detectable however depending upon the nature of the lipoic acid analog, as described herein. Accordingly, it may be necessary to react the conjugated lipoic acid analog with a detectable label. If the method is performed in vivo, the detectable label may be one capable of diffusion into a cell. If the method is used to label a cell surface protein, then the lipoic acid analog may be labeled with a membrane impermeant label in order to reduce entry and accumulation of the label intracellularly. The lipoic acid analog may be labeled prior to or after conjugation to the fusion protein.

Labeling of proteins allows one to track the movement and activity of such proteins. It also allows cells expressing such proteins to be tracked and imaged, as the case may be. The methods can be used in cells from virtually any organism including insect, yeast, frog, worm, fish, rodent, human and the like.

The method can be used to label virtually any protein. Examples include but are not limited to signal transduction proteins (e.g., cell surface receptors, kinases, adapter proteins), nuclear proteins (transcription factors, histones), mitochondrial proteins (cytochromes, transcription factors) and hormone receptors.

Lipoic acid ligase is an enzyme that catalyzes the ATP-dependent ligation of the small molecule lipoic acid to a specific lysine sidechain within one of three natural acceptor proteins E2p, E2o, and H-protein. As used herein, wild-type lipoic acid ligase refers to a naturally occurring *E. coli* lipoic acid ligase having wild-type lipoic acid ligase activity, or to a homolog thereof. SEQ ID NO:11 represents the amino acid sequence of *E. coli* wild-type lipoic acid ligase. The amino acid sequence of SEQ ID NO:11 is based on the crystal structure of the wild-type LplA, which differs from the GenBank sequence set forth as Accession No. AAA21740, because the first amino-acid (methionine) has been cleaved. SEQ ID NO:11 is missing the initial methionine in the amino acid sequence set forth as Accession No. AAA21740 and therefore the amino acid numbering set forth of wild-type lipoic acid and used to identify substituted amino acid residues in modified/mutant lipoic acid ligases of the invention, differs by one amino acid from the numbering of the amino acids in Accession No. AAA21740. Numbering of amino acids of wild-type lipoic acid of the invention as used herein corresponds to the numbering of SEQ ID NO:11. Those of ordinary skill in the art will be readily able to convert the numbering of amino acids based on SEQ ID NO:11 with those of GenBank Accession No. AAA21740. SEQ ID NO: 12 represents the nucleotide sequence of *E. coli* wild-type lipoic acid ligase (GenBank Accession No. L27665).

Lipoic acid ligase is also known as lipoate-protein ligase A, LplA, and lipoate-protein ligase. In some embodiments of the invention, the lipoic acid ligase is an *E. coli* lipoic acid ligase, such as LplA. Homologs of *E. coli* lipoic acid ligase include, but are not limited to: *Thermoplasma acidophilum* LplA; *Plasmodium falciparum* LipL1, or LipL2; *Oryza Sativa* LplA (rice); *Streptococcus pneumoniae* LplA; and homologs from *Pyrococcus horikoshii; Saccharomyces cerevisiae, Trypanosoma cruzi, Bacillus subtilis,* and *Leuconostoc mesenteroides*. Homologs of *E. coli* lipoic acid ligase as well as mutants of such homologs are useful in methods and compositions of the invention.

The reaction between wild-type lipoic acid ligase and its substrate (discussed below) is referred to as orthogonal. This means that neither the ligase nor its substrate react with any other enzyme or molecule when present either in their native environment (i.e., a bacterial cell) or more importantly for the purposes of the invention in a non-native environment (e.g., a mammalian cell). Accordingly, the invention takes advantage of the high degree of specificity that has evolved between wild-type lipoic acid ligase and its substrate. Ligation interactions of the invention may or may not be orthogonal ligation reactions, it is not required that the ligation reactions of the invention be orthogonal. The only known natural substrates in bacteria of wild-type *E. coli* lipoic acid ligase are E2p, E2o, and H-protein, which are ligated to lipoic acid by the enzyme. The natural reaction of LplA has now been redirected such that unnatural structures, dissimilar to lipoic acid, can be ligated to either the natural protein substrates or LplA, or engineered peptide substrates.

A 12-17 amino acid minimal substrate sequence encompasses a lysine lipoylation site at the tip of a sharp β-turn in the substrate (e.g., such as E2o, E2p, or H-protein). For example in *E. coli* E2o, the lysine at the tip of a sharp β-turn is the lysine that is in position 44 of *E. coli* E2o, see GenBank Accession No. AAA23898. In each of the three lipoyl domains of *E. coli* E2p, the lysines at the tip of the sharp β-turn are the lysine lipoylation sites (e.g., the lysine in position of the lipoyl hybrid domain, see ProteinDataBank Accession No. 1QJO). In *E. coli* H-protein, the lysine at the tip of a sharp β-turn is the lysine that is in position 65 of *E. coli* H-protein, see GenBank Accession No. CAA52145. Testing has shown that although accurate positioning of the target lysine within the β-turn is important for LplA recognition, the residues flanking the lysine can be varied.

As used herein, an "acceptor peptide" is a protein or peptide having an amino acid sequence that is a substrate for a lipoic acid ligase, lipoic acid ligase, or mutant thereof, a lipoic acid ligase homolog or mutant thereof (i.e., a lipoic acid ligase homolog or mutant recognizes and is capable of conjugating a lipoic acid analog or lipoic acid to the peptide). The acceptor peptide may have an amino acid sequence of $Xaa_1$ $Xaa_2$ $Xaa_3$ $Xaa_4$ $Xaa_5$ $Xaa_6$ $Xaa_7$ $Xaa_8$ $Xaa_9$ Lys $Xaa_{10}$ $Xaa_{11}$ $Xaa_{12}$ $Xaa_{13}$ $Xaa_{14}$, where $Xaa_{1-14}$ is any amino acid that results in the structure of the polypeptide suitable for use in methods and compositions of the invention. In an exemplary 15 amino acid acceptor polypeptide core sequence such as $Xaa_1$ $Xaa_2$ $Xaa_3$ $Xaa_4$ $Xaa_5$ $Xaa_6$ $Xaa_7$ $Xaa_8$ $Xaa_9$ Lys $Xaa_{10}$ $Xaa_{11}$ $Xaa_{12}$ $Xaa_{13}$ $Xaa_{14}$, amino acids $Xaa_7$, $Xaa_9$ and $Xaa_{13}$ may be highly conserved among species and in some embodiments they will be amino acids E, D, and E respectively. In addition, amino acids $Xaa_3$, $Xaa_6$, and $Xaa_{14}$ may be relatively conserved and they are hydrophobic amino acids in some embodiments may be I, V or L. In some embodiments, amino acid $Xaa_2$ may be one of D, E or Q based on sequence alignment of different species. One of ordinary skill in the art will understand how to interpret the positions of amino acids in a 15 amino acid core sequence with those in a shorter acceptor polypeptide sequence, for example in a 12, 13, or 14 amino acid acceptor polypeptide sequence, based on the position of the lysine residue in the sequences. Although the exemplary sequence $Xaa_1$ $Xaa_2$ $Xaa_3$ $Xaa_4$ $Xaa_5$ $Xaa_6$ $Xaa_7$ $Xaa_8$ $Xaa_9$ Lys $Xaa_{10}$ $Xaa_{11}$ $Xaa_{12}$ $Xaa_{13}$ $Xaa_{14}$ a 15 amino acid polypeptide, longer acceptor polypeptides and shorter acceptor polypeptides are also useful in methods and compositions of the invention. Non-limiting examples of polypeptide substrates useful in the invention are provided in FIG. 3.

In important embodiments, the acceptor peptides are low affinity peptides comprises the amino acid sequence of a polypeptide having SEQ ID NO:1, 2, 3, 4, 5, 6, 7, 8, 9, or 10, set forth in FIG. 3, or may be a variant thereof. A variant polypeptide may include a portion of an amino acid set forth herein as SEQ ID NOs: 1-10, (e.g., may be a 12, 13, or 14 amino acid portion as long as it includes the lysine residue and functions as an acceptor polypeptide), or may include the full sequence of one of SEQ ID NO:1-10 with additional amino acids attached at one or both ends of the polypeptide. As long as a polypeptide includes the positioning of the target lysine within the β-turn such that the polypeptide functions as a substrate for lipoic acid enzyme as described herein, (e.g., wild-type, homolog, and/or mutants thereof) the remainder of the polypeptide sequence can vary.

In some embodiments of the invention, an acceptor polypeptide that functions as a substrate for a lipoic acid ligase or mutant thereof includes an amino acid sequence of SEQ ID NO:1, 2, 3, 4, 5, 6, 7, 8, 9, or 10, or a functional variant thereof. A functional variant of an acceptor polypeptide may include an amino acid sequence that has up to 85%, 90%, 95%, or 99% identity to at least one of SEQ ID NOs: 1, 2, 3, 4, 5, 6, 7, 8, 9, or 10 and is a substrate for a lipoic acid ligase or mutant thereof. In some embodiments, an acceptor polypeptide includes the amino acid sequence of SEQ ID NO: 8 or 10. An acceptor polypeptide may be N- or C-terminally fused to a target protein. One of ordinary skill in the art will understand how the amino acid sequence can be varied and how to vary the sequence such that it functions as an acceptor polypeptide for the methods and compositions of the invention. Acceptor peptides can be synthesized using standard peptide synthesis techniques. One of ordinary skill in the art will also recognize how to prepare an acceptor polypeptide such that is it attached (fused) to a target protein using routine methods.

Alternatively, the acceptor polypeptides described herein are high affinity peptides, e.g., those described in US20110130348, which is herein incorporated by reference. Such high affinity acceptor polypeptides can have a $k_{cat}$ value in the range of 0.001 $s^{-1}$-1.0 $s^{-1}$ (e.g., approximately 0.22±0.01 $s^{-1}$) and/or a $K_m$ value in the range of 1 μM-500 μM (e.g., approximately 13.32±1.78 μM), and/or a $k_{cat}/K_m$ ratio in the range of 0.0001-10 $μM^{-1}$ $min^{-1}$. Such acceptor polypeptide can have a length ranging from 8-13 amino acids.

The just-noted acceptor polypeptides have a conserved central lysine residue at position 0, but can have varying flanking residues. In some embodiments, the residue at position +1 is hydrophobic. For example, the residue at position +1 can be valine, isoleucine, leucine or phenylalanine. In other embodiments, the residue at position +1 can be a small residue such as alanine or serine. In some embodiments, the residue at position +1 is not a charged residue. In some embodiments, the residue at position +2 position is an aromatic residue such as a tryptophan or phenylalanine residue. In some embodiments, the residue at position +3 position is an aromatic residue such as tyrosine, histidine or phenylalanine. In some embodiments, the residue at position +3 position is an aliphatic hydrophobic residue such as an isoleucine, valine, leucine or threonine residue.

In some embodiments, the residue at position +4 is a negatively charged residue such as aspartic acid or glutamic acid. In some embodiments, the residue at position +5 is an aliphatic hydrophobic residue such as leucine, isoleucine or phenylalanine. In some embodiments, the residue at position +5 is a small residue such as valine. The residue at position +6 can be any residue. In some embodiments, the residue at position +6 can be a negatively charged residue such as glutamic acid or aspartic acid. In some embodiments, the residue at position +6 is a hydroxyl/thiol containing residue such as serine, threonine, cysteine or tyrosine. In some embodiments, the residue at position +6 is a proline residue. In some embodiments there is no residue in position +7. In other embodiments there is a residue at position +7. In certain embodiments, the residue at position +7 is a serine or alanine residue.

In some embodiments the residue at position −1 is an aspartic acid, asparagine, glutamic acid, tyrosine or alanine residue. The residue at position −2 can be any residue. In some embodiments, the residue at position −2 is an isoleucine, histidine, leucine or arginine residue. In some embodiments, the residue at position −3 is a negatively charged residue such as glutamic acid or aspartic acid. In some embodiments, the residue at position −4 is a hydrophobic residue such as phenylalanine, isoleucine, valine or leucine. In some embodiments, the residue at position −4 is an aromatic residue. In some embodiments, there is no residue in position −5. In other embodiments, there is a residue in position −5. In certain embodiments, the residue at position −5 is a glycine residue. In one example, the acceptor polypeptide is GFEIDKVWYDLDA (LAP2; SEQ ID NO:32).

One of ordinary skill in the art will recognize how to identify acceptor polypeptides and how to modify acceptor polypeptides of the invention to prepare additional acceptor polypeptides that are useful in methods and compositions of the invention. Various assays can be used to test the sequence specificity of acceptor polypeptides and their suitability for mammalian cell labeling applications. A non-limiting example of a method for identifying an acceptor polypeptide includes combining a candidate acceptor polypeptide with a labeled lipoic acid or analog thereof in the presence of a lipoic acid ligase or mutant thereof and determining a level of lipoic acid or lipoic acid analog incorporation, wherein lipoic acid or lipoic acid analog incorporation is indicative of a candidate acceptor polypeptide having specificity for a lipoic acid ligase or mutant thereof.

The acceptor peptide is used in the methods of the invention to tag target proteins that are to be labeled by lipoic acid ligase and mutants thereof. The acceptor peptide and target protein may be fused to each other either at the nucleic acid or amino acid level. Recombinant DNA technology for generating fusion nucleic acids that encode both the target protein and the acceptor peptide are known in the art. Additionally, the acceptor peptide may be fused to the target protein post-translationally. Such linkages may include cleavable linkers or bonds which can be cleaved once the desired labeling is achieved. Such bonds may be cleaved by exposure to a particular pH, or energy of a certain wavelength, and the like. Cleavable linkers are known in the art. Examples include thiol-cleavable cross-linker 3,3'-dithiobis(succinimidyl propionate), amine-cleavable linkers, and succinyl-glycine spontaneously cleavable linkers.

The acceptor peptide can be fused to the target protein at any position. In some instances, it is preferred that the fusion not interfere with the activity of the target protein, accordingly, the acceptor peptide is fused to the protein at positions that do not interfere with the activity of the protein. Generally, the acceptor peptides can be C- or N-terminally fused to the target proteins. In still other instances, it is possible that the acceptor peptide is fused to the target protein at an internal position (e.g., a flexible internal loop). These proteins are then susceptible to specific tagging by lipoic acid ligase and/or mutants thereof in vivo and in vitro. This specificity is possible because neither lipoic acid ligase nor the acceptor peptide react with any other enzymes or peptides in a cell.

The invention is also directed in part to the identification and use of analogs of lipoic acid in assays and methods of the invention such as those described herein. As described herein, LplA naturally catalyzes the ATP-dependent ligation of the small-molecule lipoic acid to a specific lysine sidechain within one of three natural acceptor proteins (E2p, E2o, and. H-protein). As depicted in FIG. 5, LplA has been redirected to ligate analogs of lipoic acid, in order to label proteins with useful biophysical probes. A number of alkyl azide and alkyne LplA substrates of varying lengths have been synthesized (for example see FIG. 5B).

The alkyl azides were synthesized either by nucleophilic substitution of the corresponding bromoalkanoic acid with sodium azide, or by metal-catalyzed diazo transfer onto the amine precursor. The alkynes were synthesized from the bromoalkanoic acid precursor, by displacement with lithium acetylide. An HPLC assay has been developed to test if these, and other, substrate analogs could be used by LplA (FIG. 5C) and found that all the tested alkyl azides and alkynes were incorporated to some degree by LplA, with azides in general incorporated at a higher rate than alkynes (FIG. 5B). Among the alkyl azides a length dependence was identified, with the n=7 azide. (azide 7) displaying the best kinetics. In some embodiments of the invention, the carbon chain length of an alkyl azide (FIG. 7A) may be 5, 6, 7, 8, 9, or 10. In some embodiments, the carbon chain length of an alkyne of the invention (FIG. 7B) may be 4, 5, 6, 7, or 8. In some embodiments, the carbon chain length of an halide (FIG. 7C) of the invention may be 8, 9, 10 or 11, and in some embodiments, X=Br or Cl. As an example of characterization of ligation, kinetic characterization of the ligation of azide 7 by LplA yielded a $K_{cat}$ 0.111±0.003 s$^{-1}$ (only 2.3-fold higher than the measured $K_{cat}$ for lipoic acid ligation) and $K_m$ of 127±11 μM (75- or 30-fold higher than the two reported $K_m$ values for lipoic acid). In some embodiments, the alkyl azide is a modified alkyl azide and the alkyne carboxylic acid is a modified alkyne carboxylic acid. The following structures are non-limiting examples of core structures of lipoic acid analogs that may be used in methods and compositions of the invention. These structures may be modified to prepare lipoic acid analogs that are also useful in methods and products of the invention. Useful modifications include, but are not limited to, changing the linker between the carboxylic acid and the azide/alkyne to make it more hydrophilic, such as introduction of one or two oxi groups.

In some embodiments of the invention, a lipoic acid analog may be an aryl azide, diazirine, or benzophenone photoaffinity probe or a fluorophore substrate. A lipoic acid analog may be a 4-azido-2,3,5,6-tetrafluorobenzoic derivative (FIG. 7E), a 7,7'-azo-octanoic acid (FIG. 7G), a benzophenone (FIG. 7F) or a 6,8-difluoro-7-hydroxycoumarin fluorophore derivative (FIG. 7D). In some embodiments of the invention, the aryl azide photoaffinity probe or fluorophore substrate may be a modified aryl azide photoaffinity probe or fluorophore substrate. Modifications may include changing the length of the alkyl chain that links the carboxylic acid to the photoaffinity probe and/or fluorophore. The linker may also be modified to change its hydrophobicity properties by, for example, introducing oxi groups in the alkyl chain. Additionally, protected versions of the coumarin probe may be used in which the hydroxyl and carboxylic acid functionalities are protected with an acetate or acetoxymethylester respectively in order to render the molecule permeable to the cell membrane.

Exemplary structures of lipoic acid analogs that may be used in methods of the invention include, but are not limited to:

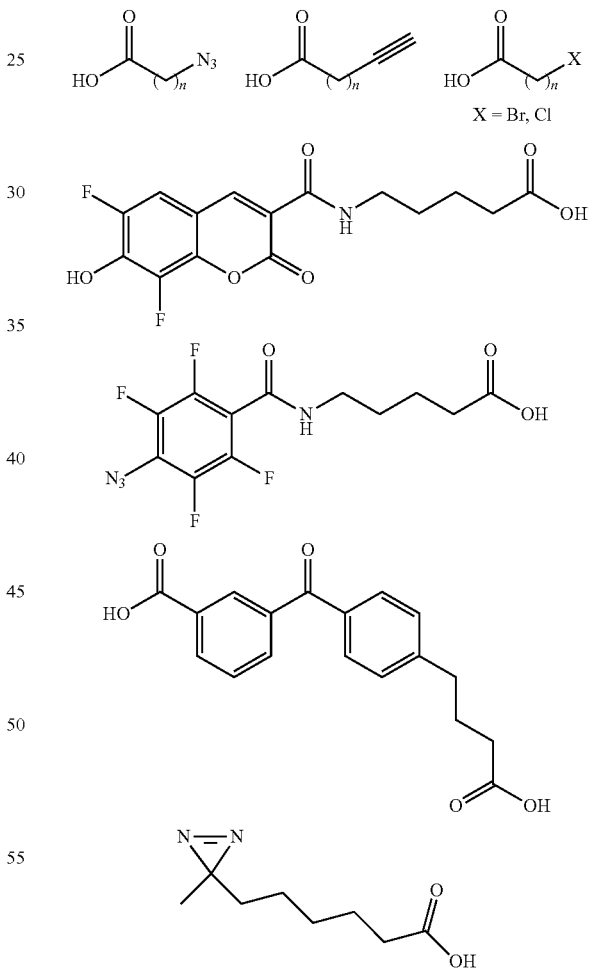

In other embodiments, a lipoic acid analog is a compound that comprises an aliphatic carboxylic acid moiety substituted with a resorufin moiety. The aliphatic carboxylic acid moiety, which is common to all lipoic acid analogs, can be an alkyl carboxylic acid, an alkenyl carboxylic acid, or alkynyl carboxylic acid. The resorufin moiety has a core structure of:

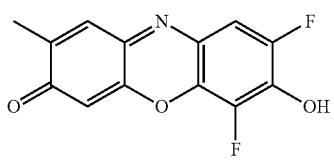 [SMILES: Cc1cc2nc3cc(F)c(O)c(F)c3oc-2cc1=O]

Both the aliphatic carboxylic acid moiety and the resorufin moiety can be either substituted or unsubstituted. Examples of substituents include, but are not limited to, halo, hydroxy, amino, cyano, nitro, mercapto, alkoxycarbonyl, amido, alkanesulfonyl, alkylcarbonyl, carbamido, carbamyl, carboxy, thioureido, thiocyanato, sulfonamido, alkyl, alkenyl, alkynyl, alkyloxy, aryl, heteroaryl, cyclyl, and heterocyclyl.

In one example, the aliphatic carboxylic acid moiety is linked directly to a resorufin moiety, e.g., one carbon atom such as the terminal carbon atom being linked with the resorufin moiety directly. Examples of resorufin-containing lipoic acid analogs include, but are not limited to, resorufins A and B shown in FIG. 8, which can be either unsubstituted or substituted. Substituted resorufins A and B can be resorufin-$AM_2$, including isomer a and isomer b (see FIG. 9).

Alternatively, the resorufin moiety can be linked with the aliphatic carboxylic acid moiety via a linker.

One of ordinary skill in the art will recognize how to modify lipoic acid analogs of the invention to prepare additional lipoic acid analogs that are useful in methods and compositions of the invention. Various assays can be used to test the sequence specificity of LplA, and the suitability of various lipoic acid analogs and acceptor polypeptides for mammalian cell labeling applications. A non-limiting example of a method for identifying a lipoic acid analog having specificity for a lipoic acid ligase or a mutant includes combining an acceptor polypeptide with a candidate lipoic acid analog molecule in the presence of a lipoic acid ligase or mutant thereof and determining the presence of lipoic acid analog incorporation, wherein lipoic acid analog incorporation is indicative of a candidate lipoic acid analog having specificity for a lipoic acid ligase or mutant thereof. Additional exemplary assays and methods of determining the presence of lipoic acid incorporation are provided in the Examples section herein.

In some aspects of the invention, an azide group that has been attached to the target can be selectively derivatized to any fluorescent probe conjugated to a cyclooctyne reaction partner. The azide group is thus useful as a "functional group handle." Direct ligation of a fluorophore may be used as a labeling procedure, but incorporation of a "functional group handle" is more feasible due to the small size of the lipoate binding pocket, and provides greater versatility for subsequent incorporation of probes of any structure. Many functional group handles have been used in chemical biology, including ketones, organic azides, and alkynes (Prescher, J. A. & Bertozzi, C. R. 2005 *Nat. Chem. Biol.* 1, 13-21). Organic azides are suitable for live cell applications, because the azide group is both abiotic and non-toxic in animals and can be selectively derivatized under physiological conditions (without any added metals or cofactors) with cyclooctynes, which are also unnatural (Agard, N. J., et. al., 2006 *ACS Chem. Biol.* 1, 644-648). Methods of using functional group handles such as azides and alkynes are well known in the art and methods and procedures for the use of such functional group handles in combination with a cyclooctyne reaction a partner are understood and can be practiced by those of ordinary skill in the art using routine techniques.

Any of the lipoic acid analogs can be synthesized by chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Exemplary synthetic schemes for preparing a number of lipoic acid analogs are provided in FIGS. 1, 2, and 8.

The invention is directed in part to generating lipoic acid ligase mutants that recognize lipoic acid analogs and conjugate such analogs to the acceptor peptide. Lipoic acid ligase mutants can be generated in any number of ways, including in vitro compartmentalization, genetic selections, yeast display, or FACS in mammalian cells, described in greater detail herein, all of which are standard methods understood and routinely practiced by those of ordinary skill in the art.

Labeling methods of the invention rely on the activity of lipoic acid ligase and mutants thereof that recognize and conjugate lipoic acid analogs onto fusion proteins via the acceptor peptide. The invention provides lipoic acid ligase mutants that recognize lipoic acid analogs. As used herein, a lipoic acid ligase mutant is a variant of lipoic acid ligase that is enzymatically active towards a lipoic acid analog (such as those described herein). As used herein, "enzymatically active" means that the mutant is able to recognize and conjugate a lipoic acid analog to the acceptor peptide.

A lipoic acid ligase mutant of the invention can have various mutations, including addition, deletion or substitution of one or more amino acids. Preferably, the mutation will be present in the lipoic acid interaction and activation region, spanning amino acids 16-149. Generally, these mutants will possess one or more amino acid substitutions relative to the wild-type lipoic acid ligase amino acid sequence (SEQ ID NO:11). In most instances, the lipoic acid ligase mutants do not comprise an amino acid substitution (or other form of mutation) of the lysine that corresponds to lysine 133 of the wild-type *E. coli* lipoic acid ligase set forth as SEQ ID NO:11 (which is the putative catalytic residue).

Some mutants were developed based on an analysis of the lipoic acid binding site of wild-type lipoic acid ligase. Residues that appear important in the interaction with lipoic acid and/or lipoic acid analogs of the invention include nucleic acids that correspond to: N16, L17, V19, E20, E21, W37, F35, N41, R70, S71A, S72, H79, C85, T87, R140, F147, and H149 or wild-type *E. coli* lipoic acid ligase set forth as SEQ ID NO:11. Residues of wild-type *E. coli* lipoic acid ligase (set forth as SEQ ID NO:11) that influence lipoic acid or analog affinity include N16, L17, V19, E20, E21, W37, F35, N41, R70, S71A, S72, H79, C85, T87, R140, F147, and H149 (and the corresponding amino acid residues in ligases of the invention). In some important embodiments of the invention, mutants comprise amino acid substitutions at one or more of the positions that correspond to: N16, L17, V19, E20, E21, W37, W37+S71, W37+E20, W37+F35, F35, N41, R70, S71, S72, H79, C85, T87, R140, F147, and H149 of wild-type *E. coli* lipoic acid ligase set forth as SEQ ID NO:11. Specific examples of lipoic acid ligase mutants are proteins having at least one of the amino acid substitution that corresponds to: N16A, L17A, V19A, E20A, E21A, W37A, W37G, W37S, W37V, W37A +S71A, W37A+E20A, W37L, W37I, W37T, W37N, W37V+E20G, W37V+F35A, W37V +E20A, F35A, N41A, R70A, S71A, S72A, H79A, C85A, T87A, R140A, F147A, H149A, and H149V of wild-type *E. coli* lipoic acid ligase set forth as SEQ ID NO:11. The invention contemplates the use of lipoic acid ligase mutants having an amino acid substitution at one or more of the aforementioned positions. Of particular importance in some embodiments, are lipoic acid ligase mutants that harbor amino acid substitutions at positions that correspond to E20, F35, W37, S71, H79, F147 and H149 of SEQ ID NO:11. Examples include but are not limited to substitutions that correspond to E20A, W37A, W37G, W37S, W37V, W37L, W37N, W37I, W37T, W37V+ E20G, W37V+E20A and W37V+F35A of SEQ ID NO:11.

In some embodiments, the lipoic acid ligase mutant disclosed herein includes mutations at residues corresponding to E20, F147, and optionally H149. For example, Both E20 and F147 can be replaced with Ala or a conservative amino acid substitution thereof and H149 can be replaced with Gly or a conservative amino acid substitution thereof. Such lipoic acid ligase mutants are capable of catalyzing conjugation of a lipoic acid analog that contains a resorufin moiety to a target protein via an acceptor polypeptide. Examples of the lipoic acid ligase mutants specific to resorufin include, but are not limited to, double-mutant E20A+F147A and triple-mutant E20A+F147A+H149G.

A lipoic acid ligase mutant may retain some level of activity for lipoic acid or an analog thereof. Its binding affinity for lipoic acid or an analog thereof may be similar to that of wild-type lipoic acid ligase. Preferably, the mutant has higher binding affinity for a lipoic acid analog than it does for lipoic acid. Consequently, lipoic acid conjugation to an acceptor peptide would be lower in the presence of a lipoic acid analog. In still other embodiments, the lipoic acid ligase mutant has no binding affinity for lipoic acid.

In some embodiments of the invention, a lipoic acid ligase analog may have a nucleic acid sequence that has up to 85%, 90%, 95%, or 99% identity to the nucleic acid sequence of a wild-type lipoic acid ligase and ligates lipoic acid and/or a lipoic acid analog to an acceptor polypeptide. A lipoic acid ligase analog (mutant) may include an amino acid sequence that has up 85%, 90%, 95%, or 99% identity to the amino acid sequence of wild-type E. coli lipoic acid ligase (e.g., to SEQ ID NO:11) and will retain function as a lipoic acid ligase in methods of the invention. In some embodiments, a lipoic acid ligase used in methods of the invention is the lipoic acid ligase having the sequence set forth as SEQ ID NO:11.

One of ordinary skill in the art will recognize how to identify suitable lipoic acid ligases and how to modify lipoic acid ligases of the invention to prepare additional lipoic acid ligases that are useful in methods and compositions of the invention. Various assays can be used to test the specificity and functionality of a lipoic acid ligase and its suitability for mammalian cell labeling applications. A non-limiting example of a method for identifying a lipoic acid ligase includes contacting a lipoic acid or lipoic acid analog with an acceptor polypeptide in the presence of a candidate lipoic acid ligase molecule, and detecting a lipoic acid or lipoic acid analog that is bound to the acceptor polypeptide, wherein the presence of a lipoic acid or lipoic acid analog bound to an acceptor polypeptide indicates that the candidate lipoic acid ligase molecule is a lipoic acid ligase that has specificity for the lipoic acid or lipoic acid analog.

To conjugate a lipoic acid analog to a protein of interest, the analog is in contact with a fusion protein containing the protein of interest and a suitable acceptor polypeptide in the presence of a suitable lipoic acid ligase polypeptide under conditions allowing a lipoic acid ligase reaction to take place. The lipoic acid ligase polypeptide can be a naturally-occurring lipoic acid ligase or a mutant thereof with desired substrate specificity, i.e., recognizing both the acceptor polypeptide and the lipoic acid analog.

In one example, this conjugation reaction is carried out in vitro. Conditions for in vitro lipoic acid ligase reactions are well known in the art, e.g., those described in the Examples below. Lipoic acid analog incorporation can be measured using $^3$H-lipoic acid and measuring incorporation of radioisotope in the peptide. Conjugation of the lipoic acid analog to an acceptor peptide can be assayed by various methods including, but not limited to, HPLC or mass-spec assays, as described herein and as shown in the figures herein.

Alternatively, the conjugation reaction is carried out in vivo. Briefly, expression vectors for producing the above-noted fusion protein and the lipoic acid ligase polypeptide are introduced into cells via routine recombinant technology. The transformed cells are cultured under suitable conditions in the presence of the lipoic acid analog, which preferably can be detected directly, e.g., containing a fluororescent moiety such as the coumarin and resorufin analogs described herein. The cells are then washed to remove free lipoic acid analogs. Conjugation of the lipoic acid analog to the fusion protein can then be examined via routine technology, e.g., fluorescent microscopy. See the Examples below.

The skilled artisan will realize that conservative amino acid substitutions may be made in lipoic acid ligase mutants to provide functionally equivalent variants, i.e., the variants retain the functional capabilities of the particular lipoic acid ligase mutant. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of lipoic acid ligase mutants to produce functionally equivalent variants typically are made by alteration of a nucleic acid encoding the mutant. Such substitutions can be made by a variety of methods known to one of ordinary skill in the art. For example, amino acid substitutions may be made by PCR-directed mutation, site-directed mutagenesis according to the method of Kunkel (Kunkel, PNAS 82: 488-492, 1985), or by chemical synthesis of a nucleic acid molecule encoding a lipoic acid ligase mutant.

Similarly, lipoic acid ligase mutants can be made using standard molecular biology techniques known to those of ordinary skill in the art. For example, the mutants may be formed by transcription and translation from a nucleic acid sequence encoding the mutant. Such nucleic acid sequences can be made based on the teaching of wild-type lipoic acid ligase sequence and the position and type of amino acid substitution.

The invention further provides methods for screening candidate molecules for activity as a lipoic acid ligase mutant. These screening methods can also be combined with methods for generating candidates. Exemplary methods include, but are not limited to, in vitro compartmentalization, life/death selections in bacteria, yeast display, or FACS in mammalian cells, each of which is known and routinely used by those of ordinary skill in the art. In vitro compartmentalization (IVC) selection strategy provides a platform to conduct multiple turnover selection for enzymes. In this completely in vitro system genes are compartmentalized by forming a water-in-oil emulsion. In this water-in-oil emulsion compartment genotype-phenotype linkage is maintained through out the entire process from transcription/translation to substrate to product formation. The main advantage of IVC over other traditional methods of selection is its ability to select out faster enzymes from slower enzymes.

The following is an example of a genetic selection strategy that may be used to evolve lipoic acid ligase mutants. In the method, the selection is based on an E. coli strain with knock out LplA and LipB gene. This allows the strain to grow only in presence of succinate plus acetate or by introducing a functional LplA mutant that recognizes exogenous lipoic acid as its substrate. For selection an LplA mutant library may be transformed to this strain and will allow it to grow in presence of a suitable molar ratio of lipoic acid and its analog. Mutants that recognize lipoic acid will grow but mutants that do not recognize lipoic acid will cease to grow. β-lactam-based antibiotic will selectively kill the dividing bacteria (carrying mutants that are not of interest). The remaining static pool of bacteria (carrying LplA mutants that are of interest) are harvested and used for successive round of selections.

The labeling methods of the invention further rely on lipoic acid analogs that are recognized and conjugated to acceptor peptides by lipoic acid ligase mutants. As used herein, a lipoic acid analog is a molecule that may be structurally similar to lipoic acid. Lipoic acid analogs may share one particular structural feature in common with lipoic acid. A lipoic acid analog may be synthesized from lipoic acid, but is not so limited. Examples of lipoic acid analogs include, but are not limited to, an alkyl azide, an alkyne carboxylic acid, an aryl azide photoaffinity probe, a fluorophore (coumarin) substrate, a modified alkyl azide, a modified alkyne, a carboxylic acid, a 4-azido-2,3,5,6-tetrafluorobenzoic derivative, a 7,7'-azo-octanoic acid, a benzophenone, or a 6,8-difluoro-7-hydroxycoumarin fluorophore derivative (see FIG. 7 for exemplary derivatives).

The lipoic acid ligase mutants must be capable of recognizing and conjugating lipoic acid analogs to acceptor peptides, in a manner similar to that in which wild-type lipoic acid ligase recognizes and conjugates lipoic acid to the acceptor peptide.

The lipoic acid analog binds to a lipoic acid ligase mutant and it preferably binds with an affinity comparable to the binding affinity of wild-type lipoic acid ligase to lipoic acid. However, lipoic acid analogs that bind with lower affinities are still useful according to the invention. In some embodiments, the lipoic acid analog is not recognized by wild-type lipoic acid ligase derived from either E. coli or from other cell types (e.g., the cell in which the labeling reaction is proceeding).

Some lipoic acid analogs are not themselves directly detectable, while others are. In the case of the former type, the lipoic acid analog undergoes reaction with another moiety (after conjugation to the acceptor peptide). The subsequent modification of this former type of lipoic acid analog is referred to as a bio-orthogonal ligation reaction and it is used to couple (i.e., label) these lipoic acid analogs to detectable labels such as fluorophores.

Figure 1:
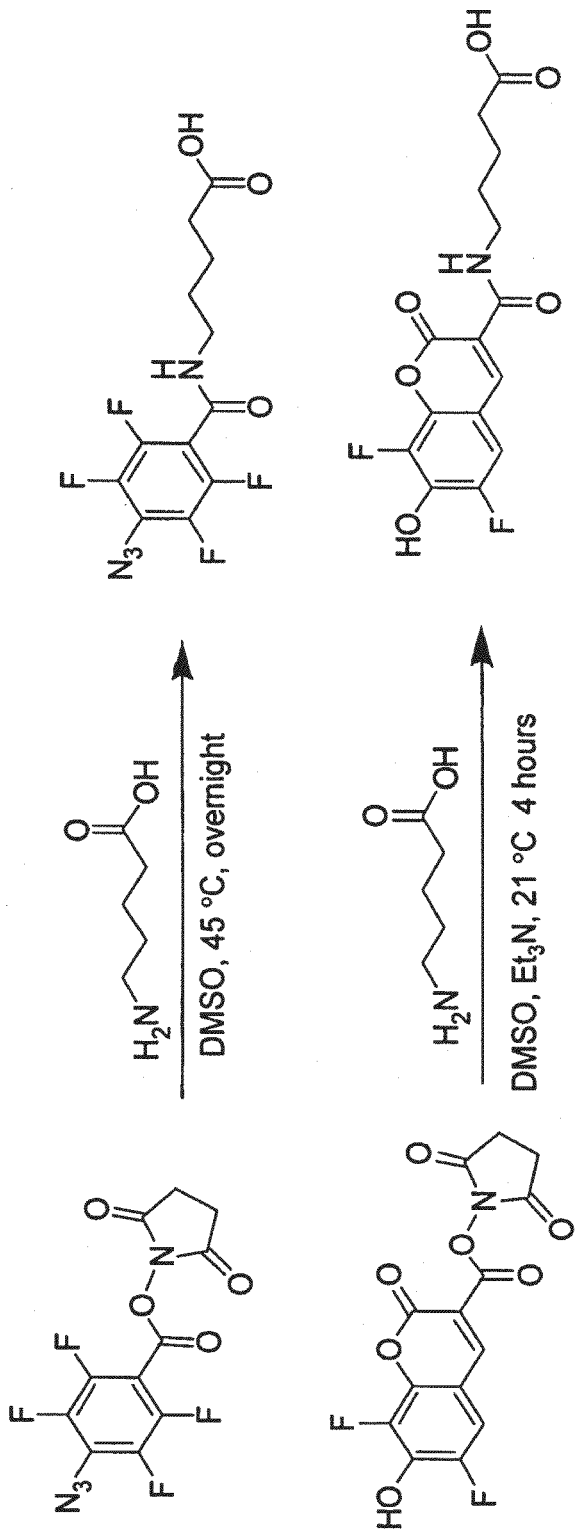
FIG. 1 shows a diagram illustrating synthetic routes to alkyl azide and alkyne probes and for aryl azide and coumarin derivatives. Note that n=4 and n=8 alkynes were purchased from TCI America.

FIG. 1 illustrates the synthesis of various azide and alkyne lipoic acid analogs. These synthesis pathways are exemplary and other synthesis protocols can be used to generate lipoic acid analogs for use in the invention.

Accordingly, lipoic acid analogs that are not themselves directly detectable must be reacted with a detectable moiety. Each lipoic acid analog in this category will undergo a specific reaction dependent upon its functional groups and that of its reaction partner. Some of these reactions include selective derivatization with a fluorescent probe conjugated to a cyclooctyne reaction partner as described above herein and in the Examples section. It will be understood that the reaction partner may comprise any detectable moiety and is not solely limited to fluorophores. FIG. 4 illustrates the synthetic routes to cyclooctyne-probe conjugates. These synthesis pathways are exemplary and other synthesis protocols can be used to generate conjugates for use in the invention.

In some embodiments, a lipoic acid analog (e.g., an azide) may be reacted with phosphines in a Staudinger reaction. Azides and aryl phosphines generally have no cellular counterparts. As a result, the reaction is quite specific. Azide variants with improved stability against hydrolysis in water at pH 6-8 are also useful in the methods of the invention. The alkyne/azide [3+2] cycloaddition chemistry, based on Click chemistry (Wang et al. J. Am. Chem. Soc. 125:11164-11165, 2003), is also specific, in part because the two reactive partners do not have cellular counterparts (i.e., the two functional groups are non-naturally occurring). Nonlimiting examples of fluorophores that may be conjugated to a cyclooctyne are Alexa Fluor 568 and Cy3.

As stated above, other lipoic acid analogs may be themselves directly detectable, e.g., comprise a detectable label. Examples of such lipoic acid analogs include but are not limited to those conjugated to coumarin, fluorescein, aryl azides, diazirines, benzophenones, resorufins, various xanthene-type fluorophores, chloroalkanes, metal-binding ligands, or derivatives thereof.

A lipoic acid analog can also be fluorogenic. As used herein, a fluorogenic compound is one that is not detectable (e.g., fluorescent) by itself, but when conjugated to another moiety becomes fluorescent. An example of this is non-fluorescent coumarin phosphine which reacts with azides to produce fluorescent coumarin. Fluorogenic lipoic acid analogs are especially useful to keeping background to a minimum (e.g., cellular imaging applications).

As stated above, the lipoic acid analogs can be conjugated to detectable labels, e.g., through conjugation using a cyclooctyne reaction partner. A "detectable label" as used herein is a molecule or compound that can be detected by a variety of methods including fluorescence, electrical conductivity, radioactivity, size, and the like. The label may be of a chemical (e.g., carbohydrate, lipid, etc.), peptide or nucleic acid nature although it is not so limited. The label may be directly or indirectly detectable. The label can be detected directly for example by its ability to emit and/or absorb light of a particular wavelength. A label can be detected indirectly by its ability to bind, recruit and, in some cases, cleave (or be cleaved by) another compound, thereby emitting or absorbing energy. An example of indirect detection is the use of an enzyme label that cleaves a substrate into visible products.

The type of label used will depend on a variety of factors, such as but not limited to the nature of the protein ultimately being labeled. The label should be sterically and chemically compatible with the lipoic acid analog, the acceptor peptide and the target protein. In most instances, the label should not interfere with the activity of the target protein.

Generally, the label can be selected from the group consisting of a fluorescent molecule, a chemiluminescent molecule (e.g., chemiluminescent substrates), a phosphorescent molecule, a radioisotope, an enzyme, an enzyme substrate, an affinity molecule, a ligand, an antigen, a hapten, an antibody, an antibody fragment, a chromogenic substrate, a contrast agent, an MRI contrast agent, a PET label, a phosphorescent label, and the like.

Specific examples of labels include radioactive isotopes such as $^{32}P$ or $^{3}H$; haptens such as digoxigenin and dintrophenyl; affinity tags such as a FLAG tag, an HA tag, a histidine tag, a GST tag; enzyme tags such as alkaline phosphatase, horseradish peroxidase, beta-galactosidase, etc. Other labels include fluorophores such as fluorescein isothiocyanate ("FITC"), Texas Red®, tetramethylrhodamine isothiocyanate ("TRITC"), 4,4-difluoro-4-bora-3a, and 4a-diaza-s-indacene ("BODIPY"), Cy-3, Cy-5, Cy-7, Cy-Chrome™, R-phycoerythrin (R-PE), PerCP, allophycocyanin (APC), PharRed™, Mauna Blue, Alexa™ 350 and other Alexa™ dyes, and Cascade Blue®.

The labels can also be antibodies or antibody fragments or their corresponding antigen, epitope or hapten binding partners. Detection of such bound antibodies and proteins or peptides is accomplished by techniques well known to those skilled in the art. Antibody/antigen complexes which form in response to hapten conjugates are easily detected by linking a label to the hapten or to antibodies which recognize the hapten and then observing the site of the label. Alternatively, the antibodies can be visualized using secondary antibodies or fragments thereof that are specific for the primary antibody used. Polyclonal and monoclonal antibodies may be used. Antibody fragments include Fab, F(ab)$_2$, Fd and antibody fragments which include a CDR3 region. The conjugates can also be labeled using dual specificity antibodies.

The label can be a positron emission tomography (PET) label such as 99 m technetium and 18FDG.

The label can also be an singlet oxygen radical generator including but not limited to resorufin, malachite green, fluorescein, benzidine and its analogs including 2-aminobiphenyl, 4-aminobiphenyl, 3,3'-diaminobenzidine, 3,3'-dichlorobenzidine, 3,3'-dimethoxybenzidine, and 3,3'-dimethylbenzidine. These molecules are useful in EM staining and can also be used to induce localized toxicity.

The label can also be an analyte-binding group such as but not limited to a metal chelator (e.g., a copper chelator). Examples of metal chelators include EDTA, EGTA, and molecules having pyridinium substituents, imidazole substituents, and/or thiol substituents. These labels can be used to analyze local environment of the target protein (e.g., $Ca^{2+}$ concentration).

The label can also be a heavy atom carrier. Such labels would be particularly useful for X-ray crystallographic study of the target protein. Heavy atoms used in X-ray crystallography include but are not limited to Au, Pt and Hg. An example of a heavy atom carrier is iodine.

The label may also be a photoactivatable cross-linker. A photoactivable cross linker is a cross linker that becomes reactive following exposure to radiation (e.g., a ultraviolet radiation, visible light, etc.). Examples include benzophenones, aziridines, a photoprobe analog of geranylgeranyl diphosphate (2-diazo-3,3,3-trifluoropropionyloxy-farnesyl diphosphate or DATFP-FPP) (Quellhorst et al. J Biol. Chem. 2001 Nov. 2; 276(44):40727-33), a DNA analogue 5-[N-(p-azidobenzoyl)-3-aminoallyl]-dUTP (N(3)RdUTP), sulfosuccinimidyl-2(7-azido-4-methylcoumarin-3-acetamido)-ethyl-1,3'-dithiopropionate (SAED) and 1-[N-(2-hydroxy-5-azidobenzoyl)-2-aminoethyl]-4-(N-hydroxysuccinimidyl)-succinate.

The label may also be a photoswitch label. A photoswitch label is a molecule that undergoes a conformational change in response to radiation. For example, the molecule may change its conformation from cis to trans and back again in response to radiation. The wavelength required to induce the conformational switch will depend upon the particular photoswitch label. Examples of photoswitch labels include azobenzene, 3-nitro-2-naphthalenemethanol. Examples of photoswitches are also described in van Delden et al. Chemistry. 2004 Jan. 5; 10(1):61-70; van Delden et al. Chemistry. 2003 Jun. 16; 9(12):2845-53; Zhang et al. Bioconjug Chem. 2003 Jul.-Aug.; 14(4):824-9; Irie et al. Nature. 2002 Dec. 19-26; 420 (6917):759-60; as well as many others.

The label may also be a photolabile protecting group. Examples of photolabile protecting group include a nitrobenzyl group, a dimethoxy nitrobenzyl group, nitroveratryloxycarbonyl (NVOC), 2-(dimethylamino)-5-nitrophenyl (DANP), Bis(o-nitrophenyl)ethanediol, brominated hydroxyquinoline, and coumarin-4-ylmethyl derivative. Photolabile protecting groups are useful for photocaging reactive functional groups.

The label may comprise non-naturally occurring amino acids. Examples of non-naturally occurring amino acids include for glutamine (Glu) or glutamic acid residues: cc aminoadipate molecules; for tyrosine (Tyr) residues: phenylalanine (Phe), 4-carboxymethyl-Phe, pentafluoro phenylalanine (PfPhe), 4-carboxymethyl-L-phenylalanine (cmPhe), 4-carboxydifluoromethyl-L-phenylalanine ($F_2$ cmPhe), 4-phosphonomethyl-phenylalanine (Pmp), (difluoro-phosphonomethyl)phenylalanine ($F_2$Pmp), O-malonyl-L-tyrosine (malTyr or OMT), and fluoro-O-malonyltyrosine (FOMT); for proline residues: 2-azetidinecarboxylic acid or pipecolic acid (which have 6-membered, and 4-membered ring structures respectively); 1-aminocyclohexylcarboxylic acid ($Ac_6c$); 3-(2-hydroxynaphtalen-1-yl)-propyl; S-ethyl-isothiourea; 2-$NH_2$-thiazoline; 2-$NH_2$-thiazole; asparagine residues substituted with 3-indolyl-propyl at the C terminal carboxyl group. Modifications of cysteines, histidines, lysines, arginines, tyrosines, glutamines, asparagines, prolines, and carboxyl groups are known in the art and are described in U.S. Pat. No. 6,037,134. These types of labels can be used to study enzyme structure and function.

The label may be an enzyme or an enzyme substrate. Examples of these include (enzyme (substrate)): Alkaline Phosphatase (4-Methylumbelliferyl phosphate Disodium salt; 3-Phenylumbelliferyl phosphate Hemipyridine salt); Aminopeptidase (L-Alanine-4-methyl-7-coumarinylamide trifluoroacetate; Z-L-arginine-4-methyl-7-coumarinylamide hydrochloride; Z-glycyl-L-proline-4-methyl-7-coumarinylamide); Aminopeptidase B (L-Leucine-4-methyl-7-coumarinylamide hydrochloride); Aminopeptidase M (L-Phenylalanine 4-methyl-7-coumarinylamide trifluoroacetate); Butyrate esterase (4-Methylumbelliferyl butyrate); Cellulase (2-Chloro-4-nitrophenyl-beta-D-cellobioside); Cholinesterase (7-Acetoxy-1-methylquinolinium iodide; Resorufin butyrate); alpha-Chymotrypsin, (Glutaryl-L-phenylalanine 4-methyl-7-coumarinylamide); N—(N-Glutaryl-L-phenylalanyl)-2-aminoacridone; N—(N-Succinyl-L-phenylalanyl)-2-aminoacridone; Cytochrome P450 2B6 (7-Ethoxycoumarin); Cytosolic Aldehyde Dehydrogenase (Esterase Activity) (Resorufin acetate); Dealkylase ($O^7$-Pentylresorufin); Dopamine beta-hydroxylase (Tyramine); Esterase (8-Acetoxypyrene-1,3,6-trisulfonic acid Trisodium salt; 3-(2 Benzoxazolyl)umbelliferyl acetate; 8-Butyryloxypyrene-1, 3,6-trisulfonicacid Trisodium salt; 2',7'-Dichlorofluorescin diacetate; Fluorescein dibutyrate; Fluorescein dilaurate; 4-Methylumbelliferyl acetate; 4-Methylumbelliferyl butyrate; 8-Octanoyloxypyrene-1,3,6-trisulfonic acid Trisodium salt; 8-Oleoyloxypyrene-1,3,6-trisulfonic acid Trisodium salt; Resorufin acetate); Factor X Activated (Xa) (4-Methylumbelliferyl 4-guanidinobenzoate hydrochloride Monohydrate); Fucosidase, alpha-L-(4-Methylumbelliferyl-alpha-L-fucopyranoside); Galactosidase, alpha-(4-Methylumbelliferyl-alpha-D galactopyranoside); Galactosidase, beta-(6,8-Difluoro-4-methylumbelliferyl-beta-D-galactopyranoside; Fluorescein di(beta-D-galactopyranoside); 4-Methylumbelliferyl-alpha-D-galactopyranoside; 4-Methylumbelliferyl-beta-D-lactoside: Resorufin-beta-D-galactopyranoside; 4-(Trifluoromethyl)umbelliferyl-beta-D-galactopyranoside; 2-Chloro-4-nitrophenyl-beta-D-lactoside); Glucosaminidase, N-acetyl-beta-(4-Methylumbelliferyl-N-acetyl-beta-D-glucosaminide Dihydrate); Glucosidase, alpha-(4-Methylumbelliferyl-alpha-D-glucopyranoside); Glucosidase, beta-(2-Chloro-4-nitrophenyl-beta-D-glucopyranoside; 6,8-Difluoro-4-methylumbelliferyl-beta-D-glucopyranoside; 4-Methylumbelliferyl-beta-D-glucopyranoside; Resorufin-beta-D-glucopyranoside; 4-(Trifluoromethyl)umbelliferyl-beta-D-glucopyranoside); Glucuronidase, beta-(6,8-Difluoro-4-methylumbelliferyl-beta-D-glucuronide Lithium salt; 4-Methylumbelliferyl-beta-D-glucuronide Trihydrate); Leucine aminopeptidase (L-Leucine-4-methyl-7-coumarinylamide hydrochloride); Lipase (Fluorescein dibutyrate; Fluorescein dilaurate; 4-Methylumbelliferyl butyrate; 4-Methylumbelliferyl enanthate; 4-Methylumbelliferyl oleate; 4-Methylumbelliferyl palmitate; Resorufin butyrate); Lysozyme (4-Methylumbelliferyl-N,N',N''-triacetyl-beta-chitotrioside); Mannosidase, alpha-(4-Methylumbelliferyl-alpha-D-mannopyranoside); Monoamine oxidase (Tyramine); Monooxygenase (7-Ethoxycoumarin); Neuraminidase (4-Methylumbelliferyl-N-acetyl-alpha-D-neuraminic acid Sodium salt Dihydrate); Papain (Z-L-arginine-4-methyl-7-coumarinylamide hydrochloride); Peroxidase (Dihydrorhodamine 123); Phosphodiesterase (1-Naphthyl 4-phenylazophenyl phosphate; 2-Naphthyl 4-phenylazophenyl phosphate); Prolyl endopeptidase (Z-glycyl-L-proline-4-methyl-7-coumarinylamide; Z-glycyl-L-proline-2-naphthylamide; Z-glycyl-L-proline-4-nitroanilide); Sulfatase (4-Methylumbelliferyl sulfate Potassium salt); Thrombin (4-Methylumbelliferyl 4-guanidinobenzoate hydrochloride Monohydrate); Trypsin (Z-L-arginine-4-methyl-7-coumarinylamide hydrochloride; 4-Methylumbelliferyl 4-guanidinobenzoate hydrochloride Monohydrate); Tyramine dehydrogenase (Tyramine).

The labels can be attached to the lipoic acid analogs either before or after the analog has been conjugated to the acceptor peptide, presuming that the label does not interfere with the activity of lipoic acid ligase. Labels can be attached to the lipoic acid analogs by any mechanism known in the art. Some of these mechanisms are already described above for particular analogs. Other examples of functional groups which are reactive with various labels include, but are not limited to, (functional group: reactive group of light emissive compound) activated ester:amines or anilines; acyl azide:amines or anilines; acyl halide:amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride:alcohols, phenols, amines or anilines; aryl halide:thiols; aziridine:thiols or thioethers; carboxylic acid:amines, anilines, alcohols or alkyl halides; diazoalkane:carboxylic acids; epoxide:thiols; haloacetamide:thiols; halotriazine:amines, anilines or phenols; hydrazine:aldehydes or ketones; hydroxyamine:aldehydes or ketones; imido ester:amines or anilines; isocyanate:amines or anilines; and isothiocyanate:amines or anilines.

The labels are detected using a detection system. The nature of such detection systems will depend upon the nature of the detectable label. The detection system can be selected from any number of detection systems known in the art. These include a fluorescent detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system.

The invention provides in some instances lipoic acid ligase or mutant thereof and/or lipoic acid analogs in an isolated form. As used herein, an isolated lipoic acid ligase or mutant thereof is a lipoic acid ligase or mutant thereof that is separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Isolated lipoic acid analogs similarly are analogs that have been substantially separated from either their native environment (if it exists in nature) or their synthesis environment. Accordingly, the lipoic acid analogs are substantially separated from any or all reagents present in their synthesis reaction that would be toxic or otherwise detrimental to the target protein, the acceptor peptide, the lipoic acid ligase mutant, or the labeling reaction. Isolated lipoic acid analogs, for example, include compositions that comprise less than 25% contamination, less than 20% contamination, less than 15% contamination, less than 10% contamination, less than 5% contamination, or less than 1% contamination (w/w).

The invention further provides nucleic acids coding for lipoic acid ligase mutants. These nucleic acids therefore encode a lipoic acid ligase mutant having an amino acid substitution at one or more of the following residues of wild-type LplA (such as that set forth as SEQ ID NO:11) 16, 17, 19, 20, 21, 37, 37+71, 37+20, 37+35, 35, 41, 70, 71, 72, 79, 85, 87, 140, 147, and 149. Specific examples of amino acid substitutions may be one or more amino acids that correspond to: N16A, L17A, V19A, E20A, E21A, W37A, W37G, W37S, W37V, W37A+S71A, W37A+E20A, W37L, W37I, W37T, W37N, W37V+E20G, W37V +F35A, W37V+E20A, F35A, N41A, R70A, S71A, S72A, H79A, C85A, T87A, R140A, F147A, H149A, and H149V of wild-type E. coli lipoic acid ligase.

The nucleotide sequence of wild-type lipoic acid ligase is provided as SEQ ID NO: 12. One of ordinary skill in the art will be able to determine the codons corresponding to each of the amino acid residues recited herein.

The invention also embraces degenerate nucleic acids that differ from the mutant nucleic acid sequences provided herein in codon sequence due to degeneracy of the genetic code. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating mutant. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

The invention also involves expression vectors coding for lipoic acid ligase mutants and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *E. coli*, mammalian cells such as mouse, hamster, pig, goat, primate, etc., and other eukaryotic cells such as *Xenopus* cells, *Drosophila* cells, Zebrafish cells, *C. elegans* cells, and the like. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences (i.e., reporter sequences) suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., beta-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous nucleic acid, usually DNA, molecules, encoding a lipoic acid ligase mutant. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is disclosed by Warnier et al., in intradermal injection in mice for immunization against P1A (Int. J. Cancer, 67:303-310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, lipoic acid ligase mutant encoding nucleic acid containing expression vectors, to transfect host cells and cell lines, be these prokaryotic (e.g., *E. coli*), or eukaryotic (e.g., rodent cells such as CHO cells, primate cells such as COS cells, *Drosophila* cells, Zebrafish cells, *Xenopus* cells, *C. elegans* cells, yeast expression systems and recombinant baculovirus expression in insect cells). Especially useful are mammalian cells such as human, mouse, hamster, pig, goat, primate, etc., from a wide variety of tissue types including primary cells and established cell lines.

Various methods of the invention also require expression of fusion proteins in vivo. The fusion proteins are generally recombinantly produced proteins that comprise the lipoic acid ligase acceptor peptides. Such fusions can be made from virtually any protein and those of ordinary skill in the art will be familiar with such methods. Further conjugation methodology is also provided in U.S. Pat. Nos. 5,932,433; 5,874,239 and 5,723,584.

In some instances, it may be desirable to place the lipoic acid ligase or mutant thereof and possibly the fusion protein under the control of an inducible promoter. An inducible promoter is one that is active in the presence (or absence) of a particular moiety. Accordingly, it is not constitutively active. Examples of inducible promoters are known in the art and include the tetracycline responsive promoters and regulatory sequences such as tetracycline-inducible T7 promoter system, and hypoxia inducible systems (Hu et al. Mol Cell Biol. 2003 Dec.; 23(24):9361-74). Other mechanisms for controlling expression from a particular locus include the use of synthetic short interfering RNAs (siRNAs).

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a subject shall mean an organism such as an insect, a yeast cell, a worm, a fish, or a human or animal including but not limited to a dog, cat, horse, cow, pig, sheep, goat, chicken, rodent e.g., rats and mice, primate, e.g., monkey. Subjects include vertebrate and invertebrate species. Subjects can be house pets (e.g., dogs, cats, fish, etc.), agricultural stock animals (e.g., cows, horses, pigs, chickens, etc.), laboratory animals (e.g., mice, rats, rabbits, etc.), zoo animals (e.g., lions, giraffes, etc.), but are not so limited. Methods of the invention may be used to introduce labels for MRI, PET, or multiphoton imaging, etc. into and for detection in live animals. Methods of the invention may be applied to living animals, for example, transgenic animals, thus subjects of the invention may be transgenic animals.

The compositions, as described above, are administered in effective amounts for labeling of the target proteins. The effective amount will depend upon the mode of administration, the location of the cells being targeted, the amount of target protein present and the level of labeling desired.

The methods of the invention, generally speaking, may be practiced using any mode of administration that is medically acceptable, meaning any mode that produces effective levels of the active compounds without causing clinically unacceptable adverse effects. A variety of administration routes are available including but not limited to oral, rectal, topical, nasal, intradermal, or parenteral routes. The term "parenteral" includes subcutaneous, intravenous, intramuscular, or infusion.

When peptides are used, in certain embodiments one desirable route of administration is by pulmonary aerosol. Techniques for preparing aerosol delivery systems containing peptides are well known to those of skill in the art. Generally, such systems should utilize components which will not significantly impair the biological properties of the peptides or proteins (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing protein or peptide aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that subject tolerance permits. Multiple doses per day are contemplated to achieve appropriate systemic levels of compounds.

The agents may be combined, optionally, with a pharmaceutically-acceptable carrier. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The components of the pharmaceutical compositions also are capable of being commingled with the molecules of the present invention, and with each other, in a manner such that there is no interaction that would substantially impair the desired pharmaceutical efficacy.

The invention in other aspects includes pharmaceutical compositions. When administered, the pharmaceutical preparations of the invention are applied in pharmaceutically-acceptable amounts and in pharmaceutically-acceptably compositions. Such preparations may routinely contain salt, buffering agents, preservatives, compatible carriers, and the like. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the labeling reagents. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. RNA, DNA, and intact virions can be encapsulated within the aqueous interior and be delivered to cells in a biologically active form (Fraley, et al., *Trends Biochem. Sci.*, (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In one important embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein an agent is dispersed throughout a solid polymeric matrix) or a microcapsule (wherein an agent is stored in the core of a polymeric shell). Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng.*, (1996) 52:96-101 and Mathiowitz et al., *Nature*, (1997) 386:410-414.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, agents are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butiric acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, JT Jr., et al., *Nature*, 1999, 397:335-338, the contents of which are expressly incorporated herein by reference.

Use of a long-term sustained release implant may be particularly suitable for treatment of chronic conditions. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Also described herein is a method for imaging protein-protein interaction (PPI) via a reaction catalyzed by a lipoic acid ligase. FIG. 10 provides an example of how this imaging method is performed. In this method, A and B are two proteins whose interaction is to be studied. A lipoic acid ligase polypeptide (a polypeptide having the lipoic acid ligase activity) is fused to protein A, and an acceptor polypeptide (e.g., a low affinity acceptor polypeptide as described above) is fused to protein B. If A and B interact, the ligase attaches a probe, which is a lipoic acid analog as described herein, to the acceptor polypeptide. If A and B do not interact, the enzyme and peptide do not associate and no labeling occurs. An example of this imaging method is provided in Example 4 below.

The system is engineered to provide high labeling sensitivity when an interaction occurs and low background in the absence of an interaction. This is achieved by treating the interaction as a kinetic switch: when no interaction occurs, the rate of pep-tide labeling by the enzyme is undetectably slow, but when an interaction does occur, the labeling rate is maximally fast. Such switching depends on the kinetic parameters of our system. In the absence of a PPI, the protein concentrations in the cell are far below the ligase-acceptor polypeptide $K_m$, and the bimolecular reaction rate will be governed by kcat/Km. In the presence of a PPI, on the other hand, when the local concentration of the acceptor polypeptide with respect to the ligase is very high, the pseudo-zero-order reaction rate is governed by kcat. Therefore, by engineering high Km, background labeling can be minimized, and by engineering high kcat, signal in the presence of a PPI can be maximized.

The invention will be more fully understood by reference to the following examples. These examples, however, are merely intended to illustrate the embodiments of the invention and are not to be construed to limit the scope of the invention.

EXAMPLES

Example 1

Introduction

The following are general synthetic methods used in the experiments described herein, including those of Example 2.
General Synthetic Methods Reagents were purchased from Sigma-Aldrich (St, Louis, Mo.), Alfa Aesar (Ward Hill, Mass.), TCI America (Portland, Oreg.), Invitrogen (Carlsbad, Calif.), or GE Healthcare and used without further purification. Analytical thin layer chromatography was performed using 0.25 mm silica gel 60 $F_{254}$ plates and visualized with ninhydrin or bromocresol. Flash column chromatography was carried out using silica gel (ICN SiliTech 32-63D). Mass spectra were recorded on an Applied Biosystems 200 QTRAP Mass Spectrometer (foster City, Calif.) using electrospray ionization. HPLC was performed on a Varian Prostar Instrument (Palo Alto, Calif.) equipped with an autosampler and photo-diode-array detector. For analytical HPLC, a reverse-phase 250×4.6 mm Microsorb-MV 300 C18 column was used. For preparative HPLC, a reverse-phase 250×10 mm Microsorb-MV 100 C18 column was used. Chromatograms were recorded at 210 nm unless otherwise noted. $^1$H NMR spectra were recorded on a Varian Mercury 300 MHz instrument. Chemical shifts are reported in delta (δ) units, parts per million (ppm), and referenced to the residual solvent peak. Coupling constants (J) are reported in hertz (Hz). The following abbreviations for multiplets are used: s, singlet; dt, doublet of triplets; t, triplet; m, multiplet. Probes were stored as DMF solutions (3-5 M) at −20° C.

Synthesis of Alkyl Azide Probes (FIG. 1)

n=6 azide (9). To an ice-cooled solution of sodium azide (1.78 g, 27.5 mmol) in water (4.5 mL) was added dichloromethane (7.5 mL). The biphasic mixture was stirred vigorously and trifluoromethanesulfonic anhydride (0.93 mL, 5.5 mmol) was added slowly over 5 minutes. The reaction was allowed to proceed for 2 hours at 4° C. The aqueous layer was then separated from the organic phase and extracted twice with dichloromethane (2×25 mL). The combined dichloromethane extracts were washed with saturated sodium carbonate solution and concentrated to 13 mL under reduced pressure. This crude triflyl azide was used without further purification. 7-aminoheptanoic acid (0.35 g, 2.4 mmol) was dissolved in water (7.8 mL) and combined with potassium carbonate (0.52 g, 3.8 mmol) and copper sulfate pentahydrate (6.6 mg, 26.4 µmol). Methanol (15.6 mL) was added to dissolve the mixture, followed by crude triflyl azide. The reaction was allowed to proceed at 21° C. overnight. The mixture was concentrated under reduced pressure, treated with $NaH_2PO_4$ buffer (45 mL, 250 mM, pH 6.2) and extracted with ethyl acetate (4×50 mL) to remove byproduct sulfonamide and excess triflyl azide. The pH of the aqueous solution was further reduced to 2.0 using concentrated HCl. The product was extracted with ethyl acetate (4×50 mL), dried over magnesium sulfate, and finally evaporated to dryness under reduced pressure to afford the desired product as a pale yellow oil (42 mg, 0.26 mmol, 10.7%). $^1$H NMR ($CDCl_3$): δ 3.27 (t, 2H, J=6.9), 2.37 (t, 2H, J=7.5), 1.62 (m, 4H), 1.39 (m, 4H). ESI-MS calculated for [M−H]$^-$: 170.22; observed 170.16.

General procedure for synthesis of n=5, 7-10 azides (10). To a solution of the corresponding bromo-alkanoic acid (10 mmol of 6, 8, 9, 10 or 11-bromo-alkanoic acid) in DMF (20 mL) was added sodium azide (0.98 g, 15 mmol). The mixture was allowed to stir at 21° C. overnight. The progress of the reaction was monitored by thin layer chromatography (0-40% ethyl acetate in hexanes). DMF was removed under reduced pressure and the resulting residue was re-suspended in HCl (25 mL, 1 N) and subsequently extracted with ethyl acetate (4×25 mL). The combined organic layers were dried over magnesium sulfate, and evaporated to dryness under reduced pressure to afford the desired azido-alkanoic acid as a pale yellow oil. Typical yields ranged from 35-65%. Characterization data for n=5 azide (6-azidohexanoic acid). $^1$H NMR ($CDCl_3$): δ 3.28 (t, 2H, J=6.9), 2.37 (t, 2H, J=7.5), 1.64 (m, 4H), 1.35 (m, 2H). ESI-MS calculated for [M−H]$^-$: 156.17; observed 156.12. Characterization data for n=7 azide (8-azidooctanoic acid). $^1$H NMR ($CDCl_3$): δ 3.26 (t, 2H, J=6.8), 2.36 (t, 2H, J=7.5), 1.62 (m, 4H), 1.35 (m, 6H). ESI-MS calculated for [M−H]$^-$: 184.22; observed 184.14. Characterization data for n=8 azide (9-azidononanoic acid). $^1$H NMR ($CDCl_3$) δ 3.25 (t, 2H, J=6.9), 2.34, (t, 2H, J=7.5), 1.60 (m, 4H), 1.32 (m, 8H). ESI-MS calculated for [M−H]$^-$: 198.25; observed 198.18. Characterization data for n=9 azide (10-azidodecanoic acid). $^1$H NMR ($CDCl_3$) δ 3.25 (t, 2H, J=7.1), 2.35, (t, 2H, J=7.5), 1.61 (m, 4H), 1.31 (m, 10H). ESI-MS calculated for [M−H]$^-$: 212.28; observed 212.16. Characterization data for n=10 azide (11-azidoundecanoic acid). $^1$H NMR ($CDCl_3$) δ 3.25 (t, 2H, J=7.1), 2.35, (t, 2H, J=7.5), 1.62 (m, 4H), 1.29 (m, 12H). ESI-MS calculated for [M−H]$^-$: 226.31; observed 226.20.

Synthesis of Alkyne Probes (FIG. 1)

Synthesis of n=5 and n=7 alkynes (11). To a solution of 10 mmol 6- or 8-bromo-alkanoic acid in DMSO (23 mL) was added lithium acetylide ethylenediamine (0.92 g, 10 mmol) slowly over a period of 5 minutes. The reaction mixture was stirred overnight at 21° C. Subsequently, water (25 mL) was added and the product extracted with dichloromethane (3×25 mL). Dichloromethane was removed under reduced pressure to yield the desired alkynoic acid as a brownish solid. Yields ranged from 5-7%. Characterization data for n=5 alkyne (7-octynoic acid). $^1$H NMR ($CDCl_3$) δ 2.36 (t, 2H, J=7.1), 2.19, (t, 2H, J=6.9), 1.94 (t, 1H, J=2.6), 1.69-1.34 (m, 6H). ESI-MS calculated for [M−H]$^-$: 139.18; observed 139.08. Characterization data for n=7 alkyne (9-decynoic acid). $^1$H NMR ($CDCl_3$) δ 2.35 (t, 2H, J=7.5), 2.18, (dt, 2H, J=6.9, J=2.7), 1.94 (t, 1H, J=2.7), 1.63 (m, 2H), 1.51 (m, 2H), 1.35 (m, 6H) ESI-MS calculated for [M−H]$^-$: 167.23; observed 167.22.

Synthesis of 5-(4-azido-2,3,5,6-tetrafluorobenzamido) pentanoic acid: To a solution of 5-aminovaleric acid (12 mg, 100 µmol) in dry DMSO (250 µL) was added N-succinimidyl 4-azido-2,3,5,6-tetrafluorobenzoate (25 mg, 75 µmol). The reaction was allowed to proceed overnight at 45° C. in the dark. The mixture was then acidified with 250 µL of 0.5 N hydrochloric acid and extracted with 400 µL of ethyl acetate three times. The combined extracts were concentrated in vacuo and purified by silica chromatography using 2:1 hexane-ethyl acetate to yield the desired product as a white powder. Yielded: 3 mg, 9 µmol, 12%. TLC: $R_f$=0.3 (1:1 hexane-ethyl acetate) $^1$H-NMR (300 MHz, $(CD_3)_2SO$): δ 12.03 (s, 1H), 8.89 (t, 1H, J=5.4), 3.23 (q, 2H, J=6.3), 2.22 (t, 2H, J=7.2), 1.497 (m, 4H). ESI-MS m/z: (neg) 333.07 [M−H]$^-$. Calc. 334.23

Synthesis of 5-(3-amido-6,8-difluoro-7-hydroxycoumarin)pentanoic acid: To a solution of 5-aminovaleric acid (1.7 mg, 14.6 mmol) in anhydrous DMSO (200 µL) was added triethylamine (2.2 µL, 14.6 µmol) and stirred for 5 mins. The N-hydroxy succinimidyl ester of 3-carboxy-6,8-difluoro-7-hydroxycoumarin (2.5 mg, 7.3 µmol) was then added and the reaction was allowed to proceed for 4 hours at 21° C. Estimated yield 70%. ESI-MS: calculated for [M−H]$^-$: 340.07; observed 340.26.

Engineering a Peptide Substrate for LplA.

To rationally design a peptide substrate, we examined the NMR structure of E2p, which presents the lysine lipoylation site at the tip of a sharp β-turn (1). Mutagenesis studies have shown that, while accurate positioning of the target lysine within the β-turn is essential for LplA recognition, the residues flanking the lysine can be varied (2). We designed three candidate peptides, peptides 4, 6, and 7 in FIG. 3; (lysine lipoylation site is underlined) by copying the 17-amino acid stretch encompassing the lysine lipoylation sites in each of the three natural substrate proteins E2p, E2o, and H-protein. Two more peptides (shown in FIG. 3) were designed to resemble the natural protein substrate (BCCP, peptide 1) and artificial peptide substrate (AP, peptide 2) of the mechanistically related enzyme E. coli biotin ligase (BirA). E. coli BCCP and E2p have similar overall folds, with similar positioning of their acceptor lysines within β-turns (2). We also tested peptides derived from a mutant of E. coli BCCP (peptide 3, FIG. 3) and from E2p of Bacillus stearothermophilus (peptide 5, FIG. 3), proteins that have previously been shown to be recognized by E. coli LplA (2,3).

These 7 peptides were cloned as N-terminal fusions to the protein HP1 (4), expressed and purified, and tested using our HPLC assay (measurements of % conversion were performed in triplicate). The table in FIG. 3 shows that three peptides were significantly lipoylated by wild-type LplA, with peptide 6 derived from E. coli E2o giving the best conversion. To see if we could further improve peptide 6, we introduced several point mutations (data not shown). Only one of these, the Val(+1)Ala mutant (peptide 8), gave an increase in ligation rate. We measured the $k_{cat}$ for LplA-catalyzed ligation of azide 7 to peptide 8 (0.048±0.001 s$^{-1}$, data not shown), and determined that it was only 2.3-fold slower than the corresponding ligation $k_{cat}$ for E2p (FIG. 2B). In FIG. 3, conversion values are reported relative to peptide 8, whose percent conversion is normalized to 100%.

To test the transposability of peptide 8, we fused it to the C-terminal end of HP1 (to give peptide 9). The lipoylation rate dropped 5-fold, but was then partially recovered by adding five extra C-terminal amino acids to give peptide 10. This final 22-amino acid sequence was named the LplA acceptor peptide, or LAP, and used in all subsequent experiments.

Synthesis of OCT-Fluorophore Conjugates (FIG. 4)

Synthesis of OCT-PEG (3). To a solution of OCT acid 1$^5$ (32 mg, 123 µmol) in dry dichloromethane (DCM, 750 µL) was added triethylamine (TEA, 34 µL, 246 µmol). The mixture was stirred for 5 minutes at ambient temperature. Pentafluorophenyl trifluoroacetate (PFP-TFA, 42 µL, 246 µmol) was added slowly to the reaction mixture over 3 minutes and the reaction was allowed to proceed for 3 hours. The reaction mixture was concentrated in vacuo, then purified by silica chromatography (10% ethyl acetate in hexane) to afford OCT-PFP 2 as a colorless solid (45.6 mg, 107 µmol, 87.3%). The solid was immediately dissolved in dry DCM (1 mL), and combined with TEA (29 µL, 214 µmol). O,O'-Bis(3-aminopropyl)diethylene glycol (diamino-PEG, 71 µL, 535 µmol) was added, and the reaction mixture was allowed to stir overnight at 21° C. The crude mixture was purified on a silica flash column (5:3:1 ethyl acetate:methanol:water with 4.3% triethylamine). The purified product was concentrated under reduced pressure to yield OCT-PEG 3 (27.8 mg, 60 µmol, 56%). ESI-MS calculated for [M+H]$^+$: 463.29; observed 463.44.

Synthesis of OCT-PEG-Alexa Fluor 568 (4) and OCT-PEG-Cy3 (5). To a solution of OCT-PEG 3 (0.6 mg, 1.3 µmol) in anhydrous DMSO (200 µL) was added TEA (0.6 µL, 4 µmol). The N-hydroxy succinimidyl ester of either Cy3 or Alexa Fluor 568 (1.3 µmol) was then added and the reaction was allowed to stir for 4 hours at 21° C. The crude product was purified by HPLC on a reverse phase column. Chromatograms were recorded both at 210 nm and 550 nm. The following conditions were used for elution: 30-80% acetonitrile in water over 30 minutes; flow rate 5.0 mL/minute. Solvent was removed in vacuo to afford the OCT-PEG-fluorophore conjugates. Estimated yield 50-65%. ESI-MS for OCT-PEG-Alexa Fluor 568 (4): calculated for [M−H]$^-$: 1137.42; observed 1137.54. ESI-MS for OCT-PEG-Cy3 (5): calculated for [M+H]$^+$: 1075.48; observed 1075.08. In addition, the presence of an intact OCT moiety was confirmed by reaction of 100 µM OCT-PEG-Alexa Fluor 568 (4) or OCT-PEG-Cy3 (5) with 1 mM azide 7 in DMSO at 30° C. for 6 hours and detection of the triazole cycloadduct product by MS. ESI-MS for OCT-PEG-Alexa Fluor 568-cycloadduct: calculated for [M−H]$^-$: 1322.54; observed 1322.22. ESI-MS for OCT-PEG-Cy3-cycloadduct: calculated for [M−H]$^-$: 1258.60; observed 1258.56.

Cloning of HP1-Peptide Fusions for Recombinant Expression in Bacteria

For peptides 1-7, the histone protein 1 (HP1) gene (4) was PCR-amplified using a forward primer that introduced the desired peptide sequence after an NheI site (forward primer sequences below), and the reverse primer HP1-EcoRI.R (5' TTTT GAA TTC GGA TCC TTG CGG CTC GCC TCG TAC). The resulting PCR product was digested with NheI and EcoRI and ligated in-frame to an NheI/EcoRI digested pET21b vector. The vector introduced a C-terminal His$_6$ tag.

| Peptide | Forward Primer Sequence (NheI sites are italicized) |
|---|---|
| 1 | 5' AAAA *GCT AGC* GGC CTG AAC GAC ATC TTC GAA GCC GAC AAA GCT GAA TGG CAC GAG GGC GGT GAG GAG GAG TAC GCC GTG G (SEQ ID NO: 13) |
| 2 | 5' AAAA *GCT AGC* GGC GAT ACC CTG TGC ATC GTT GAA GCC GAC AAA GCT GAA AAC CAG ATC GAA GGC GGT GAG GAG GAG TAC GCC GTG G (SEQ ID NO: 14) |
| 3 | 5' AAAA *GCT AGC* GGC GAT ACC CTG TGC ATC GTT GAA GCC GAC AAA GCT TCT ATG GAA ATC CCG GGC GGT GAG GAG GAG TAC GCC GTG G (SEQ ID NO: 15) |
| 4 | 5' AAAA *GCT AGC* GAA CAG TCG CTG ATC ACC GTA GAA GGC GAC AAA GCT TCT ATG GAA GTT CCG GGC GGT GAG GAG GAG TAC GCC GTG G (SEQ ID NO: 16) |
| 5 | 5' AAAA *GCT AGC* GAC GAT GTA CTG TGC GAA GTA CAG AAC GAC AAA GCT GTA GTT GAA ATC CCG GGC GGT GAG GAG GAG TAC GCC GTG G (SEQ ID NO: 17) |
| 6 | 5' AAAA *GCT AGC* GAC GAA GTA CTG GTT GAA ATC GAA ACC GAC AAA GTA GTT CTG GAA GTA CCG GGC GGT GAG GAG GAG TAC GCC GTG G (SEQ ID NO: 18) |
| 7 | 5' AAAA GCT AGC GGC GAT GAC TGC GCT GTT GCT GAA TCT GTA AAA GCT GCC TCG GAC ATC TAT GGC GGT GAG GAG GAG TAC GCC GTG G (SEQ ID NO: 19) |

Peptide 8 was obtained by mutagenesis on peptide 6, using the QuikChange primer 5' GAA ATC GAA ACC GAC AAA GCA GTT CTG GAA GTA CCG GGC (SEQ ID NO:20) and its reverse complement. To clone peptide 9, the HP1 gene was PCR-amplified using the primer NdeI-HP1.F (5' AAAA CAT ATG GAG GAG GAG TAC GCC GTG G) (SEQ ID NO:21), which incorporates an NdeI site, and the primer HP1-LAP-Stop-BamHI.R (5' TTTT GGA TCC TCT TAC GGT ACT TCC AGA ACT GCT TTG TCG GTT TCG ATT TCA ACC AGT ACT TCG TCG CTA GCA TCC TTG CGG CTC GCC TCG TAC) (SEQ ID NO:22), which introduces the peptide sequence and a BamHI site. The resulting PCR product was digested with NdeI and BamHI and ligated in-frame to an NdeI/BamHI digested pET15b vector, which introduces an N-terminal His$_6$ tag. To clone peptide 10, the gene encoding peptide 9 was PCR-amplified using the same forward primer NdeI-HP1.F, and the reverse primer LAP-AAs-Stop-BamHI.R (5' TTTT GGA TCC TCT TAC TCC TCC TCA CCG CCC GGT ACT TCC AGA ACT GCT TTG TC) (SEQ ID NO:23). The PCR product was digested and ligated as above.

Cloning of LAP-CFP for Cytoplasmic Mammalian Expression

The sequence for the LAP peptide was inserted in the NheI site of a modified form of the pcDNA3 vector (Invitrogen). The vector contained the CFP gene between the BamHI and EcoRI sites (6). Primers 5' AAAA ACT AGT CGG GCT GAC GAA GTA CTG GTT GAA ATC GAA ACC GAC AAA GCA GTT CTG GAA GTA CCG GCA TCA GCA GAC GGC GCT AGC AAAA (SEQ ID NO:24) and its reverse complement were annealed together, digested with SpeI and NheI, and ligated in-frame to NheI digested pcDNA3-CFP vector.

To create the LAP(Ala)-CFP mutant, we performed QuikChange with the primer 5'G GTT GAA ATC GAA ACC GAC GCC GCA GTT CTG GAA GTA CCG G (SEQ ID NO:25) and its reverse complement.

Site Directed Mutagenesis of LplA

The pYFJ16 plasmid, a gift from John Cronan, encodes an N-terminally $His_6$-tagged LplA within the pQE-2 vector (Qiagen). To create the catalytically inactive mutant, Lys133 was mutated to alanine by QuikChange using 5' CGA AGG CGA CCG CGC AGT CTC AGG CTC GG (SEQ ID NO:26) and its reverse complement.

Cloning of LAP-CFP-TM for Mammalian Surface Expression

The LAP peptide was inserted between the BglII and AscI sites of the AP-CFP-TM plasmid[6]. Primers 5' AAAAA AGA TCT GGC GGC GAC GAA GTA CTG GTT GAA ATC GAA ACC GAC AAA GCA GTT CTG GAA GTA CCG GGC GGT GAG GAG GAG GGC GCG CCA AAAA (SEQ ID NO:27) and its reverse complement were annealed together, digested with BglII and AscI, and ligated in-frame to BglII/AscI digested AP-CFP-TM. To create the LAP(Ala) mutant, we performed QuikChange using the primer 5' G GTT GAA ATC GAA ACC GAC GCC GCA GTT CTG GAA GTA CCG G (SEQ ID NO:28) and its reverse complement.

Cloning of LAP-LDLR and LAP-GFP-LDLR

To clone LAP-GFP-LDLR, the LAP sequence was inserted in the leader sequence of LDLR, between Ser27 and Thr28, using the inverse PCR method described by Gama and Breitwieser (12) with the primers 5' CG GGC GGT GAG GAG GAG ACT GTG AGC AAG GGC GAG GAG (SEQ ID NO:29) and 5' GTA CCT CCA GAA CTG CTT TGT CGG TTT CGA TTT CAA CCA GTA CTT CGT CAC TTC TGT CGC CAA CTG CAG (SEQ ID NO:30). The PCR template was the pEGFP-LDLR plasmid, a gift from Tom Kirchhausen. To clone LAP-LDLR, the GFP gene was deleted by QuikChange using primers 5' GGA GGT ACC GGC ATC AGC AGA CGG CGG GGG AGA ATT CGA CAG ATG TG (SEQ ID NO:31) and its reverse complement.

Bacterial Expression and Purification of *E. coli* LplA

LplA was expressed from the plasmid pYFJ16, a gift from John Cronan, which encodes an N-terminally $His_6$-tagged LplA within the pQE-2 vector (Qiagen). pYFJ16 was transformed into *E. coli* BL21(DE3) cells, which were amplified in LB media supplemented with 100 μg/mL ampicillin at 37° C. until $OD_{600}$ 0.9. Enzyme expression was induced with 200 μg/mL IPTG for 3 hours at 30° C. Thereafter, cells were harvested by centrifugation (6,000 rpm, 10 minutes, 4° C.) and the pellet was resuspended in lysis buffer (50 mM Tris base, 300 mM NaCl, pH 7.8) containing 2.5 mM phenylmethylsulfonyl fluoride (PMSF) and protease inhibitor cocktail (Calbiochem). Cells were lysed by ultrasonic treatment (six 15-second bursts, with 1 minute of cooling to 4° C. between bursts). The extract was cleared by centrifugation (17,700 g, 10 minutes, 4° C.) and the $His_6$-tagged enzyme was purified using Ni-NTA agarose (Qiagen). Fractions were analyzed by 12% SDS-PAGE followed by Coomassie staining. Fractions containing LplA were pooled and dialyzed against PBS pH 7.4. Enzyme concentration was determined by measuring $A_{280}$ and using the reported extinction coefficient (46,250 $M^{-1}$ $cm^{-1}$) (13).

Bacterial Expression and Purification of E2p

A single hybrid lipoyl domain derived from the second subunit of the *E. coli* pyruvate dehydrogenase was expressed from the *E. coli* K12 strain, TM245, which was a gift from John Cronan (14,15). Transformants of strain TM245 were grown at 37° C. in LB media supplemented with 100 μg/mL ampicillin until $OD_{600}$ 0.2. Protein expression was induced with 10 μg/mL IPTG for 17 hours at 25° C. Harvested bacteria were resuspended in 20 mM sodium phosphate buffer pH 7.4 containing 2 mM EDTA, 2.5 mM PMSF, and protease inhibitor cocktail (Calbiochem). Cells were lysed by ultrasonic treatment (eight 30-second bursts, with 30 seconds of cooling to 4° C. between bursts). The extract was cleared by centrifugation (17,700 g, 40 minutes, 4° C.), before lowering the pH to 3.8 with 1 M HCl. Insoluble material was removed by two rounds of centrifugation (17,700 g, 20 minutes, 4° C. and 17,700 g, 10 minutes, 4° C.), before increasing the pH to 7.0 with 1 M NaOH. The supernatant was dialyzed against 10 mM ammonium acetate pH 5.0, then subjected to fast flow anion-exchange chromatography on a 1 mL Q-Sepharose column with a 10-600 mM ammonium acetate pH 5.0 gradient generated over 20 column volumes. Eluted fractions were analyzed by 19% SDS-PAGE followed by Coomassie staining. Fractions containing E2p were pooled and dialyzed against PBS pH 7.4. Protein concentration was measured using the BCA (bicinchoninic acid) assay with BSA as the standard.

Bacterial Expression and Purification of HP1-Peptide Fusions

*E. coli* BL21(DE3) cells transformed with one of the HP1 expression plasmids were amplified in LB media supplemented with 100 μg/mL ampicillin at 37° C. until $OD_{600}$ 0.9. Protein expression was induced with 100 μg/mL IPTG for 4 hours at 30° C. Cells were harvested by centrifugation and purified as described above for LplA. Purification fractions were analyzed by 16% SDS-PAGE followed by Coomassie staining. Fractions containing HP1-peptide protein were pooled and dialyzed against PBS pH 7.4. Protein concentration was measured using the BCA assay with BSA as the reference standard.

Measurement of LplA-Probe Ligation Kinetics (FIG. 2B)

To measure the $k_{cat}$ for LplA ligation of lipoic acid to E2p, 50 nM LplA was combined with 200 μM E2p, 750 μM lipoic acid, 1 mM ATP, and 2 mM magnesium acetate in 25 mM sodium phosphate pH 7.0. The reaction was initiated with addition of 1 mM ATP to the pre-warmed (30° C.) mixture. The reaction was incubated at 30° C., and 90 μL aliquots were removed every 5 minutes and quenched with 50 mM EDTA (final concentration). Samples were analyzed by C18 reverse-phase HPLC as described in the "Methods" section. Measurements were performed in triplicate. A calibration curve was obtained that correlated the ratio of integrated HPLC peak areas (E2p:E2p-probe) to the actual protein ratio, in order to compensate for differences in the extinction coefficients of E2p and lipoylated E2p. The amount of product obtained at each time point was plotted against time, to obtain the $V_{max}$ of the reaction. From this, the $k_{cat}$ value was obtained using the equation $V_{max}=k_{cat}[E]_{total}$.

To measure the $K_m$ and $k_{cat}$ for ligation of azide 7, 200 nM LplA was combined with 200 μM E2p, 1 mM ATP, 2 mM magnesium acetate in 25 mM sodium phosphate pH 7.0, and various concentrations of azide 7 (25, 50, 66, 100, 240, 360 and 750 μM). 90 μL aliquots were removed from the 30° C. reactions at 5 minutes intervals, up to 30 minutes, and quenched with 50 mM EDTA (final concentration). Samples were analyzed by HPLC as above. The amount of product obtained at each time point was plotted against time, to obtain the initial velocity for each concentration of azide 7. The collection of initial velocities ($V_0$) was then plotted against azide 7 concentration (25-750 μM), and fit to the Michaelis-Menten equation ($V_0=V_{max}$[azide 7]/($K_m$+[azide 7])), using Origin 6.1 software, to obtain the $K_m$ for azide 7. From the $V_{max}$ value, $k_{cat}$ was calculated using the equation $V_{max}=k_{cat}[E]_{total}$.

Figure 2A:
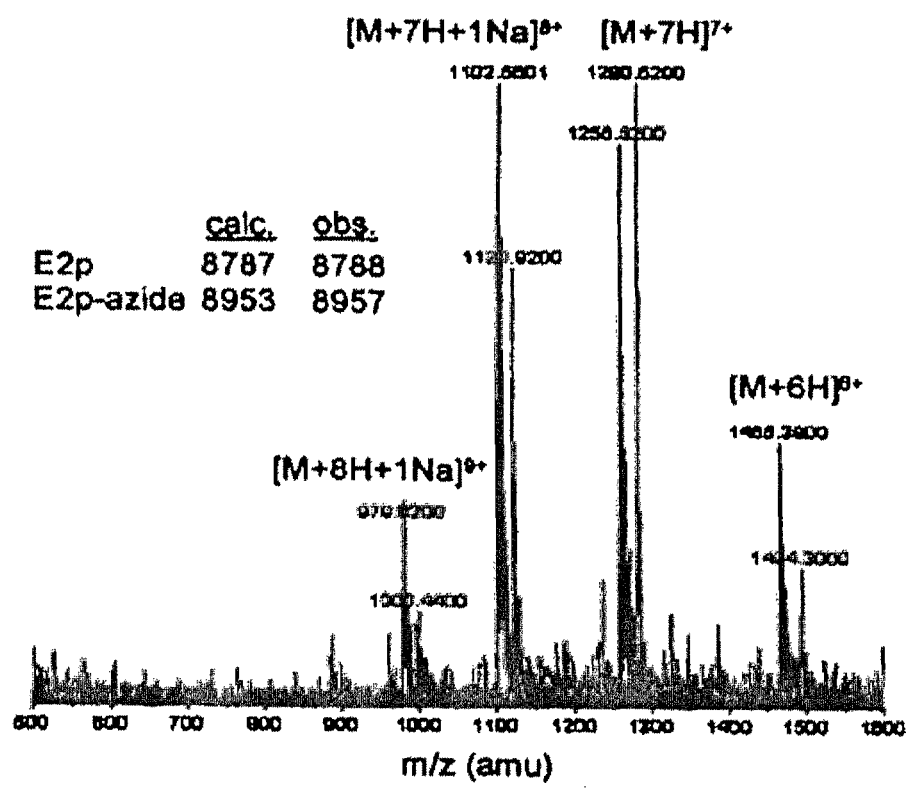
FIG. 2A shows a mass spectrometric analysis of E2p-azide 7 conjugate (starred product in HPLC trace shown in FIG. 5). The spectrum for E2p is shown for reference. Peaks for the +6, +7, +8, and +9 charge states are observed.
Figure 2B:
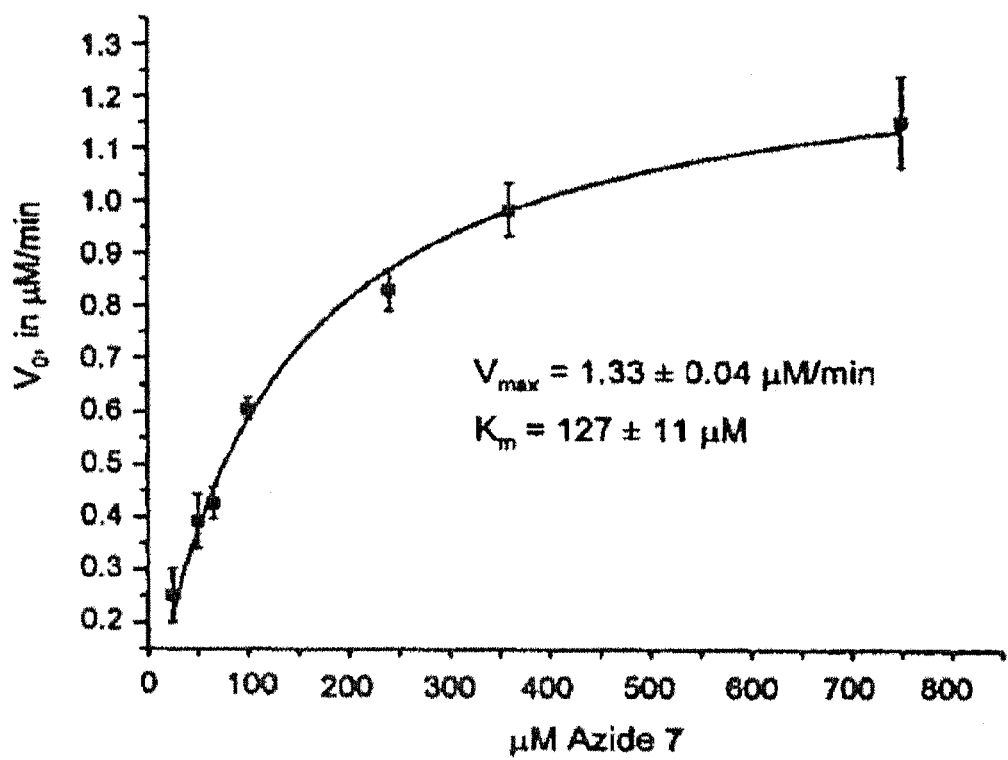
FIG. 2B is a Michaelis-Menten plot for azide 7 ligation to E2p. Initial rates are shown as a function of azide 7 concentration. LplA concentration was 200 nM. The measured $k_{cat}$ was $0.111 \pm 0.003$ $s^{-1}$. Each data point represents the average of three independent experiments. Error bars, ±1 s.d.

Mass-Spectrometric Analysis of E2p-Azide 7 Conjugate (FIG. 2A)

2 µM LplA was combined with 200 µM E2p, 350 µM azide 7, 1 mM ATP, and 2 mM magnesium acetate in 25 mM sodium phosphate pH 7.0. The ligation reaction was allowed to proceed to completion by incubating at 30° C. for 2 hours. The reaction mixture was desalted by extensive dialysis against water (2×4 h, followed by overnight dialysis). Thereafter, the sample was diluted to a final concentration of 25 µM E2p-azide 7 in 50% methanol with 2% acetic acid. Mass spectra were recorded under the positive enhanced multi-charge mode of an ESI-MS.

HPLC Analysis of LplA Modification of HP1-Peptide Fusions (FIG. 3)

To compare the conversion rates for different peptide substrates, reactions were assembled as follows: 1.5 µM LplA, 150 µM HP1-peptide fusion, 750 µM azide 7, 1 mM ATP, and 2 mM magnesium acetate in 25 mM sodium phosphate pH 7.0. Reactions were incubated at 30° C. for 2 hours, then quenched with 50 mM EDTA (final concentration), and subsequently analyzed by C18 reverse-phase HPLC using a gradient of 30-45% acetonitrile in water with 0.1% trifluoroacetic acid over 20 minutes with a 1 mL/minute flow rate. Retention times for unmodified HP1-peptide fusions ranged from 8-12 minutes, and shifted to 16-21 minutes after ligation to azide 7. Measurements were performed in triplicate. The extent of modification was calculated from the ratio of HP1-peptide-azide 7 peak area to the sum of (HP1-peptide+HP1-peptide-azide 7) peak areas. The conversion with HP1-peptide 8 was normalized to 100% and other conversions were reported relative to this.

Measurement of $k_{cat}$ for LplA-Catalyzed Azide 7 Ligation to LAP

To measure the $k_{cat}$ for LplA-catalyzed ligation of azide 7 to LAP, the reaction conditions were as follows: 2 µM LplA, 1.3 mM LAP-HP1 (N-terminal fusion of peptide 10 to HP1), 750 µM azide 7, 1 mM ATP, and 2 mM magnesium acetate in 25 mM sodium phosphate pH 7.0. The reaction was initiated with addition of 1 mM ATP to the pre-warmed 30° C. mixture. The mixture was incubated at 30° C., and 10 µL aliquots were removed every 5 minutes and quenched with 50 mM EDTA (final concentration). Samples were analyzed by C18 reverse-phase HPLC as above. The amount of product obtained at each time point was plotted against time, to obtain the $V_{max}$ of the reaction. From this, the $k_{cat}$ value was obtained using the equation $V_{max}=k_{cat}[E]_{total}$.

Labeling of Cell Surface LAP-CFP-TM with OCT-Biotin

HEK 293T cells were transfected with the LAP-CFP-TM plasmid using Lipofectamine 2000. After 36-48 hours at 37° C., the cells were washed twice with fresh growth media (DMEM supplemented with 10% FBS and 1% penicillin/streptomycin). Enzymatic ligation of azide 7 was performed in complete growth media with 10 µM LplA, 350 µM azide 7, 1 mM ATP, and 5 mM magnesium acetate for 15 minutes at 32° C. Cells were then rinsed three times with growth media, and incubated for 15 minutes at 32° C. with 250 µM OCT-biotin. Thereafter, the cells were washed twice with growth media and incubated with streptavidin-Alexa Fluor 568 (30 µg/ml, prepared as previously described[16]) for 15 minutes at 21° C. The cells were washed once with growth media at 21° C. and twice with ice-cold DPBS, pH 7.4, and imaged in the same buffer on a Zeiss Axiovert 200M as described under "Methods".

Labeling of Cell Surface AP-CFP-TM with BirA and Ketone

HEK 293T cells were transfected with AP-CFP-TM plasmid (6) using Lipofectamine 2000. After 36-48 hours at 37° C., the cells were washed twice with DPBS pH 7.4 and labeling was performed as previously reported (6). Briefly, enzymatic ligation of ketone to AP-CFP-TM was performed in DPBS pH 7.4, with 0.2 µM BirA, 1 mM ketone 1 (6), 1 mM ATP, and 5 mM magnesium acetate for 60 minutes at 32° C. Cells were then washed twice with DPBS, pH 6.2 and incubated for 60 minutes at 16° C. (to reduce endocytosis) with 1 mM benzophenone-biotin-hydrazide (6) in DPBS pH 6.2. Thereafter, the cells were washed twice with ice-cold DPBS pH 7.4, and incubated with 30 µg/mL streptavidin-Alexa Fluor 568 in DPBS pH 7.4 and 1% BSA for 15 minutes at 4° C. The cells were washed twice with DPBS pH 7.4, and imaged in the same buffer as described above.

Labeling of Cell Surface Q2-CFP-TM with Transglutaminase

HEK 293T cells were transfected with Q2-CFP-TM plasmid (7) using Lipofectamine 2000. After 36-48 hours at 37° C., the cells were washed twice with DMEM, and labeling was performed as previously reported (7). Briefly, enzymatic ligation of biotin cadaverine to Q2-CFP-TM was performed in DMEM, with 0.3 µM or 1 µM guinea pig liver transglutaminase (TGase, NZyme BioTec GmbH), 0.5 mM biotin cadaverine, and 12 mM $CaCl_2$ for 30 minutes at 37° C. Cells were then washed twice with DPBS pH 7.4, and incubated for 15 minutes at 4° C. (to reduce endocytosis) with 30 µg/mL streptavidin-Alexa Fluor 568 in DPBS pH 7.4, and 1% BSA. The cells were washed three times with ice-cold DPBS pH 7.4, and imaged in the same buffer as described above.

LplA labeling is superior to ketone/biotin ligase and transglutaminase labeling in speed, sensitivity, and specificity.

We previously reported two other methods for site-specific labeling of peptide-fused cell surface proteins with small molecule probes. In ketone/biotin ligase labeling, a 15-amino acid "acceptor peptide" (AP) tag is site-specifically conjugated to a ketone analog of biotin by E. coli biotin ligase (BirA) (6). The ketone is then selectively derivatized with a hydrazide- or hydroxylamine-conjugated fluorophore. Transglutaminase labeling uses the guinea pig liver transglutaminase to covalently ligate cadaverine-functionalized fluorophores to proteins fused to a 7-residue glutamine-containing "Q2-tag" recognition sequence for transglutaminase (7). We directly compared the speed, sensitivity, and specificity of LplA labeling to these methods in side-by-side labeling experiments.

LAP-CFP-TM-expressing HEK cells were labeled with LplA and azide 7 for 15 minutes, followed by OCT-PEG-biotin for 15 minutes, followed by streptavidin (SA)-Alexa Fluor 568 conjugate for 15 minutes. AP-CFP-TM-expressing HEK cells were labeled with BirA and ketone (6) for 60 minutes, followed by biotin-benzophenone-hydrazide (6) for 60 minutes, followed by streptavidin-Alexa Fluor 568 conjugate for 15 minutes. This optimized 2 hour 15 minutes labeling protocol was used to achieve similar signal to background intensity ratios as seen in previous LplA labeling experiments (total time 45 minutes). Due to the long labeling time, as well as the reduced pH and temperature required for the hydrazone formation step, many cells became unhealthy and rounded. AP-CFP-TM-expressing HEK cells were labeled with BirA and ketone (6) for 60 minutes, followed by Alexa Fluor 568 hydrazide for 20 minutes. No fluorophore conjugation was observed, and increasing the time of the second step or the concentration of Alexa Fluor 568 hydrazide increased the non-specific background (data not shown). This contrasts to the successful LplA-catalyzed fluorophore conjugation described in Example 2. One explanation for the difference in labeling sensitivity of these two methods is the faster second-order rate constant for the azide-alkyne [3+2] cycloaddition reaction compared to ketone-hydrazide ligation (5,8)

Transglutaminase (TGase) labeling was performed on HEK cells expressing the Q2-CFP-TM construct (7) under optimized conditions, using biotin cadaverine with 0.3 µM or 1 µM transglutaminase (7) for 30 minutes, followed by detection with streptavidin-Alexa Fluor 568 for 15 minutes. Negative controls were performed with the alanine mutant of the Q2 construct. Labeling was comparable to LplA ligation of OCT-biotin in speed and sensitivity. However, the specificity of transglutaminase labeling was highly variable and difficult to optimize. Specific labeling is seen with 0.3 µM transglutaminase, when comparing the Q2-CFP-TM image to the Q2(Ala)-CFP-TM negative control image. However, increasing the enzyme concentration by only 3-fold resulted in the loss of labeling specificity (right panels). By contrast, LplA was completely specific for the LAP sequence at enzyme concentrations ranging from 1 µM to 20 µM.

Determination of LplA Labeling Sensitivity with LAP-CFP-TM

We used the wedge method to estimate the concentration of CFP in single cells expressing the LAP-CFP-TM construct (6, 17). A wedge-shaped microchamber was constructed from three glass coverslips. The length along the x direction was 6.5 mm and the height of the chamber (z-direction) increased linearly from 0 to 150 µm. The chamber was filled with a solution of 10 µM purified CFP in PBS pH 7.4. The fluorescence of the wedge was imaged under conditions identical to those used for cellular imaging. We assumed an average cell thickness of 5 µm and therefore interpolated to the region of the wedge with thickness 5 µm and used the fluorescence intensity measured there as a reference standard for CFP concentration measured in single cells. Using the wedge for comparison, we imaged two samples of HEK and HeLa cells expressing LAP-CFP-TM. Examination of the CFP channel images for cells that display clear OCT-biotin labeling (signal to background ≥3:1) showed that the CFP concentrations ranged from 5 µM to >1 mM. We therefore concluded that cells expressing as little as 5 µM LAP-CFP-TM could be labeled by our method. This represents an upper limit to the labeling sensitivity of our methodology.

Orthogonality Test for Two-Color Labeling with LplA and BirA

HEK 293T cells were either singly transfected with LAP-GFP-LDLR or co-transfected with a mixture of AP-EGFR (or AP-EphA3) and CFP-pcDNA3 in a 6:1 ratio using Lipofectamine 2000. 24 hours after transfection, the cells were re-plated together in a 1:1 ratio. After further incubation for 24 hours at 37° C., the cells were washed twice with fresh growth media (DMEM with 10% FBS and 1% penicillin/streptomycin). Simultaneous enzymatic ligations of azide 7 and biotin were performed in complete growth media with 5 µM BirA, 10 µM LplA, 50 µM biotin, 350 µM azide 7, 1 mM ATP, and 5 mM magnesium acetate for 60 minutes at 32° C. Cells were then rinsed three times with growth media, and incubated for 20 minutes at 21° C. with 200-400 µM OCT-Cy3. Biotin was detected with streptavidin-QD655 (13 nM, Invitrogen) for 10 minutes at 4° C. Thereafter, the cells were washed once with ice-cold 1% BSA in DPBS, pH 7.4 and twice more with ice-cold DPBS, pH 7.4. Labeled cells were imaged as described above. The GFP filter set was 495/20 excitation, 515 dichroic, 530/30 emission; the QD655 filter set was 405/20, 585 dichroic, and 655/20 emission. LAP-GFP-LDLR cells were specifically labeled with Cy3, while AP-EGFR cells (indicated by CFP marker) were specifically labeled with QD655.

REFERENCES FOR EXAMPLE 1 AND FIGS. 1-4

1. Green, J. D., Laue, E. D., Perham, R. N., Ali, S. T. & Guest, J. R. Three-dimensional structure of a lipoyl domain from the dihydrolipoyl acetyltransferase component of the pyruvate dehydrogenase multienzyme complex of *Escherichia coli*. *J. Mol. Biol.* 248, 328-343 (1995).
2. Reche, P. & Perham, R. N. Structure and selectivity in post-translational modification: attaching the biotinyl-lysine and lipoyl-lysine swinging arms in multifunctional enzymes. *EMBO J.* 18, 2673-2682 (1999).
3. Dardel, F., Packman, L. C. & Perham, R. N. Expression in *Escherichia coli* of a sub-gene encoding the lipoyl domain of the pyruvate dehydrogenase complex of *Bacillus stearothermophilus*. *FEBS Lett.* 264, 206-210 (1990).
4. Saunders, W. S. et al. Molecular cloning of a human homologue of *Drosophila* heterochromatin protein HP1 using anti-centromere autoantibodies with anti-chromo specificity. *J. Cell Sci.* 104, 573-582 (1993).
5. Agard, N. J., Baskin, J. M., Prescher, J. A., Lo, A. & Bertozzi, C. R. A comparative study of bioorthogonal reactions with azides. *ACS Chem. Biol.* 1, 644-648 (2006).
6. Chen, I., Howarth, M., Lin, W. & Ting, A. Y. Site-specific labeling of cell surface proteins with biophysical probes using biotin ligase. *Nat. Methods* 2, 99-104 (2005).
7. Lin, C. W. & Ting, A. Y. Transglutaminase-catalyzed site-specific conjugation of small-molecule probes to proteins in vitro and on the surface of living cells. *J. Am. Chem. Soc.* 128, 4542-4543 (2006).
8. Nauman, D. A. & Bertozzi, C. R. Kinetic parameters for small-molecule drug delivery by covalent cell surface targeting. *Biochim. Biophys. Acta* 1568, 147-154 (2001).
9. Alper, P. B., Hung, S. C. & Wong, C. H. Metal catalyzed diazo transfer for the synthesis of azides from amines. *Tetrahedron Letters* 37, 6029-6032 (1996).
10. Scriven, E. F. V. & Turnbull, K. Azides: their preparation and synthetic uses. *Chemical Reviews* 88, 297-368 (1998).
11. Novis-Smith, W. & Beumel, J. Preparation of alkynes and dialkynes by reaction of mono-halo and dihaloalkanes with lithium acetylenide-ethylenediamine complex. *Synthetic Communications* 441-442 (1974).
12. Gama, L. & Breitwieser, G. E. Generation of epitope-tagged proteins by inverse polymerase chain reaction mutagenesis. *Methods Mol. Biol.* 182, 77-83 (2002).
13. Green, D. E., Morris, T. W., Green, J., Cronan, J. E., Jr. & Guest, J. R. Purification and properties of the lipoate protein ligase of *Escherichia coli*. *Biochem. J.* 309, 853-862 (1995).
14. Morris, T. W., Reed, K. E. & Cronan, J. E., Jr. Lipoic acid metabolism in *Escherichia coli*: the lplA and lipB genes define redundant pathways for ligation of lipoyl groups to apoprotein. *J. Bacteriol.* 177, 1-10 (1995).
15. Ali, S. T. & Guest, J. R. Isolation and characterization of lipoylated and unlipoylated domains of the E2p subunit of the pyruvate dehydrogenase complex of *Escherichia coli*. *Biochem. J.* 271, 139-145 (1990).
16. Howarth, M. et al. A monovalent streptavidin with a single femtomolar biotin binding site. *Nature Methods* 3, 267-273 (2006).
17. Adams, S. R. et al. New biarsenical ligands and tetracysteine motifs for protein labeling in vitro and in vivo: synthesis and biological applications. *J. Am. Chem. Soc.* 124, 6063-6076 (2002).

Example 2

Introduction

Live cell imaging is a powerful method for studying protein dynamics at the cell surface, but conventional probes, such as antibodies and fluorescent ligands, are bulky, interfere with protein function (1,2), or dissociate after internalization (3,4). To overcome these limitations, we developed a method to covalently tag any cell surface protein with any chemical probe with remarkable specificity. Through rational design, we re-directed a microbial lipoic acid ligase (LplA) (5) to specifically ligate an alkyl azide to an engineered LplA acceptor peptide (LAP) tag. The alkyl azide is then selectively derivatized with a cyclooctyne (6) conjugated to any probe of interest. We demonstrate the utility of this method by first labeling LAP fusion proteins expressed on the surface of living mammalian cells with Cy3, AlexaFluor568, and biotin. Next, we combined LAP-tagging with our previously reported tagging method (7,8) to simultaneously monitor the dynamics of two receptors, co-expressed in the same cell, with different fluorophores. Using a wound-healing assay, we found that while the LDL receptor maintains a uniform distribution on the cell surface, the ephrin receptor EphA3 is polarized to the leading edge. This methodology provides general access to biochemical and imaging studies of cell surface proteins, using small fluorophores introduced via a short peptide tag.

Methods

In Vitro LplA Activity Assays.

LplA reactions contained 2 µM LplA, 200 µM E2p, 350 µM probe, 1 mM ATP, 2 mM magnesium acetate, and 25 mM sodium phosphate pH 7.0. Reactions were incubated at 30° C. for 30 minutes, and then quenched with EDTA (final concentration 50 mM). Conversion to product was determined by HPLC on a $C_{18}$ reverse-phase column with a 40-57% gradient of acetonitrile in water with 0.1% trifluoroacetic acid over 20 minutes (flow rate 1.0 mL/minute). Unmodified E2p had a retention time of ~12 minutes while E2p-probe conjugates eluted at 15-18 minutes. Percent conversion to product was calculated from the ratio of the E2p-probe peak area to the sum of (E2p+E2p-probe) peak areas. All measurements were performed in triplicate.

LplA Specificity Test on Mammalian Lysate.

Human embryonic kidney (HEK) 293T cells were transfected with LAP-CFP-pcDNA3 plasmid using Lipofectamine 2000 (1 µg DNA/well of a 6-well plate). Lysates were generated 48 hours later by hypotonic lysis to minimize protease release, as follows. Cells were lifted from the plates, concentrated by centrifugation, and resuspended in 1 mM HEPES pH 7.5, 5 mM magnesium chloride, 1 mM phenylmethylsulphonyl fluoride, and protease inhibitor cocktail (Calbiochem). After incubation at 4° C. for 10 minutes, the cells were lysed by vigorous vortexing for 2 minutes at 21° C. Crude lysate was clarified by centrifugation, and stored at −80° C. Lysate was labeled by incubating at 30° C. for 10 hours with 25 mM sodium phosphate pH 7.0, 1 µM LplA, 250 µM azide 7, 1 mM ATP, and 4 mM magnesium acetate. Thereafter, Staudinger ligation was performed by adding FLAG-phosphine (14) to a final concentration of 500 µM, and incubating at 30° C. for 16 hours. Each reaction sample was then divided into thirds. The first third was analyzed by 12% SDS-PAGE followed by Western blotting with anti-FLAG (M2)-peroxidase antibody conjugate (Sigma, 1:1000 dilution). The second sample was analyzed by 12% SDS-PAGE followed by Coomassie staining. The last third was analyzed by 12% SDS-PAGE without boiling the samples, in order to prevent unfolding of CFP, and in-gel fluorescence was visualized on a Storm 860 instrument (Amersham).

Live Cell Labeling with Fluorescent Probes.

HEK 293T cells were transfected with the LAP-CFP-TM expression plasmid using Lipofectamine 2000. After 36-48 hours at 37° C., the cells were washed twice with fresh growth media (Dulbecco's Modified Eagle's Medium with 10% fetal bovine serum and 1% penicillin/streptomycin). Enzymatic ligation of azide 7 was performed in complete growth media with 10 µM LplA, 350 µM azide 7, 1 mM ATP, and 5 mM magnesium acetate for 60 minutes at 32° C. Cells were rinsed three times with growth media, and incubated for 20 minutes at 21° C. with 200-400 µM OCT-Cy3 or 100-200 µM OCT-AlexaFluor568. Thereafter, the cells were washed once with growth media, twice with a 1% bovine serum albumin (BSA) solution in Dulbecco's Phosphate-Buffered Saline (DPBS) pH 7.4, and twice more with DPBS alone. Labeled cells were imaged in the same buffer on a Zeiss Axiovert 200M inverted epifluorescence microscope using a 40× oil-immersion lens. CFP (420/20 excitation, 450 dichroic, 475/40 emission), Cy3 and AlexaFluor568 (560/20 excitation, 585 dichroic, 605/30) and differential interference contrast (DIC) images (630/10 emission) were collected and analyzed using Slidebook software (Intelligent Imaging Innovations). Fluorescence images were normalized to the same intensity range. Acquisition times ranged from 10-250 milliseconds.

Two-Color Live Cell Labeling with LplA and Biotin Ligase.

HEK 239T cells were co-transfected with the LAP-LDLR and AP-EGFR (16) plasmids in a 1:2 ratio, or with the LAP-LDLR and AP-EphA3 (a gift from M. Lackmann, Monash University) plasmids in a 2:1 ratio. 24 hours after transfection, the cells were wounded with a pipet tip and allowed to heal over 16-24 hours. For labeling, cells were washed twice with complete growth media, and then incubated with 5 µM BirA, 10 µM LplA, 50 µM biotin, 350 µM azide 7, 1 mM ATP, and 5 mM magnesium acetate for 60 minutes at 32° C. Cells were then rinsed three times with growth media, and incubated for 20 minutes at 21° C. with 200-400 µM OCT-Cy3. Biotin was detected by staining with 50 µg/mL monovalent streptavidin-AlexaFluor488 (8) for 10 minutes at 4° C. The cells were washed once with ice-cold 1% BSA in DPBS pH 7.4, then twice with ice-cold DPBS, before imaging in the same buffer using the configuration described above. The AlexaFluor488 filter set was 495/20 excitation, 515 dichroic, 530/30 emission.

Results and Discussions

Fluorescent labeling of cell surface proteins enables imaging of the trafficking and function of receptors, channels, and transporters. Many protein labeling methods have been developed in recent years (9), but none currently allows the covalent attachment of small fluorophores of any structure onto cell surface proteins modified only by a small peptide tag, with short labeling times and with extremely high specificity over a wide range of expression levels and labeling conditions. To address this shortcoming, we developed a new protein labeling method based on the *E. coli* enzyme lipoic acid ligase (LplA) (5). In *E. coli*, LplA catalyzes the ATP-dependent covalent ligation of lipoic acid to one of three proteins involved in oxidative metabolism [E2p, E2o, and H-protein (5)] (FIG. 5A, top). LplA naturally exhibits extremely high sequence specificity, but previous work showing that the enzyme accepts octanoic acid, 6-thio-octanoic acid, and selenolipoic acid in place of lipoic acid (5) suggest that the small-molecule binding site has considerable plasticity. To harness LplA for fluorescent labeling, we re-engineered the system in three stages. First, through synthesis and testing of ten different substrate analogs, we discovered an alkyl azide substrate that can be efficiently used by LplA in place of lipoic acid. Once ligated to the target protein, the azide functional group can be selectively derivatized with any fluorescent probe conjugated to a cyclooctyne reaction partner (6) (FIG. 5A). Second, to create a minimally invasive tag to direct the ligation of the alkyl azide, we engineered, through iterative cycles of rational design, a 22-amino acid replacement for LplA's natural protein substrates, which can be fused to the N- or C-terminus of any protein of interest. Third, we tested the specificity of LplA in the mammalian cell context and found no background labeling of endogenous proteins.

For the first stage of LplA engineering, we considered a range of small molecule structures to replace lipoic acid. Direct ligation of a fluorophore would offer a simpler and shorter labeling procedure, but incorporation of a "functional group handle" is more feasible due to the small size of the lipoate binding pocket, and provides greater versatility for subsequent incorporation of probes of any structure. Many functional group handles have been used in chemical biology, including ketones, organic azides, and alkynes (10). Organic azides are the most suitable for live cell applications, because the azide group is both abiotic and non-toxic in animals and can be selectively derivatized under physiological conditions (without any added metals or cofactors) with cyclooctynes, which are also unnatural (6). To test if LplA could accept an azide substrate in place of lipoic acid, we synthesized a panel of alkyl azide carboxylic acids of varying lengths (FIG. 1), and tested them for ligation onto a 9 kDa lipoyl domain derived from the full-length E2p protein (11) (abbreviated "E2p") using an HPLC assay. As additional probes of the lipoate binding pocket we also synthesized a series of alkyne carboxylic acids (FIG. 1). FIG. 5B shows that all probes were incorporated by LplA to some degree, but the efficiency of ligation exhibited a clear length-dependence, with azide 7 giving the fastest kinetics. FIG. 5Cc shows the HPLC trace associated with azide 7 ligation to E2p, in addition to negative control reactions with LplA or ATP omitted. We collected the product peak (starred) from the top trace and analyzed it by mass-spectrometry, which confirmed that one molecule of azide 7 had been site-specifically conjugated to E2p (FIG. 2). We also measured the kinetics of azide 7 ligation to E2p (FIG. 2), and compared the values to those of lipoic acid ligation. The $k_{cat}$ values were only slightly different ($0.111\pm0.003$ s$^{-1}$ vs $0.253\pm0.003$ s$^{-1}$) but the $K_m$ increased 75- or 30-fold for azide 7 ($127\pm11$ µM) compared to lipoic acid [$1.7$ µM (5) or $4.5$ µM (12)]. As seen below, however, it is straightforward and non-toxic to provide azide 7 at concentrations higher than 127 µM for live cell labeling, thus maximizing the rate of ligation.

For the second stage of engineering, we wished to design a peptide substrate for LplA to replace the protein substrates. It was necessary for the peptide to be fully transposable (recognized when fused to the N- or C-terminal ends of any protein) and to be recognized by LplA with similar efficiency to the natural protein substrates. As described in FIG. 3, we accomplished this through multiple rounds of rational design. A major challenge was presented by the fact that E2p presents the lysine modification site at the tip of a sharp hairpin turn (13), a conformation that is difficult to recapitulate in a peptide. Nevertheless, we designed an initial panel of peptides by analyzing lipoate acceptor proteins from different species, as well as structurally-related biotin acceptor proteins. Peptides that were active in the initial screen were then improved through site-directed mutagenesis and tested for recognition at either terminus of a model protein. The final 22-amino acid sequence, called the LplA acceptor peptide (LAP), had a $k_{cat}$ of $0.048\pm0.001$ s$^{-1}$, only 2.3-fold lower than the corresponding $k_{cat}$ for full-length E2p.

Our third task was to assess the specificity of LplA in the mammalian cell context. To do this, we created a LAP fusion to cyan fluorescent protein (CFP), and expressed it in human embryonic kidney (HEK) cells. HEK lysates were then labeled with LplA, azide 7, and ATP, and the ligated azide was detected by western blot, after functionalization with a FLAG peptide via the Staudinger ligation (14). FIG. 6 shows that in the presence of thousands of mammalian proteins in lysate, only LAP-CFP is labeled by LplA. The expression level of LAP-CFP is so low that it cannot be seen above endogenous proteins in the Coomassie-stained gel. Negative controls with LplA replaced by a catalytically inactive mutant, or LAP-CFP replaced by an alanine point mutant at the lysine modification site, show that labeling depends on the presence of LplA and an intact LAP sequence. This experiment and the live cell labeling experiments described below demonstrate that LplA is a remarkably specific enzyme at the cell surface, and possibly within the cytosol as well.

To test our newly engineered small molecule and peptide substrates for LplA in the live cell context, we first created an artificial construct by fusing LAP to CFP, and then fusing this in turn to the extracellular side of the transmembrane (TM) domain of the PDGF receptor. We also synthesized conjugates of our previously reported mono-fluorinated cyclooctyne (6) (OCT) to two bright, red-emitting, and membrane-impermeant fluorophores, AlexaFluor568 and Cy3 (FIG. 4).

To perform labeling, LAP-CFP-TM was expressed in HEK cells, and 350 µM azide 7 was added in the presence of LplA for 1 hour, followed by one of the fluorophore-OCT conjugates for 20 minutes. A LAP-CFP fusion was targeted to the cell surface using a transmembrane (TM) domain. Cell-surface LAP was first labeled with azide 7 by LplA, and the introduced azide was then labeled with a cyclooctyne probe conjugated to Cy3 or AlexaFluor568. Negative controls with azide 7 omitted from the labeling reaction, or with the LAP-CFP-TM replaced by its alanine point mutant.

The results from these studies showed that transfected cells (indicated by CFP fluorescence) were labeled with AlexaFluor568 or Cy3, while untransfected cells were not labeled. Interestingly, labeling with AlexaFluor568 generated higher background than Cy3 labeling, due to faster non-specific internalization of the probe. We performed additional negative controls with omission of azide 7 or replacement of LAP-CFP-TM by its alanine mutant, and observed no labeling in either case. Unlike sodium azide, organic azides such as the clinically approved drug AZT (15) are not known to be toxic to cells, but we nevertheless examined the effect of 24-hour exposure to azide 7 on mitochondrial respiration, and found no effect at concentrations less than 750 µM.

We also compared the speed, sensitivity, and specificity of LplA labeling to two other peptide-based labeling methods previously described by our lab. Biotin ligase (BirA)/ketone tagging makes use of a ketone isostere of biotin, which can be functionalized with hydrazide conjugates to label proteins fused to a 15-amino acid "acceptor peptide" (AP) (16). Transglutaminase labeling attaches cadaverine-functionalized fluorophores to a glutamine-containing peptide recognition sequence (17). For the comparison experiments, we used LplA to label LAP-CFP-TM with azide 7, followed by OCT-biotin, and followed by streptavidin-AlexaFluor568 to detect the biotin. A total labeling time of only 20 minutes was required for all three steps, in order to achieve a signal to background ratio $\geq 3:1$. In contrast, BirA/ketone labeling of an analogous AP-CFP-TM construct with a biotin-hydrazide compound followed by streptavidin detection required 2 hours and 15 minutes to achieve a similar signal to background ratio. We also quantified the sensitivity of LplA labeling using the wedge method (18) and determined that cells expressing as little as 5 µM LAP-CFP-TM could be specifically labeled with OCT-biotin, with a signal to background ratio $\geq 3:1$. Similar experiments, were performed and demonstrated that LplA is also superior to transglutaminase, particularly in terms of labeling specificity under a wide range of conditions.

To illustrate the use of LplA labeling for imaging actual receptors, we created a LAP fusion to the low-density lipoprotein receptor (LDLR), which functions in the uptake of cholesterol in peripheral tissues of the body (19), and we established that LAP-LDLR could be labeled with OCT-Cy3 or OCT-biotin in HEK cells, even when expressed at levels matching endogenous LDLR (data not shown). We then wished to image LAP-LDLR in the context of a biological assay. For many imaging studies, it is desirable to visualize two different receptors at once in the same cell, in order to compare their distribution or trafficking patterns. To develop this capability, we investigated the compatibility of LplA labeling with BirA/streptavidin targeting. Unlike BirA/ketone labeling, BirA/streptavidin targeting (7,8) makes use of site-specific biotin ligation onto AP-tagged proteins, followed by recognition with streptavidin-fluorophore conjugates. While the use of streptavidin increases the total size of the label, the femtomolar affinity of the biotin-streptavidin interaction makes this labeling approach much faster and much more sensitive than BirA/ketone labeling (7).

*E. coli* LplA and biotin ligase are mechanistically related, and their natural acceptor proteins share some structural and sequence overlap (20). However, the engineered LAP and AP sequences are dissimilar, as are the azide 7 and biotin structures. To test the orthogonality of these two labeling methods, we prepared separate dishes of HEK cells expressing LAP-LDLR (with a GFP tag to serve as a transfection marker), or AP-EGFR [AP fused to the extracellular N-terminus of the EGF receptor (16)] together with a CFP transfection marker. After 16-24 hours of expression, the cells were re-plated together in a single dish. We performed labeling by first adding a mixture of LplA, BirA, azide 7, biotin, and ATP to the cells. Thereafter, OCT-Cy3 was added to derivatize the azide, and streptavidin was added to detect the biotin. Results demonstrated that cells expressing LAP-LDLR were selectively labeled with Cy3, while cells expressing AP-EGFR were selectively labeled with streptavidin. The same results were obtained using LAP-LDLR in combination with an AP-tagged receptor for ephrinA3 (AP-EphA3). Thus, simultaneous labeling of cells with LplA and BirA is possible, without sacrificing the extremely high specificity of each system.

We then used this two-color labeling protocol to image LAP- and AP-fused receptors co-expressed within the same cell. EGF receptor and EphA3 are both known to function in cell migration (21,22), and thus we performed imaging on cells migrating toward an artificial wound. HEK cells were co-transfected with either LAP-LDLR and AP-EGFR, or LAP-LDLR and AP-EphA3. After 16-24 hours of expression, the confluent cells were wounded with a pipet tip. We allowed the wound to partially close over 12-18 hours, and then performed s simultaneous labeling with Cy3, and AlexaFluor488 conjugated to monovalent streptavidin (8). HEK cells co-expressing a LAP-LDLR fusion and either AP-EGFR or AP-EphA3 were labeled during wound healing by first treating with LplA, BirA, azide 7, and biotin, followed by OCT-Cy3 to derivatize the azide, followed by monovalent streptavidin-AlexaFluor488 (8) to detect the biotin. The Cy3 results showed the non-polarized distribution of surface LAP-LDLR. The AlexaFluor488 results showed the polarized distribution of AP-EGFR and AP-EphA3 at the wound edge. CFP is a transfection marker. The results showed that Cy3-labeled LDLR was evenly distributed on the surface of the HEK cells, whereas AlexaFluor488-labeled EGFR and EphA3 were both asymmetrically concentrated at the leading edge of the polarized cells. The same patterns were also observed when the LAP and AP tags were swapped (AP-LDLR and LAP-EGFR), suggesting that the localization patterns do not reflect artifacts of AP and LAP labeling.

While the polarization of AP-EGFR to the leading edge of migrating cells was expected, and has previously been observed using antibody detection (23), the pattern of AP-EphA3 staining is surprising. Previous work has shown that trans interactions between EphA3 and ephrin ligand expressed on the surface of contacting cells play a role in developmental cell migration (24) and tumor invasion (25). However, it is unclear that un-liganded EphA3 should function in migratory processes. Our observation of EphA3 accumulation at the free, leading edge of polarized cells suggests that unactivated EphA3 may play a role in cell signaling, or that EphA3 may be constitutively linked to the actin cytoskeleton.

In summary, we have developed new methodology for labeling cell surface proteins fused to a 22-amino acid recognition sequence for *E. coli* LplA. Small, non-crosslinking probes such as Cy3, AlexaFluor, and biotin can be site-specifically and covalently conjugated to the LAP peptide in as little as 20 minutes. An important feature of our methodology is its generality; any cell surface protein in any cell type can be labeled with any chemical moiety that can be functionalized with a cyclooctyne.

Many new protein labeling methods have been developed in recent years (9), and a survey of these techniques reveals that a general trade-off exists between labeling specificity and tag size. Protein-based tags, such as SNAP/AGT (26) generally give higher labeling specificity than peptide tags, such as FlAsH (27). However, protein tags have greater potential to interfere with protein folding, trafficking, and activity, as GFP often does (28,29). We and others [for example, ACP/PCP labeling methodology (30)] have tried to bridge the requirements of small tag size and high labeling specificity, by making use of enzyme ligases. By capitalizing on the intrinsic sequence specificity of enzymes such as biotin ligase and LplA, highly specific probe conjugation can be achieved, without sacrificing the small size of the directing tag.

In previous work with BirA, we found that a ketone isostere of biotin could be accepted (16), but not compounds with more dissimilar structures, such as alkyne and azide derivatives of biotin, due to the structural requirements of the biotin binding pocket. In contrast, LplA exhibits much more relaxed specificity for its small molecule substrate, while maintaining extremely high specificity for its protein or peptide substrate (5). This property allowed us to harness LplA for unnatural ligation reactions in this study. Important next challenges will be to extend this methodology to labeling of intracellular protein targets and to re-engineer LplA for one-step-ligation of fluorophore or photoaffinity probes.

We also used LplA in combination with biotin ligase to image two different receptors in the same cell. Many problems in receptor biology would benefit from simultaneous imaging of two or more different proteins in the same living cell, instead of separate experiments involving one-color labeling of each receptor. The combination of LplA and BirA tagging, which can be performed simultaneously due to the orthogonality of the labeling reaction components, will provide access to such experiments.

REFERENCES FOR EXAMPLE 2 AND FIGS. 5-6

1. Debant, A., Ponzio, G., Clauser, E., Contreres, J. O. & Rossi, B. Receptor cross-linking restores an insulin metabolic effect altered by mutation on tyrosine 1162 and tyrosine 1163. *Biochemistry* 28, 14-17 (1989).
2. Weiss, A. & Littman, D. R. Signal transduction by lymphocyte antigen receptors. *Cell* 76, 263-274 (1994).
3. Anderson, R. G., Brown, M. S., Beisiegel, U. & Goldstein, J. L. Surface distribution and recycling of the low density lipoprotein receptor as visualized with antireceptor antibodies. *J. Cell Biol.* 93, 523-531 (1982).
4. Barak, L. S. & Webb, W. W. Fluorescent low density lipoprotein for observation of dynamics of individual receptor complexes on cultured human fibroblasts. *J. Cell Biol.* 90, 595-604 (1981).
5. Green, D. E., Morris, T. W., Green, J., Cronan, J. E., Jr. & Guest, J. R. Purification and properties of the lipoate protein ligase of *Escherichia coli*. *Biochem. J.* 309, 853-862 (1995).
6. Agard, N. J., Baskin, J. M., Prescher, J. A., Lo, A. & Bertozzi, C. R. A comparative study of bioorthogonal reactions with azides. *ACS Chem. Biol.* 1, 644-648 (2006).
7. Howarth, M., Takao, K., Hayashi, Y. & Ting, A. Y. Targeting quantum dots to surface proteins in living cells with biotin ligase. *Proc. Natl. Acad. Sci. U.S. A* 102, 7583-7588 (2005).
8. Howarth, M. et al. A monovalent streptavidin with a single femtomolar biotin binding site. *Nature Methods* 3, 267-273 (2006).
9. Marks, K. M. & Nolan, G. P. Chemical labeling strategies for cell biology. *Nat. Methods* 3, 591-596 (2006).
10. Prescher, J. A. & Bertozzi, C. R. Chemistry in living systems. *Nat. Chem. Biol.* 1, 13-21 (2005).
11. Ali, S. T. & Guest, J. R. Isolation and characterization of lipoylated and unlipoylated domains of the E2p subunit of the pyruvate dehydrogenase complex of *Escherichia coli*. *Biochem. J.* 271, 139-145 (1990).
12. Fujiwara, K. et al. Crystal structure of lipoate-protein ligase A from *Escherichia coli*. Determination of the lipoic acid-binding site. *J. Biol. Chem.* 280, 33645-33651 (2005).
13. Green, J. D., Laue, E. D., Perham, R. N., Ali, S. T. & Guest, J. R. Three-dimensional structure of a lipoyl domain from the dihydrolipoyl acetyltransferase component of the pyruvate dehydrogenase multienzyme complex of *Escherichia coli*. *J. Mol. Biol.* 248, 328-343 (1995).
14. Kiick, K. L., Saxon, E., Tirrell, D. A. & Bertozzi, C. R. Incorporation of azides into recombinant proteins for chemoselective modification by the Staudinger ligation. *Proc. Natl. Acad. Sci. U.S. A* 99, 19-24 (2002).
15. Griffin, R. J. The medicinal chemistry of the azido group. *Prog. Med. Chem.* 31, 121-232 (1994).
16. Chen, I., Howarth, M., Lin, W. & Ting, A. Y. Site-specific labeling of cell surface proteins with biophysical probes using biotin ligase. *Nat. Methods* 2, 99-104 (2005).
17. Lin, C. W. & Ting, A. Y. Transglutaminase-catalyzed site-specific conjugation of small-molecule probes to proteins in vitro and on the surface of living cells. *J. Am. Chem. Soc.* 128, 4542-4543 (2006).
18. Adams, S. R. et al. New biarsenical ligands and tetracysteine motifs for protein labeling in vitro and in vivo: synthesis and biological applications. *J. Am. Chem. Soc.* 124, 6063-6076 (2002).
19. Willnow, T. E. The low-density lipoprotein receptor gene family: multiple roles in lipid metabolism. *J. Mol. Med.* 77, 306-315 (1999).
20. Reche, P. & Perham, R. N. Structure and selectivity in post-translational modification: attaching the biotinyl-lysine and lipoyl-lysine swinging arms in multifunctional enzymes. *EMBO J.* 18, 2673-2682 (1999).
21. Pasquale, E. B. Eph receptor signalling casts a wide net on cell behaviour. *Nat. Rev. Mol. Cell Biol.* 6, 462-475 (2005).
22. Singh, A. B. & Harris, R. C. Autocrine, paracrine and juxtacrine signaling by EGFR ligands. *Cell Signal.* 17, 1183-1193 (2005).
23. Tuli, S. S. et al. Immunohistochemical localization of EGF, TGF-alpha, TGF-beta, and their receptors in rat corneas during healing of excimer laser ablation. *Curr. Eye Res.* 31, 709-719 (2006).
24. Flanagan, J. G. & Vanderhaeghen, P. The ephrins and Eph receptors in neural development. *Annu. Rev. Neurosci.* 21, 309-345 (1998).
25. Wimmer-Kleikamp, S. H. & Lackmann, M. Eph-modulated cell morphology, adhesion and motility in carcinogenesis. *IUBMB. Life* 57, 421-431 (2005).
26. George, N., Pick, H., Vogel, H., Johnsson, N. & Johnsson, K. Specific labeling of cell surface proteins with chemically diverse compounds. *J. Am. Chem. Soc.* 126, 8896-8897 (2004).
27. Griffin, B. A., Adams, S. R. & Tsien, R. Y. Specific covalent labeling of recombinant protein molecules inside live cells. *Science* 281, 269-272 (1998).
28. Brock, R., Hamelers, I. H. & Jovin, T. M. Comparison of fixation protocols for adherent cultured cells applied to a GFP fusion protein of the epidermal growth factor receptor. *Cytometry* 35, 353-362 (1999).
29. McLean, A. J. & Milligan, G. Ligand regulation of green fluorescent protein-tagged forms of the human beta(1)- and beta(2)-adrenoceptors; comparisons with the unmodified receptors. *Br. J. Pharmacol.* 130, 1825-1832 (2000).
30. Zhou, Z. et al. Genetically encoded short peptide tags for orthogonal protein labeling by Sfp and AcpS phosphopantetheinyl transferases. *ACS Chem. Biol.* 2, 337-346 (2007).

Example 3

Synthesis of Resorufin Substrate

The structures of lipoic acid anologs resorufin A and resorufin B and their synthetic scheme are shown in FIG. 8.

To prepare substituted resofutin A, i.e., resorufin-AM$_2$ shown in FIG. 9, the resofurin compound thus obtained was dissolved in anhydrous dimethylformamide under nitrogen atmosphere at approximately 10 mM concentration. 3 eq. of bromomethyl acetate and 5 eq. of anhydrous triethylamine were then added via syringe. The mixture was stirred at room temperature overnight. To work up, dilute reaction mixture with 10 volumes of water, then extract desired compound twice into ethyl acetate. Dry combined ethyl acetate extracts with sodium sulfate, then remove volatiles under vacuum to give dark yellow oil.

To separate isomers a and b of resorufin-AM$_2$ by preparatory C18 HPLC, dark yellow oil was dissolved in 10% acetonitrile, then resolved in a linear 10%→90% acetonitrile gradient over 30 minutes with no acid/base additives. Resorufin-AM$_2$ isomers eluted approximately 1 minute apart, with isomer A eluting first. Desired fractions were collected and acetonitrile removed under vacuum. Orange-colored products (isomer a and b) as a powder were obtained after freeze-drying.

In Vitro LplA Mutant Activity Assay

DNA fragments encoding *E. coli* LplA (SEQ ID NO:11) single mutants W37V, E20A, F147A, and H149G, double mutants E20A+F147G, F147A+H149G, and E20A+F147A, and triple mutant E20A+F147A+H149G were prepared by routine mutagenesis and recombinant technology. These DNA fragments were cloned into expression vectors and expressed in E. coli cells. The ligase activity of the LplA mutants thus prepared in catalyzing formation of resorufin-LAP conjugate was tested as described below. 1 µM Lipoic acid ligase, 200 µM, LAP peptide (sequence=GFEIDKVWYDLDA), ligase, 500 µM resorufin-$AM_2$, 2 mM ATP, and 5 mM magnesium acetate were mixed in an Eppendorf tube and incubated at 30° C. for 1 hour. Components in the mixture were analyzed by C18 HPLC and tandem ESI-MS, using 15%→40% acetonitrile linear gradient over 8 minutes containing 0.1% formic acid to resolve resorufin, LAP, and resorufin-LAP conjugate. A mixtures omitting ATP or the lipoic acid ligase was used as a negative control.

As shown in the table below, both double mutant E20A+F147A and triple mutant E20A+F147A+H149G are active in catalyzing formation of the resorufin-LAP conjugate, indicating that these two mutants are specific to resorufin.

TABLE 1

Ligase Mutants and Reactivity to Resorufin

| Ligase mutant | Yield of resorufin-LAP conjugate |
|---|---|
| W37V | <5% |
| E20A | 0% |
| F147A | 0% |
| H149G | <5% |
| E20A + F147G | <5% |
| F147A + H149G | 5% |
| E20A + F147A | 40% |
| E20A + F147A + H149G | 100% |

As shown in Example 2 above, the W37V mutant is specific to coumarin (Kcat=0.019 $s^{-1}$). The Kcat of triple mutant E20A+F147A+H149G for catalyzing formation of the resorufin-LAP conjugate was determined to be 0.026 $s^{-1}$.

Fluorophore Targeting in Living Mammalian Cells

The DNA fragments encoding the E20A+F147A+H149G triple mutant was cloned into pcDNA3 plasmid to produce an expression vector capable of expressing this LplA mutant.

A DNA fragment encoding a fusion protein of LAP and a target protein, including fluorescent protein FP (e.g., blue fluorescent protein or green fluorescent protein), FP fused with a nuclear localization signal (FP-NLS), FP fused with a nuclear export signal (FP-NES), Vimentin, microtubule associated protein 2 (MAP2), Neurexin-1b, Neuroligin-1, low density lipoprotein receptor (LDLR), and transmembrane anchoring helix (TM), was prepared and also cloned into pcDNA3 plasmid to construct an expression vector capable of expressing the LAP-target fusion protein.

Human embryonic kidney cells (HEK 293T cells), Hela cells, or COS-7 cells were transfected with 400 ng of a mutant gene-containing expression vector and 400 ng LAP-target protein gene-containing expression vector using Lipofectamine 2000 (Life Technologies), following the manufacturer's instruction manual. 12-36 hours after the transfection, the culture medium was removed and the transfected cells were rinsed with Dulbecco's phosphate buffered saline (DPBS) or Hank's buffered salt solution (HBSS). The cells were then incubated with 5 µM resorufin-$AM_2$ (isomer a or isomer b) in the same buffer at 37° C. for 10 minutes. The cells were then rinsed with growth medium and cultured at 37° C. for 50 minutes for dye to wash out of cells. The same procedure was used for dissociated rat hippocampal neurons, except that the wash out period was 90 minutes. Protein labeling in the cells or tissues was observed by imaging. The result thus obtained indicates that resorufin was successfully linked to LAP-target fusion protein in cells co-transfected with the E20A+F147A+H149G mutant. Surprisingly, lower background was observed when using resorufin-$AM_2$ isomer a as the substrate as compared to isomer b.

Orthogonal Resorufin and 7-Hydroxycoumarin Labeling in Living Mammalian Cells

To confirm the substrate specificity of the E20A+F147A+H149G triple mutant, HEK 293T cells were co-transfected with the expression vector for the triple mutant and an expression vector for producing a nuclear-targeted fusion protein containing LAP and yellow fluorescent protein (LAP-YFP); or co-transfected with the expression vector for the W37V mutant (specific to 7-hydroxycoumarin) and the LAP-YFP expression vector following the method described above. After being rinsed with DPBS or HBSS, the transfected cells were incubated with 5 µM resorufin-$AM_2$ and 20 µM 7-hydrozycoumarin-$AM_2$ at 37° C. for 10 minutes. The structure of 7-hydrozycoumarin-$AM_2$ is shown in FIG. 9, panel B.

The cells were washed with the culture medium, cultured at 37° C. for 30 minutes, and observed under a fluorescent microscope. The results indicate that the E20A+F147A+H149G mutant only catalyzes conjugation of resorufin to the LAP-YFP fusion protein while the W37V mutant only catalyzes conjugate of 7-hydroxycoumarin to the LAP-YFP fusion protein.

Example 4

Materials and Methods (i) Cloning and Mutagenesis

Nucleotide sequences of all constructs utilized in this study are available at http://stellar.mit.edu/S/project/tinglabreagents/r02/materials.html. Constructs were prepared either by standard restriction cloning methods or QuikChange mutagenesis (Stratagene) as described by the manufacturer.

(ii) Peptide Sequences

While our previous reports[5-6] recommended 22-amino acid sequences for LAP1 (DEVLVEIETDKAVLEVPG-GEEE; SEQ ID NO:10, or DEVLVEIETDKAVLEV-PASADG; SEQ ID NO:33, respectively) as being more efficiently modified by LplA when fused to the C-terminal end of proteins of interest, we determined in this study that, for the purposes of interaction-dependent labeling, the originally designed 17-amino acid LAP1 sequence[5] (DEVLVEIETD-KAVLEVP; SEQ ID NO:8) is coumarin-labeled with equivalent efficiency to the 22-mer. Therefore all constructs utilized the 17-mer LAP1 peptide.

(iii) Mammalian Cell Culture

HEK, HeLa, and COS-7 cells were cultured in growth media consisting of Dulbecco's modification of Eagle's medium (DMEM, Cellgro) supplemented with 10% fetal bovine serum (FBS, PAA Laboratories), 50 units/mL penicillin, and 50 µg/mL streptomycin (Cellgro). Cells were maintained at 37° C. under an atmosphere of 5% CO2 unless otherwise noted. For imaging, cells were grown on glass coverslips. HeLa and COS-7 cells were grown directly on the glass substrate. HEK cells were grown on glass pre-treated with 50 µg/mL fibronectin (Millipore).

(iv) Fluorescence Imaging

Cells were imaged in Dulbecco's phosphate buffered saline (DPBS) on glass coverslips. A ZeissAxiovert 200M inverted microscope with a 40× oil-immersion objective was used for epifluorescence imaging. Coumarin (40020 excitation, 425 dichroic, 435/30 emission), YFP/Alexa Fluor 488 (493/16 ex-citation, 506 dichroic, 525/30 emission), mCherry/Alexa Fluor 568 (57020 excitation, 585 dichroic, 605/30 emission), Alexa Fluor 647 (63020 excitation, 660 dichroic, 680/30 emission) and differential interference contrast (DIC) images were collected. For confocal imaging, we utilized a Zeiss AxioObserver inverted microscope with a 60× oil-immersion objective, out-fitted with a Yokogawa spinning disk confocal head, a Quad-band notch dichroic mirror (405/488/568/647), and 405 (diode), 491 (DPSS), 561 (DPSS), and 640 nm (diode) lasers (all 50 mW). Coumarin (405 laser excitation, 445/40 emission), GFP/Alexa Fluor 488 (491 laser excitation, 528/38 emission), Alexa Fluor 568 (561 laser excitation, 617/73 emission), Alexa Fluor 647 (640 laser excitation, 700/75 emission), and DIC images were collected. All image analysis was with SlideBook software (Intelligent Imaging Innovations). Fluorophore intensities in each experiment were normalized to the same intensity ranges. Acquisition times ranged from 20 milliseconds to 5 seconds. All images were confocal except where indicated.

(v) Immunoblot Detection of Interaction-Dependent Lipoylation in Cells

COS-7 cells were grown to 50% confluency in a 24-well plate, then transfected with 600 ng FRB-LplA-pcDNA3 and 600 ng FKBP-LAP1-pcDNA3 per well using Lipofectamine 2000 (Invitrogen) according to the manufacturer's instructions. For comparison, FKBP-LAP1-pcDNA3 was replaced with FKBP-LAP2-pcDNA3 or FKBP-E2p-pcDNA3. 24 hours after transfection, growth media was removed and fresh growth media containing 100 nM rapamycin was applied to the cells for one hour at 37° C. Rapamycin was omitted from parallel wells as a negative control. The media was then re-moved, and pre-warmed DPBS containing 500 µM lipoic acid was applied to the cells for one minute. Longer lipoic acid treatment of 3 minutes reduces signal-to-noise ratio to 2.5:1 due to increasing background lipoylation, rendering a one-minute labeling time crucial. The labeling solution was removed and the cells were immediately lysed (and the reaction quenched) with direct application of SDS-PAGE loading buffer (40 µL per well). Samples were denatured by boiling for 5 minutes. 30 µL of this material was loaded per well on a 14% acrylamide SDS-PAGE gel, electrophoresed, then analyzed by Western blotting as described in the Methods section, except that detection was SuperSignal West Femto reagent (Pierce).

For Western blotting, proteins were transferred from gels to nitrocellulose for 120 minutes at 500 mA. Identical parallel reactions were run on an SDS-PAGE gel, then stained with Coommassie brilliant blue, as a loading control. After transfer, membranes were blocked with 3% BSA in Tris-buffered saline with 0.05% Tween-20 (TBS-T) for 1 hour at room temperature. For lipoic acid detection, the membrane was treated with rabbit polyclonal anti-lipoic acid antibody (Calbiochem) at a 1:300 dilution in 3% BSA in TBS-T at room temperature for one hour, then washed three times for 5 minutes with TBS-T. The membrane was then incubated with goat anti-rabbit horseradish peroxidase conjugate (Bio-Rad) in 3% BSA in TBS-T at a 1:3000 dilution for one hour at room temperature, then again washed three times for 5 minutes with TBS-T. Chemiluminescence detection was performed with SuperSignal West Pico reagent (Pierce), and imaged on an Alpha Innotech ChemiImager 5500. Spot densitometry was performed using AlphaEase FC version 3.2.2 software (Alpha Innotech). A rectangle was drawn around the visible extent of each band, and an identical box was drawn on the background neighboring each band of interest. The background-subtracted intensity values were then ratioed to assess labeling signal-to-noise.

(vi) Coumarin ID-PRIME in HEK Cells

HEK cells were grown to 70% confluency on fibronectin-coated glass coverslips, then transfected with 400 ng FRB-LplAW37V-pcDNA3, 400 ng FKBP-LAP1-pcDNA3, and 20 ng GFP as a co-transfection marker per 0.95 cm2 using Neofectin (Mid-Atlantic Biolabs) according to the manufacturer's instructions. For the LAP2 peptide comparison, FKBP-LAP1-pcDNA3 was replaced with FKBP-LAP2-pcDNA3. For negative control experiments, FKBP-LAP1-pcDNA3 was replaced with FKBP-LAP1(K→A)-pcDNA3, or FRB-LplAW37V-pcDNA3 was replaced with FRB-LplA-pcDNA3. 24 hours after transfection, 100 nM rapamycin was added in growth media for 1 hour at 37° C., or omitted as a negative control. Growth media was then removed and the cells were labeled by applying 20 µM coumarin-AM2 in serum-free DMEM at 37° C. for 10 minutes. Excess coumarin was washed out with three changes of fresh DMEM over 60 minutes at 37° C. Cells were imaged in DPBS. Confocal images were acquired at 60× magnification.

(vii) Rapamycin Dose-Response

HEK cells were grown to 70% confluency on fibronectin-coated glass coverslips, then transfected with 400 ng FRB-LplAW37V-pcDNA3 and 400 ng FKBP-LAP1-pcDNA3 per 0.95 cm2 using Lipofectamine 2000 (Invitrogen) according to the manufacturer's instructions. 24 hours after transfection, concentrations of rapamycin ranging from 0.3 nM to 300 nM were added in growth media for 1 hour at 37° C. Growth media was then removed and the cells were labeled by applying 20 µM coumarin-AM2 in serum-free DMEM at 37° C. for 10 minutes. Excess coumarin was washed out with one application of fresh DMEM for 30 minutes. Cells were then fixed with 3.7% paraformaldehyde in DPBS at 4° C. for 10 minutes, then permeabilized with cold methanol at −20° C. for 10 minutes. Fixed cells were washed with DPBS, then blocked overnight in blocking buffer (3% BSA in DPBS with 0.1% Tween-20, or DPBS-T) at 4° C. Cells were then immunostained serially with 1:1000 dilutions in blocking buffer of the following antibodies in the following order, for one hour each at room temperature: mouse anti-c-myc, goat anti-mouse Alexa Fluor 647 conjugate, rabbit anti-HA, goat anti-rabbit Alexa Fluor 568 conjugate. Three five-minute DPBS washes were applied between each antibody incubation step. Epifluorescence images of cells in DPBS were acquired at 40× magnification.

For quantiation, ROIs were manually drawn on transfected cells by visually inspecting the anti-c-myc immunofluorescence images. Average intensities of coumarin, anti-c-myc immunofluorescence, and anti-HA immunofluorescence were computed. Background correction was applied by drawing a ROI on an untransfected cell in each field of view and subtracting these background intensities from all values generated from that particular field of view. ROIs with anti-HA intensities greater than 3000 were kept for analysis, leaving at least 8 data points for each rapamycin concentration and as many as 25. The coumarin intensity was ratioed to the anti-c-myc intensity for each ROI; these values were averaged for each rapamycin concentration. Error bars, ±s.e.m.

(viii) Coumarin Labeling of the Interaction of PSD-95 and Neuroligin-1 in HEK Cells HEK cells were grown to 70% confluency on fibronectin-coated glass coverslips, then transfected with 100 ng PSD-95-LplAW37V-pNICE, 500 ng AP-neuroligin-1-LAP1-pNICE, and 20 ng GFP per cm2 using Neofectin according to the manufacturer's instructions. For negative controls, AP-neuroligin-1-LAP1-pNICE was replaced with an equal amount of AP-neuroligin-1 (ΔPDZ)-LAP1-pNICE, or PSD-95-LplAW37V-pNICE was replaced with 20 ng FLAG-LplAW37V-pcDNA3. 24 hours after transfection, the cells were labeled by applying 20 μM coumarin-AM2 in serum-free DMEM at 37° C. for 10 minutes. Excess coumarin was washed out with three changes of fresh DMEM over 60 minutes at 37° C. Cells were imaged in DPBS. Confocal images were acquired at 60× magnification.

Results

To determine the suitability of the LplA-LAP1 pair for detecting PPIs, we first investigated interaction-dependent labeling with LplA's natural small-molecule substrate, lipoic acid, was investigated, using the rapamycin-dependent interaction of FRB and FKBP proteins as a model system. LplA was fused to the C-terminus of FRB and LAP1 to the C-terminus of FKBP, since the crystal structure of the FRB-rapamycin-FKBP complex indicates that these ends are only 18 Å apart.[9]

Interaction-dependent lipoylation of FKBP-LAP1 by FRB-LplA was detected in vitro using purified proteins combined at 10 μM each with a +/− rapamycin signal-to-background ratio of >12:1 by anti-lipoic acid immunoblot analysis. Similar results were obtained for purified proteins at 1 μM each. Interaction-dependent lipoylation was also performed in COS7 cells, followed by cell lysis and immunoblot analysis, with a signal-to-background ratio of 15:1. Furthermore, replacing the high-Km LAP1 substrate with the low-Km substrates LAP2 and E2p produced high background labeling in the absence of an interaction (in the absence of rapamycin) inside COS7 cells. While gel-based analysis of interaction-dependent lipoylation in live cells works well, immunofluorescence detection after cell fixation was poor, which might due to background signal from endogenous lipoylated proteins in mitochondria. Interaction-dependent lipoylation signal (in the presence of rapamycin condition) above mitochondrial background was observed when FRB-LplA and FKBP-LAP1 were both strongly overexpressed. These results indicate that LplA and LAP1 suffice as the halves of an enzymatic complementation assay for PPI detection.

While interaction-dependent lipoylation validated the use of LplA and LAP 1 for a PPI reporter, lipoic acid detection requires antibody staining. To develop a live-cell sensor, wild-type LplA was replaced with the coumarin ligase LplAW37V. To perform labeling, FKBP-LAP1 and FRB-LplAW37V were co-expressed in living cells. Addition of rapamycin promoted complex formation. Treatment of cells with coumarin-AM2 probe7 for 10 minutes allowed coumarin loading into cells. Subsequent incubation of cells in probe-free media allowed excess, unligated coumarin to leave the cell via non-specific anion transporters.

Performing ID-PRIME labeling in living HEK cells produced coumarin labeling in transfected cells, but not neighboring untransfected cells. Background was undetectable in the absence of rapamycin. With longer coumarin treatment times of >20 min, background coumarin signal began to accumulate in cells highly overexpressing the FKBP and FRB reporters. The signal-to-background ratio for 10-min labeling was reproducibly >5:1 across experiments and sometimes as high as 15:1. Replacing the high-Km LAP1 with the low-Km substrate LAP2 produced high labeling in the absence of an interaction. Additional controls show that coumarin ID-PRIME was sitespecific and enzyme-dependent.

Mutating the central lysine of LAP1 to alanine eliminated labeling, demonstrating that this was the unique site of coumarin attachment. Utilizing wild-type LplA, which has no coumarin ligation activity, in place of LplAW37V also eliminated labeling. When the cells were fixed after coumarin labeling and wash-out, immunofluorescence staining revealed that the coumarin labeling pattern matched the localization of FKBP-LAP. Multiple mutants of LplA exhibited coumarin ligase activity.[7]

The W37V mutation provides the highest sensitivity, but exhibited increased background at high expression levels, relative to W37I7. ID-PRIME labeling of FKBPLAP1 with FRB fusions was compared to either LplAW37I or LplAW37V. Better coumarin signal was observed at low FKBPLAP1 expression levels with FRB-LplAW37V. However, background for LplAW37V increased with expression level, while LplAW37I background remained undetectable across all expression levels. This provides insights as to how to optimize the enzyme used for ID-PRIME labeling according to the system under consideration. For example, proteins expressed at low levels may require LplAW37V for optimal sensitivity, while for highly over-expressed proteins, use of LplAW37I may be preferable to maintain low background.

The generality of coumarin ID-PRIME in other cell lines and subcellular compartments were investigated. ID-PRIME gave consistently high signal-to-background for the FRB/FKBP system in HEK, COS7, and HeLa. ID-PRIME also reports the subcellular localization of PPIs. When the same experiment was performed, but FKBP constructs were restricted to the nucleus by appending a nuclear localization signal (NLS), the coumarin signal was also nuclear. These results indicate that the ID-PRIME method described herein is not restricted to specific types of cells or subcellular compartment.

To test the tolerance of ID-PRIME for different fusion geometries, the original constructs, FRB-LplAW37V and FKBP-LAP1, were compared to a swapped pair, FRB-LAP1 and FKBP-LplAW37V. Both pairs exhibited low background in the absence of rapamycin, but not all of the cells transfected with the latter pair were stained with coumarin, in contrast to cells expressing the former reporter pair. The FRB-LAP1/FKBP-LplAW37V pair may have reduced sensitivity due to decreased ligase-peptide steric access. Therefore, when applying ID-PRIME to image new PPIs, it is preferred to make and test multiple LplAW37V and LAP1 fusions to the proteins of interest.

An HPLC assay was utilized to measure the Michaelis-Menten parameters for ligation of coumarin probe to purified FKBP-LAP1 by LplAW37V. The Km of the enzyme for LAP1 was 681±168 μM, providing an upper bound to protein concentrations that should be possible to study using ID-PRIME. The kcat for coumarin ligation to LAP1 was 0.60±0.06 min-1, not much lower than the reported kcat of 1.14 min-1 for coumarin ligation to LAP27, indicating that utilizing the Km-impaired substrate did not sacrifice sensitivity. While this catalytic rate was 22 times slower than lipoic acid ligation[8], it was predicted that it should be sufficient to label PPIs with a half life of 1 minute or more.

The sensitivity of ID-PRIME was also characterized by quantifying the coumarin labeling yield. The red fluorescent protein mCherry was fused to FKBP-LAP1, allowing quantification of the concentration of this protein inside cells by comparison to a purified reference standard (the "wedge method").[10] The concentration of ligated coumarin was qualified in live cells. The labeling yield was determined by plotting the coumarin concentration against the mCherry-FKBP-LAP1 concentration for single cells. In the presence of rapamycin, a 10-minute coumarin labeling gives a yield of 7.7±0.6%. A similar labeling yield was observed after a 20-minute coumarin labeling, indicating that the FKBP-rapamycin-FRB complex did not turn over during this labeling time. By comparing the slopes of the +/− rapamycin linear fits, it was determined that a minimum concentration of 6 µM mCherry-FKBP-LAP1 was required to give a signal-to-background ratio >2:1.

ID-PRIME was compared to a well-characterized imaging-based PPI reporter. Bimolecular fluorescence complementation (BiFC) has been applied to the visualization of hundreds PPIs inside living mammalian cells due to its ease of use, good sensitivity, and low background[11]. In BiFC, enhanced yellow fluorescent protein (YFP) is split into two non-fluorescent fragments, which, when fused to interacting proteins, associate and fold to reconstitute YFP[12]. To quantitatively compare ID-PRIME to BiFC, the BiFCreporter fragments YN155 and YC15512 were fused to the C-terminal ends of FRB and FKBP, respectively, to make them as similar to the ID-PRIME constructs as possible. The BiFC reporters were expressed in HEK cells in the presence or absence of rapamycin at a normal growth temperature of 37° C., or at the reduced temperature of 30° C., which reportedly increased BiFC signal by promoting YFP fluorophore maturation[13]. ID-PRIME reporter-expressing cells were grown and labeled under identical conditions to facilitate direct comparison between the methods. The cells were then fixed to assay expression of all constructs by immunostaining prior to YFP and coumarin imaging. Linear regression analysis of the single-cell plots revealed that, while the absolute signal for BiFC was about twice as high for cells grown at 30° C. relative to cells grown at 37° C., the signal-to-background ratio was approximately 8:1 for both conditions, similar to the 10:1 ratio previously reported for BiFC1. In analogous experiments, the ID-PRIME signal-to-background ratio ranged from 5:1 to 15:1, and the absolute signal was similar to that of BiFC. Therefore, ID-PRIME provides a similar signal-to-noise response as BiFC while addressing the limitations of temporal resolution and complex trapping.

To determine whether fusion of target proteins to LplAW37V and LAP1 perturbs the PPI under study, the apparent dissociation constant of FRB-LplAW37V and FKBP-LAP1 were measured by performing a rapamycin dose-response experiment. As noted above, the FKBP-rapamycin-FRB complex does not appear to dissociate during the labeling time. This single enzymatic turnover provides a direct readout of the subpopulation of interacting proteins. ID-PRIME labeling was performed in cells treated with varying concentrations of rapamycin, and plotted the coumarin labeling intensity in single cells, measured by imaging, against rapamycin concentration. As shown in FIG. 11, the dose-response curve thus generated was fit with a dissociation constant of 3.1±0.6 nM rapamycin, in good agreement with the previously published Kd of 2.5 nM14. Therefore the interaction of FRB and FKBP does not appear to be perturbed by genetic fusion to the reporter.

ID-PRIME labeling was applied to study another PPI as follows. Neuroligin-1 is a post-synaptic adhesion protein that interacts with pre-synaptic neurexins across the synaptic cleft to promote excitatory synapse formation and maturation.[15] The intracellular interaction of the C-terminus of neuroligin-1 with the third PDZ domain of PSD-9516, a post-synaptic scaffolding protein, has been implicated in this process.[17] The membrane localization of this interacting pair, as well as the sensitivity of the interaction to genetic fusions of neuroligin at the C terminus18, make it a challenging interaction to detect. It was demonstrated in this study that the interaction of PSD-95 and neuroligin-1 ID-PRIME was specifically labeled in HEK cells by ID-PRIME. More specifically, LAP1 was fused to the intracellular portion of neuroligin-1, at the T776 site previously shown to tolerate insertions without perturbing the localization of the protein.[18] LplAW37V was fused to the C-terminus of PSD-95, the same location previously re-ported for fluorescent protein fusions.[19] When these constructs were co-expressed in living HEK cells, the coumarin labeling protocol described above afforded membrane-localized neuroligin-1-LAP1 labeling. Neuroligin-1 (ΔPDZ)-LAP1, which includes the deletion of the three C-terminal amino acids of native neuroligin-1-LAP1 to abolish interaction with PSD-9516, was used as a negative control. Coumarin labeling was not observed in cells co-expressing neuroligin-1 (ΔPDZ)-LAP1 with PSD-95-LplAW37V. Similarly, co-expressing neuroligin-1-LAP1 with LplAW37V in the absence of fusion to PSD-95 afforded no coumarin labeling. These results demonstrate that ID-PRIME is a reliable method for studying protein-protein interaction in heterologous cells.

In conclusion, the ID-PRIME method described herein can be used for imaging PPIs in living cells. With as less as a ten-minute labeling time, ID-PRIME visualized inducible interactions of proteins expressed at micromolar concentrations inside living cells. ID-PRIME is complementary to the well-established BiFC method in that it utilizes a short labeling protocol and does not trap interacting proteins in complex. This method can be extended to studies on cell surface PPI and secretory pathway, by incorporating red-shifted fluorophores with emission farther from cellular autofluorescence, and by improving ligation kinetics to improve detection of transient PPIs

REFERENCES FOR EXAMPLE 4

1. Robida, A. M.; Kerppola, T. K., Bimolecular fluorescence complementation analysis of inducible protein interactions: effects of factors affecting protein folding on fluorescent protein fragment association. J Mol Biol 2009, 394 (3), 391-409.
2. Kerppola, T. K., Visualization of molecular interactions by fluorescence complementation. Nat Rev Mol Cell Biol 2006, 7 (6), 449-56.
3. (a) Zamyatnin, A. A., Jr.; Solovyev, A. G.; Bozhkov, P. V.; Valkonen, J. P.; Morozov, S. Y.; Savenkov, E. I., Assessment of the integral membrane protein topology in living cells. Plant J 2006, 46 (1), 145-54; (b) Tilsner, J.; Cowan, G. H.; Roberts, A. G.; Chapman, S, N.; Ziegler, A.; Savenkov, E.; Torrance, L., Plasmodesmal targeting and intercellular movement of potato mop-top pomovirus is mediated by a membrane anchored tyrosine-based motif on the lumenal side of the endoplasmic reticulum and the C-terminal transmembrane domain in the TGB3 movement protein. Virology 2010, 402 (1), 41-51; (c) Walter, M.; Chaban, C.; Schutze, K.; Batistic, O.; Weckermann, K.; Nake, C.; Blazevic, D.; Grefen, C.; Schumacher, K.; Oecking, C.; Harter, K.; Kudla, J., Visualization of protein interactions in living plant cells using bimolecular fluorescence complementation. Plant J 2004, 40 (3), 428-38.
4. Fernandez-Suarez, M.; Chen, T. S.; Ting, A. Y., Protein-protein interaction detection in vitro and in cells by proximity biotinylation. J Am Chem Soc 2008, 130 (29), 9251-3.
5. Fernandez-Suarez, M.; Baruah, H.; Martinez-Hernandez, L.; Xie, K. T.; Baskin, J. M.; Bertozzi, C. R.; Ting, A. Y., Redirecting lipoic acid ligase for cell surface protein labeling with small-molecule probes. Nat Biotechnol 2007, 25 (12), 1483-7.
6. Baruah, H.; Puthenveetil, S.; Choi, Y. A.; Shah, S.; Ting, A. Y., An engineered aryl azide ligase for site-specific mapping of protein-protein interactions through photo-cross-linking. Angew Chem Int Ed Engl 2008, 47 (37), 7018-21.

7. Uttamapinant, C.; White, K. A.; Baruah, H.; Thompson, S.; Fernandez-Suarez, M.; Puthenveetil, S.; Ting, A. Y., A fluorophore ligase for site-specific protein labeling inside living cells. Proc Natl Acad Sci USA 2010, 107 (24), 10914-9.
8. Puthenveetil, S.; Liu, D. S.; White, K. A.; Thompson, S.; Ting, A. Y., Yeast display evolution of a kinetically efficient 13-amino acid substrate for lipoic acid ligase. J Am Chem Soc 2009, 131 (45), 16430-8.
9. Choi, J.; Chen, J.; Schreiber, S. L.; Clardy, J., Structure of the FKBP12-rapamycin complex interacting with the binding domain of human FRAP. Science 1996, 273 (5272), 239-42.
10. Adams, S. R.; Campbell, R. E.; Gross, L. A.; Martin, B. R.; Walkup, G. K.; Yao, Y.; Llopis, J.; Tsien, R. Y., New biarsenical ligands and tetracysteine motifs for protein labeling in vitro and in vivo: synthesis and biological applications. J Am Chem Soc 2002, 124 (21), 6063-76.
11. Kerppola, T. K., Visualization of molecular interactions by fluorescence complementation. Nature Reviews Molecular Cell Biology 2006, 7 (6), 449-456.
12. Hu, C. D.; Chinenov, Y.; Kerppola, T. K., Visualization of interactions among bZIP and Rel family proteins in living cells using bimolecular fluorescence complementation. Mol. Cell 2002, 9 (4), 789-798.
13. Kerppola, T. K., Design and implementation of bimolecular fluorescence complementation (BiFC) assays for the visualization of protein interactions in living cells. Nat Protoc 2006, 1 (3), 1278-86.
14. Chen, J.; Zheng, X. F.; Brown, E. J.; Schreiber, S. L., Identification of an 11-kDa FKBP12-rapamycin-binding domain within the 289-kDa FKBP12-rapamycin-associated protein and characterization of a critical serine residue. Proc Natl Acad Sci USA 1995, 92 (11), 4947-51.
15. (a) Song, J. Y.; Ichtchenko, K.; Sudhof, T. C.; Brose, N., Neuroligin 1 is a postsynaptic cell-adhesion molecule of excitatory synapses. Proc Natl Acad Sci USA 1999, 96 (3), 1100-5; (b) Ichtchenko, K.; Hata, Y.; Nguyen, T.; Ullrich, B.; Missler, M.; Moomaw, C.; Sudhof, T. C., Neuroligin 1: a splice site-specific ligand for beta-neurexins. Cell 1995, 81 (3), 435-43; (c) Ichtchenko, K.; Nguyen, T.; Sudhof, T. C., Structures, alternative splicing, and neurexin binding of multiple neuroligins. J Biol Chem 1996, 271 (5), 2676-82.
16. Irie, M.; Hata, Y.; Takeuchi, M.; Ichtchenko, K.; Toyoda, A.; Hirao, K.; Takai, Y.; Rosahl, T. W.; Sudhof, T. C., Binding of neuroligins to PSD-95. Science 1997, 277 (5331), 1511-5.
17. Prange, O.; Wong, T. P.; Gerrow, K.; Wang, Y. T.; El-Husseini, A., A balance between excitatory and inhibitory synapses is controlled by PSD-95 and neuroligin. Proc Natl Acad Sci USA 2004, 101 (38), 13915-20.
18. Sara, Y.; Biederer, T.; Atasoy, D.; Chubykin, A.; Mozhayeva, M. G.; Sudhof, T. C.; Kavalali, E. T., Selective capability of SynCAM and neuroligin for functional synapse assembly. J Neurosci 2005, 25 (1), 260-70.
19. (a) Heine, M.; Thoumine, O.; Mondin, M.; Tessier, B.; Giannone, G.; Choquet, D., Activity-independent and subunit-specific recruitment of functional AMPA receptors at neurexin/neuroligin contacts. Proc Natl Acad Sci USA 2008, 105 (52), 20947-52; (b) de Wit, J.; Sylwestrak, E.; O'Sullivan, M. L.; Otto, S.; Tiglio, K.; Savas, J. N.; Yates, J. R., 3rd; Comoletti, D.; Taylor, P.; Ghosh, A., LRRTM2 interacts with Neurexin 1 and regulates excitatory synapse formation. Neuron 2009, 64 (6), 799-806.

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation. It is intended to encompass all such modifications and equivalents within the scope of the appended claims.

All references, patents and patent applications that are recited in this application are incorporated by reference herein in their entirety.

What is claimed is:

1. An isolated lipoic acid ligase mutant that uses resorufin as a substrate, the mutant comprising an amino acid sequence that is at least 85% identical to SEQ ID NO:11 and includes mutations at residues corresponding to E20 and F147 in SEQ ID NO:11.

2. The lipoic acid ligase mutant of claim 1, wherein the mutant further comprises a mutation at the residue corresponding to H149 in SEQ ID NO:11.

3. The lipoic acid ligase mutant of claim 1, wherein the amino acid sequence is at least 95% identical to SEQ ID NO:11.

4. The lipoic acid ligase mutant of claim 2, wherein the mutant includes amino acid residue substitutions corresponding to E20A, F147A, and H149G.

5. The lipoic acid ligase mutant of claim 2, wherein the amino acid sequence of the mutant is otherwise identical to SEQ ID NO:11 except for the E20A, F147A, and H149G substitutions.

* * * * *

SEQUENCE LISTING

<160> NUMBER OF SEQ ID NOS: 34

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Gly Leu Asn Asp Ile Phe Glu Ala Asp Lys Ala Glu Trp His Glu
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 2

Gly Asp Thr Leu Cys Ile Val Glu Ala Asp Lys Ala Met Asn Gln Ile
1               5                   10                  15

Glu

```
<210> SEQ ID NO 3
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 3

Gly Asp Thr Leu Cys Ile Val Glu Ala Asp Lys Ala Ser Met Glu Ile
1               5                   10                  15

Pro

<210> SEQ ID NO 4
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 4

Glu Gln Ser Leu Ile Thr Val Glu Gly Asp Lys Ala Ser Met Glu Val
1               5                   10                  15

Pro

<210> SEQ ID NO 5
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 5

Asp Asp Val Leu Cys Glu Val Gln Asn Asp Lys Ala Val Val Glu Ile
1               5                   10                  15

Pro

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Asp Glu Val Leu Val Glu Ile Glu Thr Asp Lys Val Val Leu Glu Val
1               5                   10                  15

Pro

<210> SEQ ID NO 7
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 7

Gly Asp Asp Cys Ala Val Ala Glu Ser Val Lys Ala Ala Ser Asp Ile
1               5                   10                  15

Tyr

<210> SEQ ID NO 8
<211> LENGTH: 17
<212> TYPE: PRT
<213> ORGANISM: Artificial Sequence
```

```
<220> FEATURE:
<223> OTHER INFORMATION: Synthetic Peptide

<400> SEQUENCE: 8

Asp Glu Val Leu Val Glu Ile Glu Thr Asp Lys Ala Val Leu Glu Val
1               5                   10                  15

Pro

<210> SEQ ID NO 9
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 9

Asp Glu Val Leu Val Glu Ile Glu Thr Asp Lys Ala Val Leu Glu Val
1               5                   10                  15

Pro

<210> SEQ ID NO 10
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 10

Asp Glu Val Leu Val Glu Ile Glu Thr Asp Lys Ala Val Leu Glu Val
1               5                   10                  15

Pro Gly Gly Glu Glu Glu
            20

<210> SEQ ID NO 11
<211> LENGTH: 337
<212> TYPE: PRT
<213> ORGANISM: E. coli

<400> SEQUENCE: 11

Ser Thr Leu Arg Leu Leu Ile Ser Asp Ser Tyr Asp Pro Trp Phe Asn
1               5                   10                  15

Leu Ala Val Glu Glu Cys Ile Phe Arg Gln Met Pro Ala Thr Gln Arg
                20                  25                  30

Val Leu Phe Leu Trp Arg Asn Ala Asp Thr Val Val Ile Gly Arg Ala
            35                  40                  45

Gln Asn Pro Trp Lys Glu Cys Asn Thr Arg Arg Met Glu Glu Asp Asn
    50                  55                  60

Val Arg Leu Ala Arg Arg Ser Ser Gly Gly Gly Ala Val Phe His Asp
65                  70                  75                  80

Leu Gly Asn Thr Cys Phe Thr Phe Met Ala Gly Lys Pro Glu Tyr Asp
                85                  90                  95

Lys Thr Ile Ser Thr Ser Ile Val Leu Asn Ala Leu Asn Ala Leu Gly
                100                 105                 110

Val Ser Ala Glu Ala Ser Gly Arg Asn Asp Leu Val Val Lys Thr Val
            115                 120                 125

Glu Gly Asp Arg Lys Val Ser Gly Ser Ala Tyr Arg Glu Thr Lys Asp
    130                 135                 140

Arg Gly Phe His His Gly Thr Leu Leu Leu Asn Ala Asp Leu Ser Arg
145                 150                 155                 160
```

```
Leu Ala Asn Tyr Leu Asn Pro Asp Lys Lys Leu Ala Ala Lys Gly
                165                 170                 175
Ile Thr Ser Val Arg Ser Arg Val Thr Asn Leu Thr Glu Leu Leu Pro
            180                 185                 190
Gly Ile Thr His Glu Gln Val Cys Glu Ala Ile Thr Glu Ala Phe Phe
        195                 200                 205
Ala His Tyr Gly Glu Arg Val Glu Ala Glu Ile Ile Ser Pro Asn Lys
    210                 215                 220
Thr Pro Asp Leu Pro Asn Phe Ala Glu Thr Phe Ala Arg Gln Ser Ser
225                 230                 235                 240
Trp Glu Trp Asn Phe Gly Gln Ala Pro Ala Phe Ser His Leu Leu Asp
                245                 250                 255
Glu Arg Phe Thr Trp Gly Gly Val Glu Leu His Phe Asp Val Glu Lys
            260                 265                 270
Gly His Ile Thr Arg Ala Gln Val Phe Thr Asp Ser Leu Asn Pro Ala
        275                 280                 285
Pro Leu Glu Ala Leu Ala Gly Arg Leu Gln Gly Cys Leu Tyr Arg Ala
    290                 295                 300
Asp Met Leu Gln Gln Glu Cys Glu Ala Leu Leu Val Asp Phe Pro Glu
305                 310                 315                 320
Gln Glu Lys Glu Leu Arg Glu Leu Ser Ala Trp Met Ala Gly Ala Val
                325                 330                 335
Arg

<210> SEQ ID NO 12
<211> LENGTH: 1245
<212> TYPE: DNA
<213> ORGANISM: E. coli

<400> SEQUENCE: 12
gttaaccgcc agcaaaccgg tgccggaaga ggaagaaagc gagaaaaaag agtgacccat      60
tactacaaga aaggaaatcg ttatgtccac attacgcctg ctcatctctg actcttacga    120
cccgtggttt aacctggcgg tggaagagtg tattttcgc caaatgcccg ccacgcagcg     180
cgttctgttt ctctggcgca atgccgacac ggtagtaatt ggtcgcgcgc agaacccgtg    240
gaaagagtgt aatacccggc ggatggaaga agataacgtc cgcctggcgc ggcgcagtag    300
cggtggcggc gcggtgttcc acgatctcgg caatacctgc tttacccttta tggctggcaa    360 gccggagtac gataaaacta tctccacgtc gattgtgctc aatgcgctga cgcgctcgg     420 cgtcagcgcc gaagcgtccg gacgtaacga tctggtggtg aaaaccgtcg aaggcgaccg    480
caaagtctca ggctcggcct atcgcgaaac caaagatcgc ggcttccacc acggcacctt    540
gctactcaat gccgacctca gccgcctggc aaactatctc aatccggata aaagaaaact    600
ggcggcgaaa ggcattacgt cggtacgttc ccgcgtgacc aacctcaccg agctgttgcc    660
ggggatcacc catgagcagg tttgcgaggc ataaccgag gccttttcg cccattatgg      720 cgagcgcgtg gaagcggaaa tcatctcccc gaacaaaacg ccagacttgc caaacttcgc    780
cgaaaccttt gcccgccaga gtagctggga atggaacttc ggtcaggctc cggcattctc    840
gcatctgctg gatgaacgct ttacctgggg cggcgtggaa ctgcatttcg acgttgaaaa    900
aggccatatc acccgcgccc aggtgtttac cgacagcctc aaccccgcgc cgctggaagc    960
cctcgccgga cgactgcaag gctgcctgta ccgcgcagat atgctgcaac aggagtgcga   1020
agcgctgttg gttgacttcc cggaacagga aaaagagcta cgggagttat cggcatggat   1080
```

```
ggcggggggct gtaaggtagt tacccgccca tgcgggcaac tttctcttcg atttgccgga      1140
ttttttccgg catttcttgc gcaatgtggc gaaacgcctc gctgatacgc ggatctctgg      1200
cgaccgtttg ccagaactcg tgcgccagcg ggatcgccgt taacc                      1245
```

<210> SEQ ID NO 13
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 13

```
aaaagctagc ggcctgaacg acatcttcga agccgacaaa gctgaatggc acgagggcgg      60
tgaggaggag tacgccgtgg                                                  80
```

<210> SEQ ID NO 14
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 14

```
aaaagctagc ggcgataccc tgtgcatcgt tgaagccgac aaagctgaaa accagatcga      60
aggcggtgag gaggagtacg ccgtgg                                           86
```

<210> SEQ ID NO 15
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 15

```
aaaagctagc ggcgataccc tgtgcatcgt tgaagccgac aaagcttcta tggaaatccc      60
gggcggtgag gaggagtacg ccgtgg                                           86
```

<210> SEQ ID NO 16
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 16

```
aaaagctagc gaacagtcgc tgatcaccgt agaaggcgac aaagcttcta tggaagttcc      60
gggcggtgag gaggagtacg ccgtgg                                           86
```

<210> SEQ ID NO 17
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 17

```
aaaagctagc gacgatgtac tgtgcgaagt acagaacgac aaagctgtag ttgaaatccc      60
gggcggtgag gaggagtacg ccgtgg                                           86
```

<210> SEQ ID NO 18
<211> LENGTH: 86

<212> TYPE: DNA
<213> ORGANISM: Artificial Sequence
<220> FEATURE:
<223> OTHER INFORMATION: Synthetic Oligonucleotide

<400> SEQUENCE: 18
aaaagctagc gacgaagtac tggttgaaat cgaaaccgac aaagtagttc tggaagtacc    60
gggcggtgag gaggagtacg ccgtgg                                          86

<210> SEQ ID NO 19
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 19
aaaagctagc ggcgatgact gcgctgttgc tgaatctgta aaagctgcct cggacatcta    60
tggcggtgag gaggagtacg ccgtgg                                          86

<210> SEQ ID NO 20
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 20
atcgaaaccg acaaagcagt tctggaagta ccgggc                               36

<210> SEQ ID NO 21
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 21
aaaacatatg gaggaggagt acgccgtgg                                       29

<210> SEQ ID NO 22
<211> LENGTH: 94
<212> TYPE: DNA
<213> ORGANISM: Artificial Sequence
<220> FEATURE:
<223> OTHER INFORMATION: Synthetic Oligonucleotide

<400> SEQUENCE: 22
ttttggatcc tcttacggta cttccagaac tgctttgtcg gtttcgattt caaccagtac    60
ttcgtcgcta gcatccttgc ggctcgcctc gtac                                 94

<210> SEQ ID NO 23
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 23
ttttggatcc tcttactcct cctcaccgcc cggtacttcc agaactgctt tgtc           54

<210> SEQ ID NO 24
<211> LENGTH: 92
<212> TYPE: DNA

<213> ORGANISM: Artificial Sequence
<220> FEATURE:
<223> OTHER INFORMATION: Synthetic Oligonucleotide

<400> SEQUENCE: 24
aaaaactagt cgggctgacg aagtactggt tgaaatcgaa accgacaaag cagttctgga    60
agtaccggca tcagcagacg gcgctagcaa aa    92

<210> SEQ ID NO 25
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 25
ggttgaaatc gaaaccgacg ccgcagttct ggaagtaccg g    41

<210> SEQ ID NO 26
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 26
cgaaggcgac cgcgcagtct caggctcgg    29

<210> SEQ ID NO 27
<211> LENGTH: 96
<212> TYPE: DNA
<213> ORGANISM: Artificial Sequence
<220> FEATURE:
<223> OTHER INFORMATION: Synthetic Oligonucleotide

<400> SEQUENCE: 27
aaaaaagatc tggcggcgac gaagtactgg ttgaaatcga aaccgacaaa gcagttctgg    60
aagtaccggg cggtgaggag gagggcgcgc caaaaa    96

<210> SEQ ID NO 28
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 28
ggttgaaatc gaaaccgacg ccgcagttct ggaagtaccg g    41

<210> SEQ ID NO 29
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 29
cgggcggtga ggaggagact gtgagcaagg gcgaggag    38

<210> SEQ ID NO 30
<211> LENGTH: 69
<212> TYPE: DNA
<213> ORGANISM: Artificial Sequence
<220> FEATURE:
<223> OTHER INFORMATION: Synthetic Oligonucleotide

```
<400> SEQUENCE: 30
gtacctccag aactgctttg tcggtttcga tttcaaccag tacttcgtca cttctgtcgc    60
caactgcag                                                           69

<210> SEQ ID NO 31
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 31
ggaggtaccg gcatcagcag acggcggggg agaattcgac agatgtg                 47

<210> SEQ ID NO 32
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 32

Gly Phe Glu Ile Asp Lys Val Trp Tyr Asp Leu Asp Ala
 1               5                  10

<210> SEQ ID NO 33
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 33

Asp Glu Val Leu Val Glu Ile Glu Thr Asp Lys Ala Val Leu Glu Val
 1               5                  10                  15

Pro Ala Ser Ala Asp Gly
             20

<210> SEQ ID NO 34
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 34
ttttgaattc ggatccttgc ggctcgcctc gtac                               34
```